US012622893B2

(12) United States Patent
Fang et al.

(10) Patent No.: US 12,622,893 B2
(45) Date of Patent: May 12, 2026

(54) ALPHA2 ADRENERGIC AGONIST CODRUGS CONJUGATED WITH MUSCARINIC AGONIST DRUGS

(71) Applicant: ADS THERAPEUTICS LLC, Irvine, CA (US)

(72) Inventors: Wenkui Ken Fang, Irvine, CA (US); Jinsong Ni, Irvine, CA (US); Rong Yang, Irvine, CA (US); Van Dinh, Irvine, CA (US)

(73) Assignee: ADS Therapeutics LLC

( * ) Notice: Subject to any disclaimer, the term of this patent is extended or adjusted under 35 U.S.C. 154(b) by 343 days.

(21) Appl. No.: 18/287,040

(22) PCT Filed: Mar. 31, 2022

(86) PCT No.: PCT/US2022/022835
§ 371 (c)(1),
(2) Date: Oct. 16, 2023

(87) PCT Pub. No.: WO2022/221071
PCT Pub. Date: Oct. 20, 2022

(65) Prior Publication Data

US 2024/0216337 A1 Jul. 4, 2024

Related U.S. Application Data

(60) Provisional application No. 63/272,134, filed on Oct. 26, 2021, provisional application No. 63/176,149, filed on Apr. 16, 2021.

(51) Int. Cl.

| | |
|---|---|
| ***C07D 233/90*** | (2006.01) |
| ***A61K 9/00*** | (2006.01) |
| ***A61K 31/4178*** | (2006.01) |
| ***A61P 27/02*** | (2006.01) |

(52) U.S. Cl.
CPC ........ *A61K 31/4178* (2013.01); *A61K 9/0048* (2013.01); *A61P 27/02* (2018.01); *C07D 233/90* (2013.01)

(58) Field of Classification Search
CPC .................................................... C07D 233/90
See application file for complete search history.

(56) References Cited

U.S. PATENT DOCUMENTS 8,765,177 B2 7/2014 Levine et al.

FOREIGN PATENT DOCUMENTS

| | | | |
|---|---|---|---|
| WO | 2007017669 | A1 | 2/2007 |
| WO | 2009117042 | A1 | 9/2009 |
| WO | 2012037490 | A1 | 3/2012 |
| WO | WO 2020/252061 | A1 | 12/2020 |

OTHER PUBLICATIONS

International Preliminary Report on Patentability in International Appln. No. PCT/US2022/022835, mailed on Oct. 26, 2023, 6 pages.
International Search Report and Written Opinion in International Appln. No. PCT/US2022/022835, mailed on Jun. 14, 2022, 13 pages.
Kim et al., "Neuroprotective effects of human serum albumin nanoparticles loaded with brimonidine on retinal ganglion cells in optic nerve crush model," Investigative ophthalmology & visual science, Aug. 2015, 56(9):5641-9.
Nair et al., "Blood brain barrier permeable gold nanocluster for targeted brain imaging and therapy: an in vitro and in vivo study," Journal of Materials Chemistry B, 2017, 5(42):8314-21.

*Primary Examiner* — John S Kenyon
(74) *Attorney, Agent, or Firm* — Fish & Richardson P.C.

(57) ABSTRACT

A co-drug or a pharmaceutical salt thereof includes a muscarinic agonist moiety and an alpha2 adrenergic agonist moiety. The muscarinic agonist moiety and the alpha2 adrenergic agonist moiety are connected covalently via a linker, and the link includes an ester bond, an amide bond, a carbamate bond, or a combination thereof.

9 Claims, 2 Drawing Sheets

ALPHA2 ADRENERGIC AGONIST CODRUGS CONJUGATED WITH MUSCARINIC AGONIST DRUGS

This application is the US National Stage Application of PCT/US2022/022835, filed on Mar. 31, 2022, which claims priority to U.S. Provisional Patent Application Nos. 63/176,149, filed on Apr. 16, 2021 and 63/272,134, filed on Oct. 26, 2021, both of which are incorporated by reference for all purposes as if fully set forth herein.

FIELD OF THE INVENTION

The present invention relates to a codrug of an alpha2 adrenergic agonist conjugated with a muscarinic agonist drug, a process for preparing the same, a pharmaceutical composition containing the same and the use as pharmaceuticals to treat various diseases. The present invention further describes single drug entities, formed by direct linkage of an alpha2 adrenergic agonist to a muscarinic agonist. Upon drug administration, the single drug entity undergoes selective cleavage at the linkage region to release the adrenergic agonist and the muscarinic agonist individual drugs.

BACKGROUND OF THE INVENTION

Alpha2 adrenergic agonists in the ocular application, for example, are well established drugs for lowering IOP and are used for treating glaucoma. This class of drugs can decrease the fluid production that supplies the liquid to maintain IOP. On the other hand, they can also increase the out-flow of liquid from vitreous humor. This double acting mechanism on both inflow and outflow makes them effective treatments for glaucoma.

Presbyopia is another ocular indication that can be treated with alpha2 adrenergic agonists. They inhibit dilator muscle to reduce muscle activity. Since this muscle contributes to the opening of pupil, the alpha2 agonists will reduce the pupil size. This action causes an increase of the depth of field. Presbyopia is the reduced ability to see close objects and is associated with normal aging. The increased depth of field will make a person with presbyopia see close object more clearly.

Muscarinic agonists are used for many diseases, including ocular indications. Their mechanisms of action in the eye are mostly mediated through the M3 receptor. Muscarinic agonists are used to treat glaucoma because they can contract the ciliary body muscle and opens the trabecular meshwork to increase the outflow of aqueous humor. This action help to reduce the IOP and can be used to treat glaucoma. This mechanism of action is different from the alpha2 mechanism discussed earlier, thus a muscarinic agonist, when combined with an alpha2 compound, may result in better efficacy.

The muscarinic agonist can also be used to improve eyesight in persons with presbyopia. However, the mechanism of action is still not very clear and some agonists considered to be in the same class may work through different mechanisms. For example, pilocarpine is effective in treating presbyopia and the proposed mechanism is improving accommodation, possibly through ciliary tonic contraction reduction. But this hypothesis has not been proven. Another muscarinic drug, carbachol, may act on sphincter muscle to constrict pupil size. This action will increase the depth of field so that persons with presbyopia can see close objects more clearly. Since the pupil effect has a different mechanism than the alpha2 drugs, combining muscarinic agonist with an alpha agonist has synergistic effect on pupil constriction.

A conjugate drug, also referred to as a co-drug, includes two or more different or same drugs within one single chemical entity wherein each drug contains an appropriate chemical functionality to enable them to be connected directly, which is cleavable and biologically labile. The alpha2 adrenergic agonist moiety and the muscarinic agonist moiety of the co-drug compounds disclosed herein are connected to each other via covalent bonds, such that said bond degrades in vivo to yield the respective muscarinic agonist and alpha2 adrenergic agonist. Each bond is, for example, an amide bond or an ester bond or others depending on the nature of the bonding site.

By appropriate structural design, it may be possible to control the release of each drug. When the drugs are chemically combined, the resulting co-drug will usually have different physicochemical properties compared to the individual parent drugs, which may provide superior properties for delivery when compared to delivery of a physical mixture of the drugs. Enzymatic or hydrolytic degradation of these covalent bonds generally, yields the corresponding acid, or alcohol by hydrolysis or by a related reaction. A compound which degrades in vivo yields the active muscarinic agonist drug and the active alpha2 adrenergic agonist drug at some point in the metabolic process of the claimed compound.

SUMMARY OF THE INVENTION

In one embodiment, the present application discloses a co-drug that includes a muscarinic agonist moiety and an alpha2 adrenergic agonist moiety, or a pharmaceutical salt thereof. The muscarinic agonist moiety and the alpha2 adrenergic agonist moiety are connected covalently via a linker, and the link comprises an ester bond, an amide bond, a carbamate bond, or a combination thereof.

In another embodiment, the co-drug is a compound of Formula I, an enantiomer, a diastereoisomer, a hydrate, a solvate, a crystal form, or a tautomer thereof.

Formula I

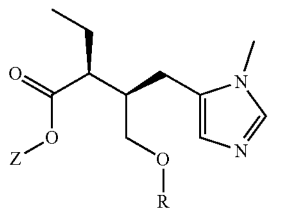

R is H, —CO—$C_{1-8}$ alkyl, —CO—$C_{1-8}$ alkyloxy; —CO-aryl, —CO-aryloxy, —CO—$C_{1-8}$ alkylaryl, or —CO—$C_{1-8}$ alkylaryloxy; Z is

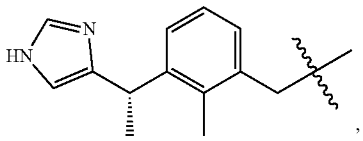

,

-continued

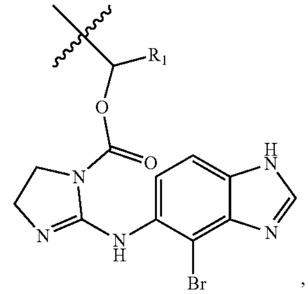

,

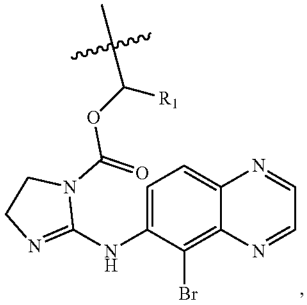

,

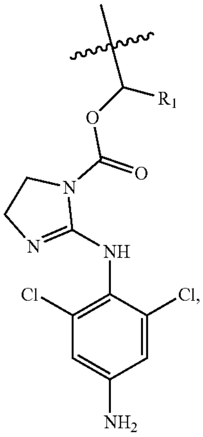

or

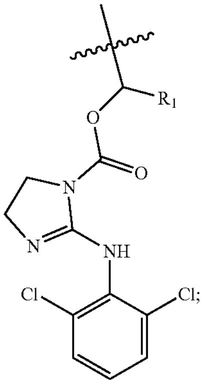

and $R^1$ is H or $C_{1-3}$ alkyl.

In another embodiment, the co-drug is a compound of Formula II, an enantiomer, a diastereoisomer, a hydrate, a solvate, a crystal form, or a tautomer thereof.

Formula II

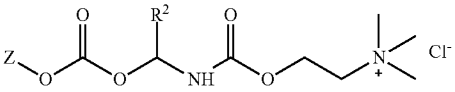

$R^2$ is H, $C_{1-3}$ alkyl; $C_{1-8}$ alkyloxy; aryl, aryloxy, $C_{1-8}$ alkylaryl, or $C_{1-8}$ alkylaryloxy; Z is

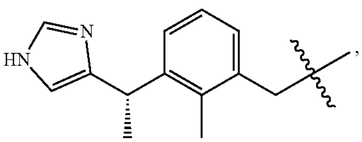

-continued

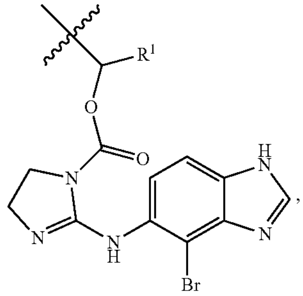

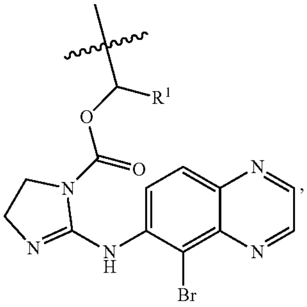

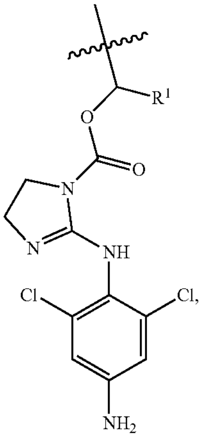

or

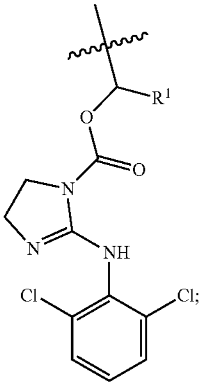

and $R^1$ is H or $C_{1-3}$ alkyl.

In another embodiment, the co-drug is a compound of Formula III, an enantiomer, a diastereoisomer, a hydrate, a solvate, a crystal form, or a tautomer thereof, Formula III

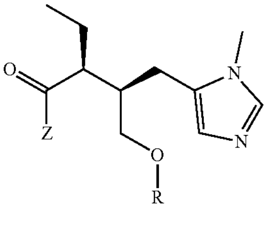

R is H, —CO—$C_{1-18}$ alkyl, —CO—$C_{1-18}$ alkyloxy; —CO-aryl, —CO-aryloxy, —CO—$C_{1-18}$ alkylaryl, or —CO—$C_{1-18}$ alkylaryloxy; and Z is:

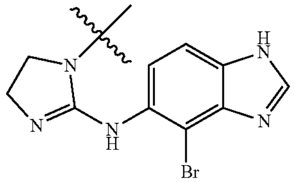
,

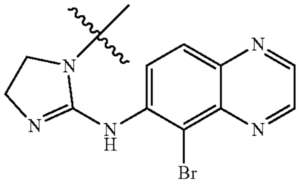
,

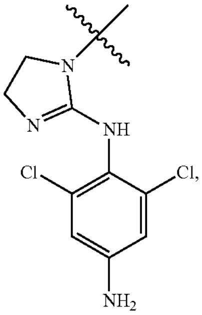
, or

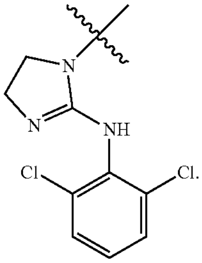
.

In another embodiment, the co-drug is selected from the group consisting of 3-((S)-1-(1H-imidazol-4-yl)ethyl)-2-methylbenzyl (2S,3R)-2-ethyl-4-hydroxy-3-((1-methyl-1H-imidazol-5-yl)methyl)butanoate; 3-((S)-1-(1H-imidazol-4-yl)ethyl)-2-methylbenzyl (2S,3R)-4-acetoxy-2-ethyl-3-((1-methyl-1H-imidazol-5-yl)methyl)butanoate; (((2S,3R)-2-ethyl-4-hydroxy-3-((1-methyl-1H-imidazol-5-yl)methyl) butanoyl)oxy)methyl 2-((4-bromo-1H-benzo[d]imidazol-5-yl)amino)-4,5-dihydro-1H-imidazole-1-carboxylate; (((2S, 3R)-4-acetoxy-2-ethyl-3-((1-methyl-1H-imidazol-5-yl) methyl)butanoyl)oxy)methyl 2-((4-bromo-1H-benzo[d] imidazol-5-yl)amino)-4,5-dihydro-1H-imidazole-1-carboxylate; (((2S,3R)-2-ethyl-4-hydroxy-3-((1-methyl-1H-imidazol-5-yl)methyl)butanoyl)oxy)methyl 2-((5-bromoquinoxalin-6-yl)amino)-4,5-dihydro-1H-imidazole-1-carboxylate; (((2S,3R)-4-acetoxy-2-ethyl-3-((1-methyl-1H-imidazol-5-yl)methyl)butanoyl)oxy)methyl 2-((5-bromoquinoxalin-6-yl)amino)-4,5-dihydro-1H-imidazole-1-carboxylate; 1-(((2S,3R)-2-ethyl-4-hydroxy-3-((1-methyl-1H-imidazol-5-yl)methyl)butanoyl)oxy)ethyl 2-((4-bromo-1H-benzo[d]imidazol-5-yl)amino)-4,5-dihydro-1H-imidazole-1-carboxylate; 1-(((2S,3R)-4-acetoxy-2-ethyl-3-((1-methyl-1H-imidazol-5-yl)methyl)butanoyl)oxy)ethyl 2-((4-bromo-1H-benzo[d]imidazol-5-yl)amino)-4,5-dihydro-1H-imidazole-1-carboxylate; 1-(((2S,3R)-2-ethyl-4-hydroxy-3-((1-methyl-1H-imidazol-5-yl)methyl)butanoyl) oxy)ethyl 2-((5-bromoquinoxalin-6-yl)amino)-4,5-dihydro-1H-imidazole-1-carboxylate; 1-(((2S,3R)-4-acetoxy-2-ethyl-3-((1-methyl-1H-imidazol-5-yl)methyl)-butanoyl) oxy)ethyl 2-((5-bromoquinoxalin-6-yl)amino)-4,5-dihydro-1H-imidazole-1-carboxylate; (2R,3S)-3-(2-((4-bromo-1H-benzo[d]imidazol-5-yl)amino)-4,5-dihydro-1H-imidazole-1-carbonyl)-2-((1-methyl-1H-imidazol-5-yl)methyl)pentyl acetate; (2R,3S)-3-(2-((4-bromo-1H-benzo[d]imidazol-5-yl)amino)-4,5-dihydro-1H-imidazole-1-carbonyl)-2-((1-methyl-1H-imidazol-5-yl)methyl)pentyl propionate; (2R, 3S)-3-(2-((4-bromo-1H-benzo[d]imidazol-5-yl)amino)-4,5-dihydro-1H-imidazole-1-carbonyl)-2-((1-methyl-1H-imidazol-5-yl)methyl)pentyl butyrate; (2R,3S)-3-(2-((4-bromo-1H-benzo[d]imidazol-5-yl)amino)-4,5-dihydro-1H-imidazole-1-carbonyl)-2-((1-methyl-1H-imidazol-5-yl) methyl)pentyl cyclopropanecarboxylate; (2R,3S)-3-(2-((4-bromo-1H-benzo[d]imidazol-5-yl)amino)-4,5-dihydro-1H-imidazole-1-carbonyl)-2-((1-methyl-1H-imidazol-5-yl) methyl)pentyl oleate; (2R,3S)-3-(2-((4-bromo-1H-benzo[d] imidazol-5-yl)amino)-4,5-dihydro-1H-imidazole-1-carbonyl)-2-((1-methyl-1H-imidazol-5-yl)methyl)pentyl (9Z,12Z)-octadeca-9,12-dienoate; (2R,3S)-3-(2-((5-bromoquinoxalin-6-yl)amino)-4,5-dihydro-1H-imidazole-1-carbonyl)-2-((1-methyl-1H-imidazol-5-yl)methyl)pentyl acetate; (2R,3S)-3-(2-((5-bromoquinoxalin-6-yl)amino)-4,5-dihydro-1H-imidazole-1-carbonyl)-2-((1-methyl-1H-imidazol-5-yl)methyl)pentyl propionate; (2R,3S)-3-(2-((5-bromoquinoxalin-6-yl)amino)-4,5-dihydro-1H-imidazole-1-carbonyl)-2-((1-methyl-1H-imidazol-5-yl)methyl)pentyl butyrate; (2R,3S)-3-(2-((5-bromoquinoxalin-6-yl)amino)-4,5-dihydro-1H-imidazole-1-carbonyl)-2-((1-methyl-1H-imidazol-5-yl)methyl)pentyl cyclopropanecarboxylate; (2R, 3S)-3-(2-((5-bromoquinoxalin-6-yl)amino)-4,5-dihydro-1H-imidazole-1-carbonyl)-2-((1-methyl-1H-imidazol-5-yl) methyl)pentyl oleate; (2R,3S)-3-(2-((5-bromoquinoxalin-6-yl)amino)-4,5-dihydro-1H-imidazole-1-carbonyl)-2-((1-methyl-1H-imidazol-5-yl)methyl)pentyl (9Z,12Z)-octadeca-9,12-dienoate; (2R,3S)-3-(2-((4-amino-2,6-dichlorophenyl)amino)-4,5-dihydro-1H-imidazole-1-carbonyl)-2-((1-methyl-1H-imidazol-5-yl)methyl)pentyl acetate; (2R,3S)-3-(2-((4-amino-2,6-dichlorophenyl) amino)-4,5-dihydro-1H-imidazole-1-carbonyl)-2-((1-methyl-1H-imidazol-5-yl)methyl)pentyl propionate; (2R, 3S)-3-(2-((4-amino-2,6-dichlorophenyl)amino)-4,5-dihydro-1H-imidazole-1-carbonyl)-2-((1-methyl-1H-imidazol-5-yl)methyl)pentyl butyrate; (2R,3S)-3-(2-((4-amino-2,6-dichlorophenyl)amino)-4,5-dihydro-1H-imidazole-1-carbonyl)-2-((1-methyl-1H-imidazol-5-yl) methyl)pentyl cyclopropanecarboxylate; (2R,3S)-3-(2-((4-amino-2,6-dichlorophenyl)amino)-4,5-dihydro-1H-imidazole-1-carbonyl)-2-((1-methyl-1H-imidazol-5-yl) methyl)pentyl oleate; (2R,3S)-3-(2-((4-amino-2,6-dichlorophenyl)amino)-4,5-dihydro-1H-imidazole-1-carbonyl)-2-((1-methyl-1H-imidazol-5-yl)methyl)pentyl (9Z,12Z)-octadeca-9,12-dienoate; (2R,3S)-3-(2-((2,6-dichlorophenyl)amino)-4,5-dihydro-1H-imidazole-1-carbonyl)-2-((1-methyl-1H-imidazol-5-yl)methyl)pentyl acetate; (2R,3S)-3-(2-((2,6-dichlorophenyl)amino)-4,5-dihydro-1H-imidazole-1-carbonyl)-2-((1-methyl-1H-imidazol-5-yl) methyl)pentyl propionate; (2R,3S)-3-(2-((2,6-dichlorophenyl)amino)-4,5-dihydro-1H-imidazole-1-carbonyl)-2-((1-methyl-1H-imidazol-5-yl)methyl)pentyl butyrate; (2R,3S)-3-(2-((2,6-dichlorophenyl)amino)-4,5-dihydro-1H-imidazole-1-carbonyl)-2-((1-methyl-1H-imidazol-5-yl) methyl)pentyl cyclopropanecarboxylate; (2R,3S)-3-(2-((2,6-dichlorophenyl)amino)-4,5-dihydro-1H-imidazole-1-carbonyl)-2-((1-methyl-1H-imidazol-5-yl)methyl)pentyl oleate; and (2R,3S)-3-(2-((2,6-dichlorophenyl)amino)-4,5-dihydro-1H-imidazole-1-carbonyl)-2-((1-methyl-1H-imidazol-5-yl)methyl)pentyl (9Z,12Z)-octadeca-9,12-dienoate.

In another embodiment, the present application discloses a pharmaceutical composition comprising as active ingredient a therapeutically effective amount of the co-drug according to the present application and a pharmaceutically acceptable adjuvant, diluent or carrier.

In another embodiment, the pharmaceutical composition is formulated for ocular administration, systemic administration, oral administration, intravenous administration, intradermal administration, or intracavernous administration.

In another embodiment, the pharmaceutical composition is an eyedrop, a gel, or an implant.

In another embodiment, the eyedrop is a solution, a suspension, or an emulsion.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Reference will now be made in detail to embodiments of the present invention, example of which is illustrated in the accompanying drawings.

The present invention provides a co-drug that includes a muscarinic agonist moiety and an alpha2 adrenergic agonist moiety, or a pharmaceutical salt thereof. The muscarinic agonist moiety and the alpha2 adrenergic agonist moiety are connected covalently via a linker, and the link includes an ester bond, an amide bond, a carbamate bond, or a combination thereof. The linker metabolites or hydrolyzes in vivo to yield the respective muscarinic agonist and alpha2 adrenergic agonist independently.

Figure 1:
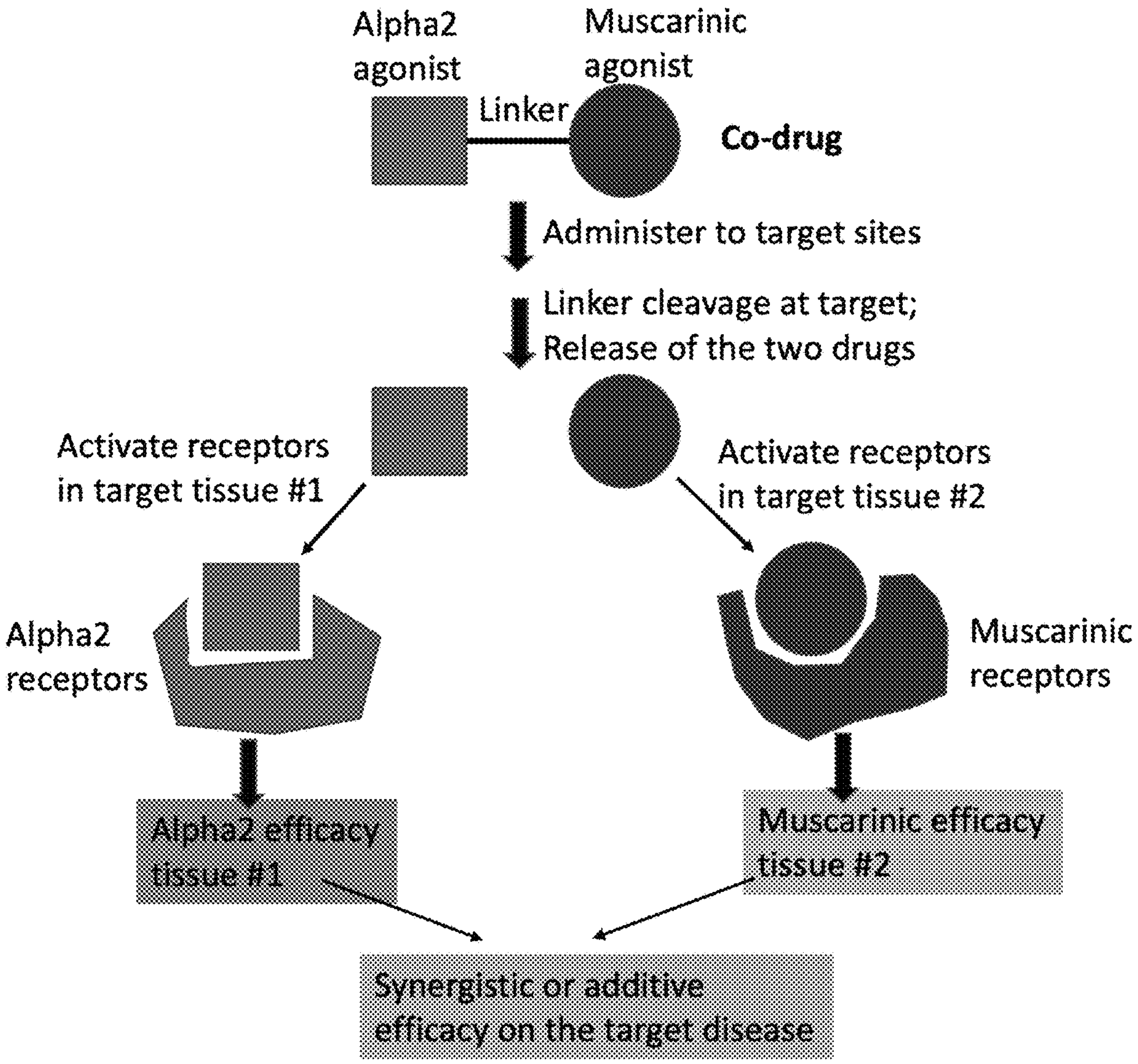
FIG. 1 show the mechanism (MOA) of the co-drug of the present application.

FIG. 1 The mechanism of action (MOA) of the invention. The alpha2 and muscarinic agonists are released from the co-drug when administered to the target sites. The two drugs modulate different pathways to result in synergistic or additive effects on target diseases. The target tissues can be multiple, can be different and can be the same.

The co-drugs of the invention provide a unique delivery of a muscarinic agonist and an alpha2 adrenergic agonist for the treatment and prevention of diseases such as presbyopia and glaucoma. A single drug entity is advantageous to individual dosing of each drug because of the ability for simultaneous dosing and elimination of washout concerns when applying each drug separately.

A muscarinic agonist moiety is a muscarinic agonist drug molecular or a part thereof that can be covalently linked to another molecular. The muscarinic agonist includes, but not limited to, acetylcholine, arecoline, bethanechol, carbachol, cevimeline, methacholine, muscarine, NGX267, oxotremorine, oxotremorine-M, OXA-22, pilocarpine, and xanomeline.

An alpha2 adrenergic agonist is an alpha2 adrenergic agonist drug molecular or a part thereof that can be covalently linked to another molecular. The alpha2 adrenergic agonist includes, but not limited to, apraclonidine, mivaZerol, clonidine, brimonidine, alpha methyl dopa, guanfacine, dexemeditomidine, (+)-(S)-4-1-(2,3-dimethyl-phenyl)-ethyl-1,3-dihydro-imidazole-2-thione, 1-(imidazolidin-2-yl) iminolindazole, methoxamine, phenylephrine, tizanidine, xylazine, guanabenz, and amitraz.

In another aspect, the co-drug is a compound of Formula I:

Formula I

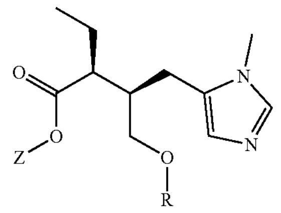

Those skilled in the art will be able to routinely modify and/or adapt the following schemes to synthesize any compound of the invention covered by Formula I.

The present invention concerns also processes for preparing the compounds of Formula I. The compounds of formula I according to the invention can be prepared analogously to conventional methods as understood by the person skilled in the art of synthetic organic chemistry. The synthetic scheme set forth below, illustrates how compounds according to the invention can be made.

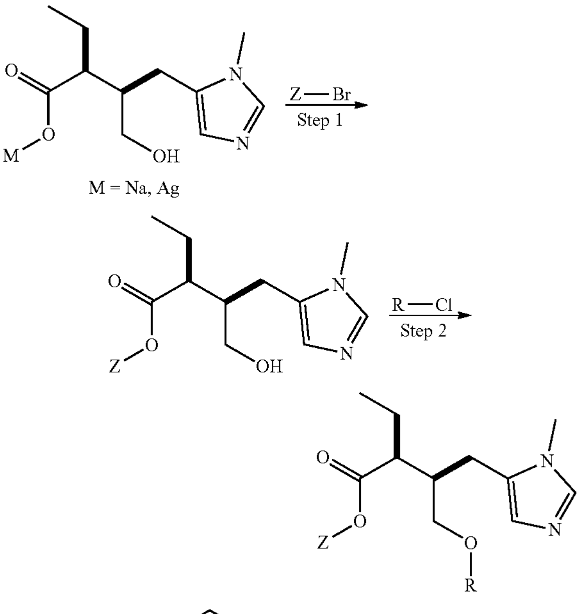

Z =

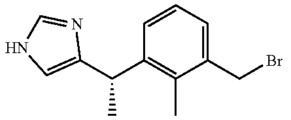

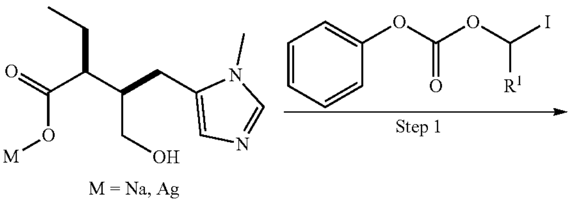

-continued

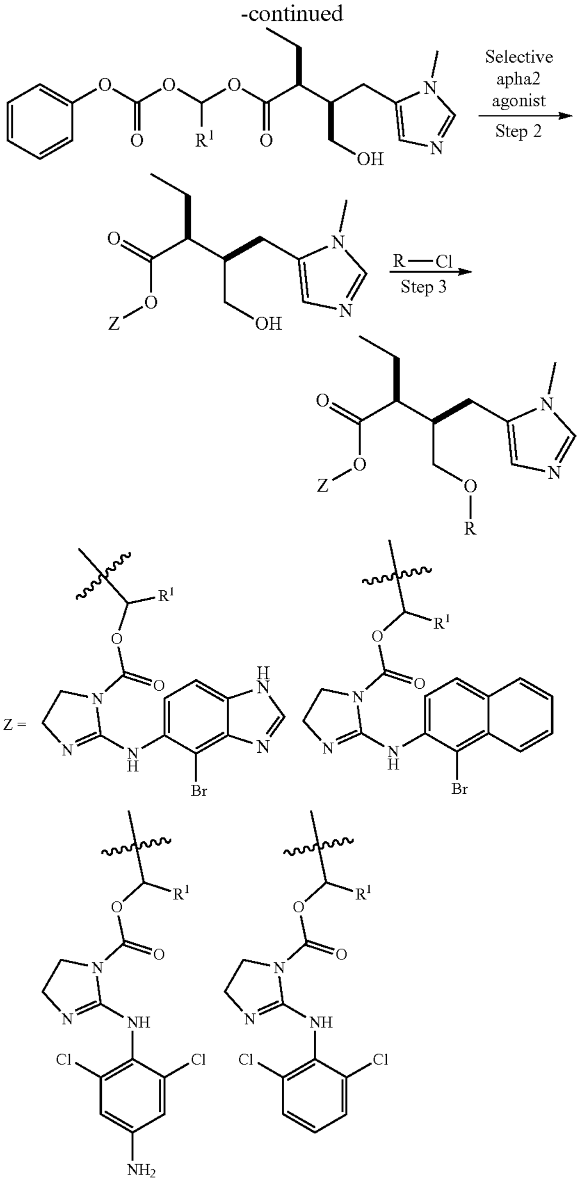

Those skilled in the art will be able to routinely modify and/or adapt the following scheme to synthesize any compounds of the invention covered by Formula I.

In another aspect, the co-drug is a compound of Formula II:

Formula II

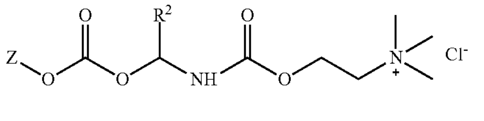

The compounds of formula II according to the invention can be prepared analogously to conventional methods as understood by the person skilled in the art of synthetic organic chemistry.

In another aspect, the co-drug is a compound of Formula III:

Formula I

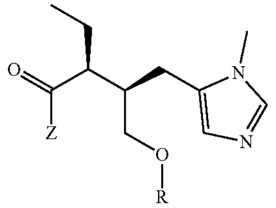

Those skilled in the art will be able to routinely modify and/or adapt the following schemes to synthesize any compound of the invention covered by Formula III.

The present invention concerns also processes for preparing the compounds of Formula I. The compounds of formula I according to the invention can be prepared analogously to conventional methods as understood by the person skilled in the art of synthetic organic chemistry. The synthetic scheme set forth below, illustrates how compounds according to the invention can be made.

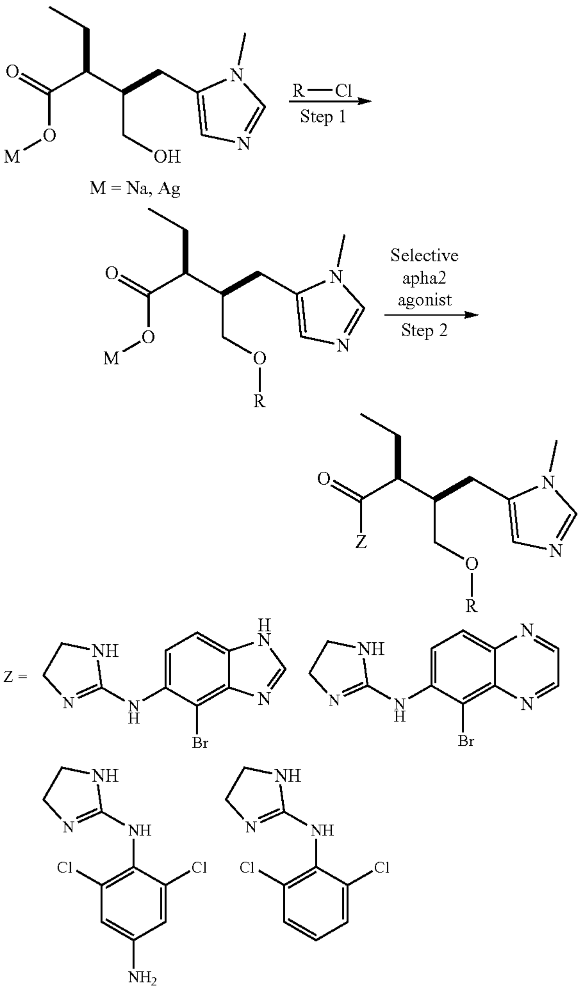

In another aspect, the invention is used for treating ocular diseases. The ocular indications include, but not limit to, glaucoma, elevated intraocular pressure, ocular hypertension, presbyopia, myopia, ocular rosacea, dry eye disease, meibomian gland dysfunction, blepharitis, allergic conjunctivitis, atopic keratoconjunctivitis, vernal keratoconjunctivitis, pterygium, pinguecula, corneal transplant rejection, graft versus host disease, ocular allergy, uveitis, anterior uveitis, Behcet's disease, Sjogren's syndrome, Stevens-Johnson syndrome, ocular cicatricial pemphigoid, chronic ocular surface inflammation caused by viral infection, herpes simplex keratitis, macular degeneration, including non-exudative age related macular degeneration, exudative age related macular degeneration, and acute macular degeneration, choroidal neovascularization, central retinal vein occlusion, diabetic retinopathy, proliferative vitreoretinopathy (PVR), diabetic uveitis, edema, including macular edema, cystoid macular edema and diabetic macular edema, acute macular neuroretinopathy, optic neuropathy, retinitis pigmentosa, retinal detachment, ocular trauma.

In another aspect, the invention is used for treating non-ocular diseases, including, but not limiting to, ischemic neuropathies, pain, visceral pain, headache pain, migraine, cancer pain, back pain, irritable bowel syndrome pain, neuropathic pain, muscle pain and pain associated with diabetic neuropathy, stroke, drug dependence and addiction, withdrawal symptoms, obesity, insulin resistance, stress-related conditions, diarrhea, diuresis, nasal congestion, spasticity, psychoses, depression, autoimmune disease, Crohn's disease, gastritis, Alzheimer's, Parkinson's, Amyotrophic lateral sclerosis (ALS), and other neurodegenerative diseases, dermatological conditions, skin erythema (redness) and inflammation, rosacea, acne, psoriasis, inflammatory bowel disease (IBD), cognitive dysfunctions such as cognitive impairment, forgetfulness, confusion, memory loss, deficits in visual perception, and cognitive dysfunctions associated with mental disorders such as neurodegenerative disorders, dementia, age-related cognitive decline, and Down's syndrome; neuropsychiatric disorders such as sleep disorders, psychosis, hallucinations, aggressiveness, paranoia, schizophrenia, attention deficit disorders, and Tourette's syndrome; eating disorders such as anorexia nervosa and bulimia; anxiety disorders such as obsessive compulsive disorders, panic disorders, phobic disorders, and posttraumatic stress disorders; mood disorders, such as bipolar disorder, and major depressive disorder; neurodegenerative disorders and conditions such as alcoholism, Alzheimer's disease, amyotrophic lateral sclerosis, frontotemporal lobar degeneration, Huntington's disease, HIV-associated dementia, Lewy body dementia, multiple sclerosis, Pick's disease, and progressive supranuclear palsy.

In another aspect, the invention provides a method comprising administrating to an eye of a human a pharmaceutical composition comprising a therapeutically active amount of a co-drug comprising at least one muscarinic agonist and one alpha2 adrenergic agonist, which are connected via a covalent bond wherein said covalent bond metabolizes or hydrolyzes or degrades in vivo to yield the muscarinic agonist and alpha2 adrenergic agonist, wherein each bond is an ester bond or an amide bond or others, wherein said method is effective in the treatment of presbyopia or glaucoma affecting said eye.

In another aspect, the invention provides a pharmaceutical composition comprising a co-drug comprising a muscarinic agonist moiety and an alpha2 adrenergic agonist, which are connected via two separate covalent bonds to each other, that said covalent bonds metabolize or hydrolyze or degrade in vivo to yield the muscarinic agonist and alpha2 adrenergic agonist, and wherein each bond is an ester bond or an amide bond or others, and wherein said pharmaceutical composition is formulated for ocular administration such as eyedrops or gel injection or implant injection.

The term "alkyl," as used herein, refers to saturated, monovalent hydrocarbon moieties having linear or branched moieties or combinations thereof and containing 1 to 8 carbon atoms. One methylene ($—CH_2—$) group of the alkyl can be replaced by oxygen, sulfur, sulfoxide, nitrogen, carbonyl, carboxyl, sulfonyl, or by a divalent $C_{3-8}$ cycloalkyl. Alkyl groups can be independently substituted by halogen atoms, hydroxyl groups, cycloalkyl groups, amine groups, heterocyclic groups, carboxylic acid groups, phosphonic acid groups, sulphonic acid groups, phosphoric acid groups, nitro groups, amide groups, sulfonamides groups.

The term "aryl," as used herein, refers to an organic moiety derived from an aromatic hydrocarbon consisting of a ring containing 6 to 10 carbon atoms by removal of one hydrogen. Aryl can be monocyclic or polycyclic. Aryl can be substituted by halogen atoms, nitro groups, cyano groups, $—OC_{1-6}$ alkyl groups, $—SC_{1-6}$ alkyl groups, $—C_{1-6}$ alkyl groups, $—C_{2-6}$ alkenyl groups, $—C_{2-6}$ alkynyl groups, carboxylic acid groups, ester groups, ketone groups, aldehyde groups, amide groups, amine groups, sulfonamide groups, $C_{3-8}$ cycloalkyl groups or hydroxyl groups. Usually aryl is phenyl. Preferred substitution sites on aryl are meta and para positions.

The term "alkyloxy," as used herein, refers to an alkyl group singularly bonded to oxygen. The term "aryloxy," as used herein, refers to an aryl group singularly bonded to oxygen. The term "alkylaryl," as used herein, refers to an alkyl group singularly bonded to an aryl group. The term "alkylaryloxy," as used herein, refers to an alkylaryl group singularly bonded to oxygen.

The term "amide" as used herein, represents a group of formula "$—C(O)NR^xR^y$" wherein $R^x$ and $R^y$ can be the same or independently H, alkyl, aryl, cycloalkyl, cycloalkenyl, heterocycle as defined above. The term "ester" as used herein, represents a group of formula "$—C(O)OR^x$," wherein $R^x$ can be alkyl, aryl, cycloalkyl, cycloalkenyl, heterocycle as defined above. The term "carbamate" as used herein, represents a group of formula "$—OC(O)NR^xR^y$," wherein $R^x$ and $R^y$ can be alkyl, aryl, cycloalkyl, cycloalkenyl, heterocycle as defined above.

The formula "H," as used herein, represents a hydrogen atom.

Some compounds of Formulae I-III and some of their intermediates have at least one stereogenic center in their structure. This stereogenic center may be present in an R or S configuration.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formulae I-III are able to form.

The acid addition salt form of a compound of Formula I, II, or II that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic acid, hydroxyacetic acid, propanoic acid, lactic acid, pyruvic acid, malonic acid, fumaric acid, maleic acid, oxalic acid, tartaric acid, succinic acid, malic acid, ascorbic acid, benzoic acid, tannic acid, pamoic acid, citric acid, methylsulfonic acid, ethanesulfonic acid, benzenesulfonic acid, formic and the like.

The base addition salt form of a compound of Formula I, II, or III that occurs in its acid form can be obtained by treating the acid with an appropriate base such as an inorganic base, for example, sodium hydroxide, magnesium hydroxide, potassium hydroxide, Calcium hydroxide, ammonia and the like; or an organic base such as for example, L-Arginine, ethanolamine, betaine, benzathine, morpholine and the like.

Compounds of Formulae I-III and their salts can be in the form of a solvate, which is included within the scope of the present invention. Such solvates include, for example, hydrates, alcoholates and the like.

With respect to the present invention reference to a compound or compounds, is intended to encompass that compound in each of its possible isomeric forms and mixtures thereof unless the particular isomeric form is referred to specifically. Compounds according to the present invention may exist in different polymorphic forms. Although not explicitly indicated in the above formula, such forms are intended to be included within the scope of the present invention.

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2H$ (or D) in place of protium $^1H$ (or H) or use of $^{13}C$ enriched material in place of $^{12}C$ and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diasteroisomeric isomers, chromatographic separation may be employed.

Compound names were generated with software such as Chem Bio Draw Ultra version 14.0.

In general, characterization of the compounds is performed using NMR spectra, which were recorded on 300 and/or 600 MHz Varian and acquired at room temperature. Chemical shifts are given in ppm referenced either to internal TMS or to the solvent signal.

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures.

Usually the compounds of the invention were purified by column chromatography (Auto-column) on an Teledyne-ISCO CombiFlash with a silica column, unless noted otherwise.

The following abbreviations are used in the examples:

$nBu_4NOH$: tetrabutylammonium hydroxide; DMF: dimethylformamide; MPLC: medium-pressure liquid chromatography; MeOH: methanol; $NaCNBH_3$: Sodium cyanoborohydride; NaOMe: sodium methoxide; EtOH: ethanol: $CDCl_3$: deuterated chloroform: $NaBH_4$: sodium borohydride: $Na_2SO_4$: sodium sulfate; HCl: hydrochloric acid; $Et_2O$: ether: $NH_4Cl$: ammonium chloride; DIBAL-H: diisobutylaluminum hydride; $K_2CO_3$: potassium carbonate; $CH_2Cl_2$: dichloromethane; CuI: copper iodide; NMO: N-Methylmorpholine oxide; $SiO_2$: silica gel.

Example 1: Synthesis of 3-((S)-1-(1H-imidazol-4-yl)ethyl)-2-methylbenzyl (2S,3R)-2-ethyl-4-hydroxy-3-((1-methyl-1H-imidazol-5-yl)methyl)butanoate

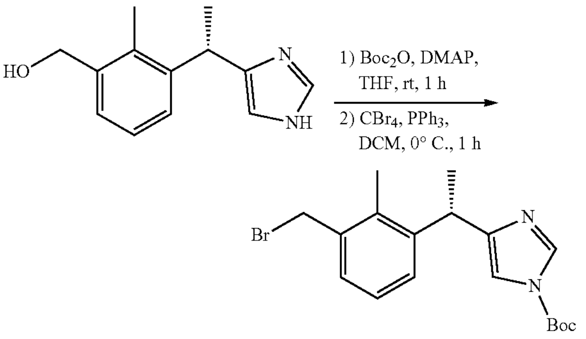

tert-Butyl (S)-4-(1-(3-(bromomethyl)-2-methylphenyl) ethyl)-1H-imidazole-1-carboxylate: (S)-(3-(1-(1H-Imidazol-4-yl)ethyl)-2-methylphenyl)methanol (300 mg, 1.39 mmol), BOC anhydride (364 mg, 2.09 mmol) and DMAP (256 mg, 2.09 mmol) were mixed in THF (20 mL) at 0 C and stirred at room temperature for 1 hour. The reaction mixture was diluted with EtOAc and then washed with water, dried ($Na_2SO_4$) and concentrated. The crude BOC protected compound was then mixed with $CBr_4$ (693 mg, 2.09 mmol) and $PPh_3$ (729 mg, 2.78 mmol) in DCM (30 mL) at 0 C and the resulting reaction mixture was then stirred at 0° C. for 1 hour and was allowed to warm to room temperature. The reaction mixture was diluted with EtOAc and then washed with water, dried ($Na_2SO_4$) and concentrated. Chromatography (3/1 EtOAc/hex) then concentration with rotatory evaporator gave 270 mg (51% yield) of the desired title compound over the two steps.

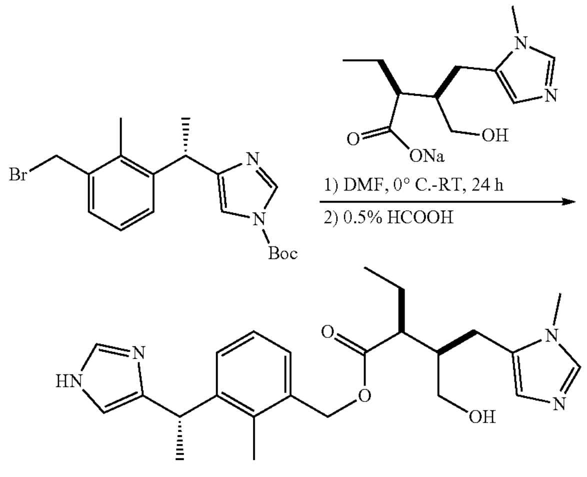

3-((S)-1-(1H-Imidazol-4-yl)ethyl)-2-methylbenzyl (2S, 3R)-2-ethyl-4-hydroxy-3-((1-methyl-1H-imidazol-5-yl)methyl)butanoate: tert-Butyl (S)-4-(1-(3-(bromomethyl)-2-methylphenyl)ethyl)-1H-imidazole-1-carboxylate (prepared in the previous step, 270 mg, 0.71 mmol) and sodium (2S,3R)-2-ethyl-4-hydroxy-3-((1-methyl-1H-imidazol-5-yl)methyl)-butanoate (176 mg, 0.71 mmol) were mixed in DMF (10 mL) and stirred at 0 C for 24 hours. The reaction mixture was diluted with EtOAc and then washed with water, dried ($Na_2SO_4$) and concentrated. 80 mg of this crude intermediate compound was mixed with 0.1 formic acid and stirred for 4 hours, then concentrated. Reverse chromatography (0.1% formic acid) then concentration with rotatory evaporator and lyophilization gave the desired title compound (11.9 mg) as a solid. Spectroscopic data: $^1$H NMR (400 MHz, MeOD) δ 8.18 (d, J=1.0 Hz, 1H), 8.08 (s, 1H), 7.29 (t, J=5.6 Hz, 1H), 7.17 (t, J=7.6 Hz, 1H), 7.11-7.04 (m, 2H), 6.94 (s, 1H), 5.22 (s, 2H), 4.53 (q, J=7.2 Hz, 1H), 3.62 (s, 3H), 3.60-3.56 (m, 1H), 3.34-3.32 (m, 1H), 2.81-2.75 (m, 1H), 2.60-2.49 (m, 2H), 2.41 (s, 3H), 2.07-2.00 (m, 1H), 1.76-1.63 (m, 2H), 1.57 (d, J=6.0 Hz, 3H), 0.89 (t, J=7.2 Hz, 3H).

Example 2: Synthesis of 3-((S)-1-(1H-imidazol-4-yl)ethyl)-2-methylbenzyl (2S,3R)-4-acetoxy-2-ethyl-3-((1-methyl-1H-imidazol-5-yl)methyl)butanoate

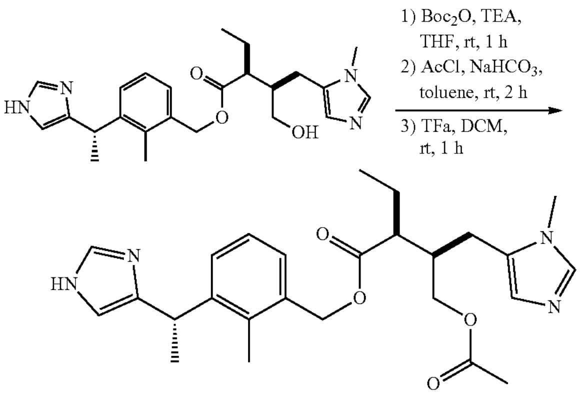

3-((S)-1-(1H-Imidazol-4-yl)ethyl)-2-methylbenzyl (2S, 3R)-4-acetoxy-2-ethyl-3-((1-methyl-1H-imidazol-5-yl)methyl)butanoate: 3-((S)-1-(1H-imidazol-4-yl)ethyl)-2-methylbenzyl (2S,3R)-2-ethyl-4-hydroxy-3-((1-methyl-1H-imidazol-5-yl)methyl)butanoate (prepared above, 200 mg, 0.47 mmol), BOC anhydride (124 mg, 0.71 mmol) and TEA (102 mg, 1.00 mmol) were mixed in THF (10 mL) at 0 C and stirred for 1 hour at room temperature. The reaction mixture was diluted with EtOAc and then washed with water, dried ($Na_2SO_4$) and concentrated. Chromatography (3/1 EtOAc/hex) then concentration with rotatory evaporator gave the desired intermediate. This intermediate (90 mg) was then mixed with AcCl (40 mg, 0.51 mmol) and $NaHCO_3$ (43 mg, 0.51 mmol) in toluene (5 mL) at 0 C then warmed to room temperature and stirred for 2 hours and concentrated. The reaction mixture was diluted with EtOAc and then washed with water, dried ($Na_2SO_4$) and concentrated. This crude BOC protected intermediate (60 mg) was mixed with TFA in DCM (5 mL) and stirred for 1 hour, then concentrated. Chromatography (EtOAc) then concentration with rotatory evaporator gave the desired title compound. Spectroscopic data: $^1$H NMR (400 MHz, $CD_3OD$) δ 8.15 (d, J=9.6 Hz, 1H), 7.96 (d, J=2.8 Hz, 1H), 7.32-7.27 (m, 1H), 7.18 (t, J=7.6 Hz, 1H), 7.10 (d, J=7.6 Hz, 1H), 7.04 (s, 1H), 6.90 (d, J=8.0 Hz, 1H), 5.23 (d, J=2.0 Hz, 2H), 4.57-4.46 (m, 1H), 4.07 (t, J=4.1 Hz, 2H), 3.68-3.48 (m, 3H), 2.80-2.62 (m, 2H), 2.548-2.49 (m, 1H), 2.47-2.35 (m, 3H), 2.38-2.29 (m, 1H), 2.01 (d, J=9.6 Hz, 3H), 1.76-1.66 (m, 2H), 1.64-1.56 (m, 3H), 0.90 (t, J=7.6 Hz, 3H).

Example 3: Synthesis of (((2S,3R)-4-acetoxy-2-ethyl-3-((1-methyl-1H-imidazol-5-yl)methyl)butanoyl)oxy)methyl 2-((4-bromo-1H-benzo[d]imidazol-5-yl)amino)-4,5-dihydro-1H-imidazole-1-carboxylate

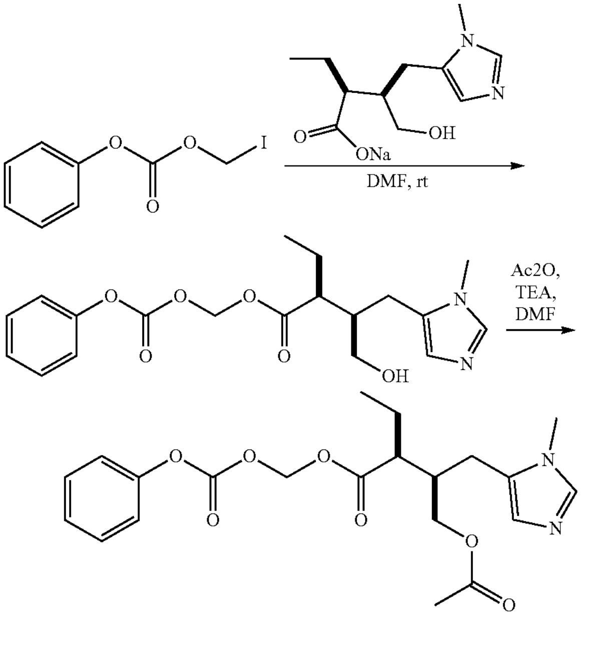

((Phenoxycarbonyl)oxy)methyl (2S,3R)-4-acetoxy-2-ethyl-3-((1-methyl-1H-imidazol-5-yl)methyl)butanoate: Iodomethyl phenyl carbonate (300 mg, 1.08 mmol) and sodium (2S,3R)-2-ethyl-4-hydroxy-3-((1-methyl-1H-imidazol-5-yl)methyl)butanoate (268 mg, 1.08 mmol) were mixed in DMF (7 mL) and stirred at room temperature for 4 hours.

The reaction mixture was diluted with EtOAc and then washed with water, dried ($Na_2SO_4$) and concentrated. The crude intermediate ((phenoxycarbonyl)oxy)methyl (2S,3R)-2-ethyl-4-hydroxy-3-((1-methyl-1H-imidazol-5-yl)methyl) butanoate was then mixed with $Ac_2O$ (204 mg, 2.00 mmol) and TEA (202 mg, 2.00 mmol) in DMF (5 mL) at 0 C then stirred for 4 hours. The reaction mixture was diluted with EtOAc and then washed with water, dried ($Na_2SO_4$) and concentrated. This crude ((phenoxycarbonyl)oxy)methyl (2S,3R)-4-acetoxy-2-ethyl-3-((1-methyl-1H-imidazol-5-yl) methyl)butanoate was used in the next step without further purification.

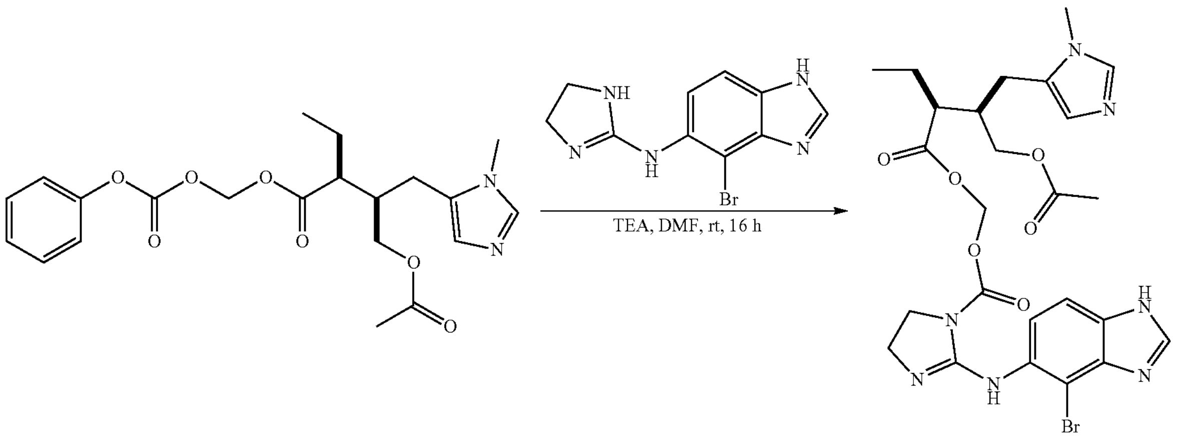

(((2S,3R)-4-Acetoxy-2-ethyl-3-((1-methyl-1H-imidazol-5-yl)methyl)butanoyl)oxy)-methyl 2-((4-bromo-1H-benzo[d]imidazol-5-yl)amino)-4,5-dihydro-1H-imidazole-1-carboxylate: ((Phenoxycarbonyl)oxy)methyl (2S,3R)-4-acetoxy-2-ethyl-3-((1-methyl-1H-imidazol-5-yl)methyl) butanoate (prepared above, crude, 90 mg, 0.22 mmol), 4-bromo-N-(4,5-dihydro-1H-imidazol-2-yl)-1H-benzo[d] imidazol-5-amine (92 mg, 0.33 mmol) and TEA (45 mg, 0.44 mmol) were mixed in DMF (5 mL) at 0 C then stirred at room temperature for 16 hours. The reaction mixture was diluted with EtOAc and then washed with water, dried ($Na_2SO_4$) and concentrated. Chromatography (0.5/4.5/95 $NH_4OH$/MeOH/EtOAc) then concentration with rotatory evaporator gave the desired title compound. Spectroscopic data: $^1H$ NMR (400 MHz, DMSO-$d_6$) δ 9.65 (s, 1H), 8.54 (d, J=8.8 Hz, 1H), 8.22 (d, J=26.4 Hz, 1H), 7.49 (s, 2H), 6.65 (s, 2H), 5.92-5.84 (m, 2H), 3.96 (s, 1H), 3.80-3.72 (m, 5H), 3.51 (s, 3H), 2.61 (d, J=5.3 Hz, 2H), 2.27 (s, 1H), 1.99-1.97 (m, 4H), 1.65-1.60 (m, 2H), 0.87 (t, J=2.0 Hz 3H).

Example 4: Synthesis of (((2S,3R)-2-ethyl-4-hydroxy-3-((1-methyl-1H-imidazol-5-yl)methyl)butanoyl)oxy)methyl 2-((4-bromo-1H-benzo[d]imidazol-5-yl)amino)-4,5-dihydro-1H-imidazole-1-carboxylate

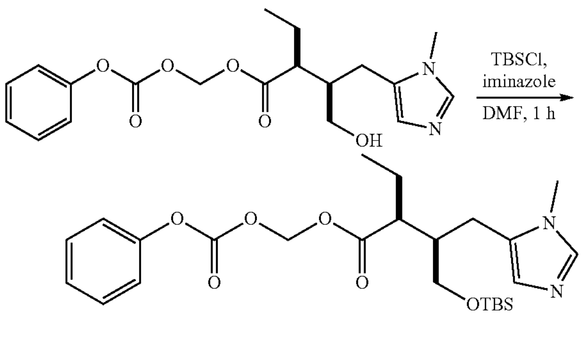

((Phenoxycarbonyl)oxy)methyl (2S,3R)-4-((tert-butyldimethylsilyl)oxy)-2-ethyl-3-((1-methyl-1H-imidazol-5-yl) methyl)butanoate: ((Phenoxycarbonyl)oxy)methyl (2S,3R)-2-ethyl-4-hydroxy-3-((1-methyl-1H-imidazol-5-yl)methyl) butanoate (crude, prepared above, 300 mg), TBSCl (181 mg, 1.20 mmol) and imidazole (109 mg, 1.60 mmol) were mixed in DMF (10 mL) at 0 C and stirred for 1 hour. The reaction mixture was diluted with EtOAc and then washed with water, dried ($Na_2SO_4$) and concentrated to give the desired crude title compound which was used in the subsequent transformations without further purification.

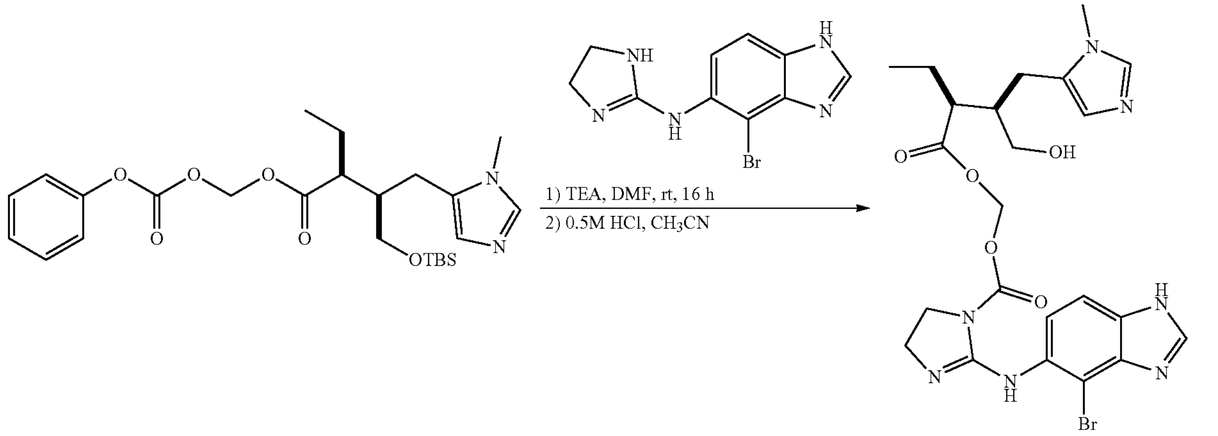

(((2S,3R)-2-Ethyl-4-hydroxy-3-((1-methyl-1H-imidazol-5-yl)methyl)butanoyl)oxy)-methyl 2-((4-bromo-1H-benzo [d]imidazol-5-yl)amino)-4,5-dihydro-1H-imidazole-1-carboxylate: ((phenoxycarbonyl)oxy)methyl (2S,3R)-4-((tert-butyldimethyl-silyl)-oxy)-2-ethyl-3-((1-methyl-1H-imidazol-5-yl)methyl)butanoate (prepared above, crude, 100 mg, 0.20 mmol), 4-bromo-N-(4,5-dihydro-1H-imidazol-2-yl)-1H-benzo[d]imidazol-5-amine (84 mg, 0.30 mmol) and TEA (41 mg, 0.40 mmol) were mixed in DMF (5 mL) at 0 C then stirred at room temperature for 16 hours. The reaction mixture was diluted with EtOAc and then washed with water, dried ($Na_2SO_4$) and concentrated. This crude intermediate compound was mixed with 0.5M HCl (1 mL) in acetonitrile (5 mL) and stirred for 4 hours, then concentrated. Reverse chromatography (0.1% formic acid) then concentration with rotatory evaporator and lyophilization gave the desired title compound. Spectroscopic data: $^1H$ NMR (400 MHz, DMSO-$d_6$) δ 9.65 (s, 1H), 8.54 (d, J=8.8 Hz, 1H), 8.22 (d, J=26.4 Hz, 1H), 7.49 (s, 2H), 6.65 (s, 2H), 5.92-5.84 (m, 2H), 3.96 (s, 1H), 3.80-3.72 (m, 3H), 3.51 (s, 3H), 3.33-3.19 (m, 2H), 2.61 (d, J=5.3 Hz, 2H), 2.27 (s, 1H), 1.99-1.97 (m, 1H), 1.65-1.60 (m, 2H), 0.87 (t, J=2.0 Hz 3H).

Example 5: Synthesis of (((2S,3R)-2-ethyl-4-hydroxy-3-((1-methyl-1H-imidazol-5-yl)methyl)butanoyl)oxy)methyl 2-((5-bromoquinoxalin-6-yl) amino)-4,5-dihydro-1H-imidazole-1-carboxylate

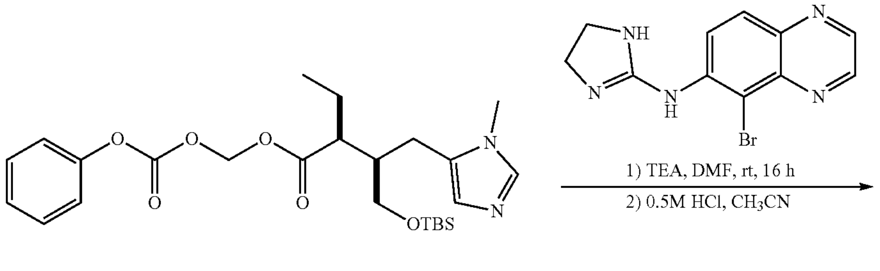

-continued

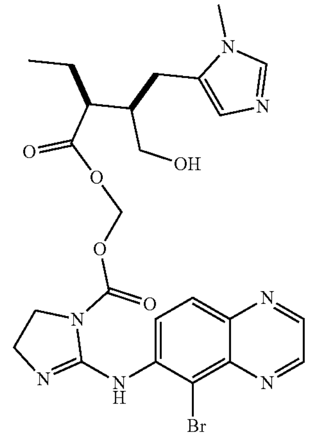

(((2S,3R)-2-Ethyl-4-hydroxy-3-((1-methyl-1H-imidazol-5-yl)methyl)butanoyl)-oxy)methyl 2-((5-bromoquinoxalin-6-yl)amino)-4,5-dihydro-1H-imidazole-1-carboxylate: ((Phenoxycarbonyl)oxy)methyl (2S,3R)-4-((tert-butyldimethylsilyl)oxy)-2-ethyl-3-((1-methyl-1H-imidazol-5-yl)methyl)butanoate (prepared above, crude, 100 mg, 0.20 mmol), 5-bromo-N-(4,5-dihydro-1H-imidazol-2-yl)quinoxalin-6-amine (88 mg, 0.30 mmol) and TEA (41 mg, 0.40 mmol) were mixed in DMF (5 mL) at 0 C then stirred at room temperature for 16 hours. The reaction mixture was diluted with EtOAc and then washed with water, dried ($Na_2SO_4$) and concentrated. This crude intermediate compound was mixed with 0.5M HCl (1 mL) in acetonitrile (5 mL) and stirred for 4 hours, then concentrated. Reverse chromatography (0.1% formic acid) then concentration with rotatory evaporator and lyophilization gave the desired title compound. Spectroscopic data: $^1$H NMR (400 MHz, $CD_3OD$) δ 8.85 (dd, J=38.4, 1.6 Hz, 3H), 8.04 (d, J=9.2 Hz, 1H), 7.53 (s, 1H), 6.76 (s, 1H), 6.01 (d, J=6.0 Hz, 1H), 5.92 (d, J=6.0 Hz, 1H), 3.97 (s, 2H), 3.77 (s, 1H), 3.64 (d, J=3.2 Hz, 3H), 3.33-3.22 (m, 2H), 2.75 (d, J=7.2 Hz, 2H), 2.65-2.54 (m, 1H), 2.47-2.35 (m, 1H), 1.82-1.68 (m, 2H), 0.98 (t, J=7.2 Hz, 3H).

Example 6: Synthesis of (((2S,3R)-4-acetoxy-2-ethyl-3-((1-methyl-1H-imidazol-5-yl)methyl)butanoyl)oxy)methyl 2-((5-bromoquinoxalin-6-yl)amino)-4,5-dihydro-1H-imidazole-1-carboxylate

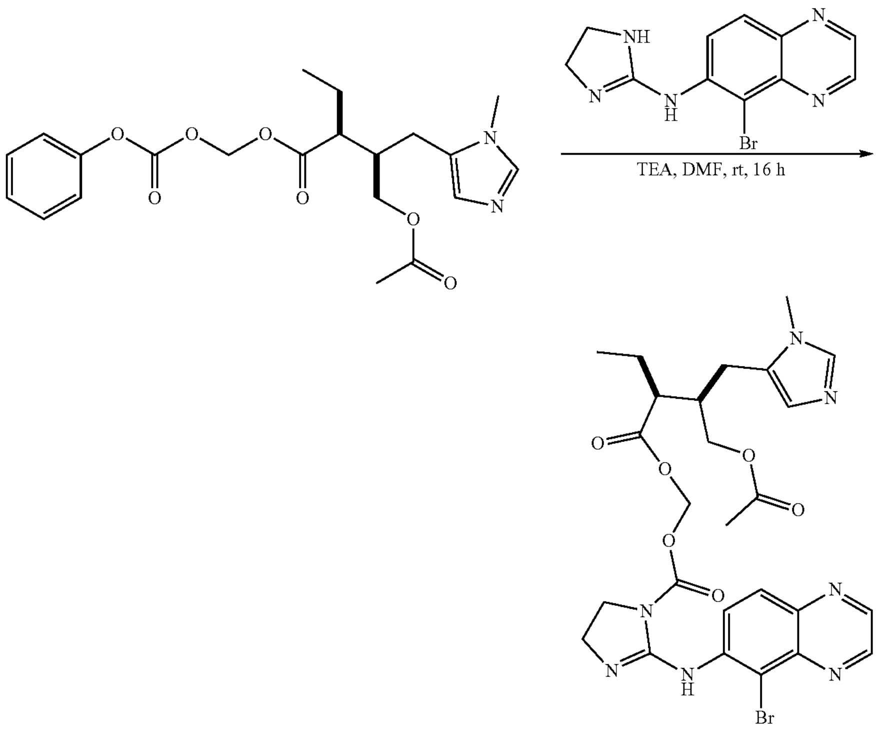

(((2S,3R)-4-Acetoxy-2-ethyl-3-((1-methyl-1H-imidazol-5-yl)methyl)butanoyl)oxy)methyl 2-((5-bromoquinoxalin-6-yl)amino)-4,5-dihydro-1H-imidazole-1-carboxylate:

((Phenoxycarbonyl)oxy)methyl (2S,3R)-4-acetoxy-2-ethyl-3-((1-methyl-1H-imidazol-5-yl)methyl)butanoate (prepared above, crude, 95 mg, 0.23 mmol), 5-bromo-N-(4,5-dihydro-1H-imidazol-2-yl)quinoxalin-6-amine (99 mg, 0.35 mmol) and TEA (47 mg, 0.46 mmol) were mixed in DMF (5 mL) at 0 C then stirred at room temperature for 16 hours. The reaction mixture was diluted with EtOAc and then washed with water, dried ($Na_2SO_4$) and concentrated. Chromatography (0.5/4.5/95 $NH_4OH$/MeOH/EtOAc) then concentration with rotatory evaporator gave the desired title compound. Spectroscopic data: $^1H$ NMR (400 MHz, $CD_3OD$) δ 8.85 (dd, J=38.4, 1.6 Hz, 3H), 8.04 (d, J=9.2 Hz, 1H), 7.53 (s, 1H), 6.76 (s, 1H), 6.01 (d, J=6.0 Hz, 1H), 5.92 (d, J=6.0 Hz, 1H), 4.18-4.04 (m, 2H), 3.97 (s, 2H), 3.77 (s, 1H), 3.64 (d, J=3.2 Hz, 3H), 2.75 (d, J=7.2 Hz, 2H), 2.65-2.54 (m, 1H), 2.47-2.35 (m, 1H), 2.03 (s, 3H), 1.82-1.68 (m, 2H), 0.98 (t, J=7.2 Hz, 3H).

Example 7: Synthesis of (2R,3S)-3-(((3-((S)-1-(1H-imidazol-4-yl)ethyl)-2-methylbenzyl)oxy)carbonyl)-2-((1-methyl-1H-imidazol-5-yl)methyl)pentyl decanoate

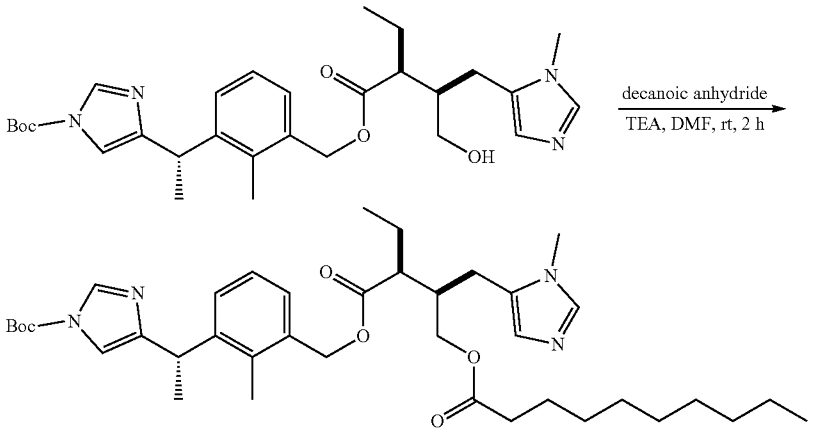

tert-Butyl 4-((S)-1-(3-((((2S,3R)-4-(decanoyloxy)-2-ethyl-3-((1-methyl-1H-imidazol-5-yl)methyl)butanoyl)oxy)methyl)-2-methylphenyl)ethyl)-1H-imidazole-1-carboxylate To a solution of tert-butyl 4-((S)-1-(3-((((2S,3R)-2-ethyl-4-hydroxy-3-((1-methyl-1H-imidazol-5-yl)methyl)butanoyl)oxy)methyl)-2-methylphenyl)ethyl)-1H-imidazole-1-carboxylate (prepared above, 100 mg, 0.18 mmol) in DMF (5 mL) was added triethylamine (55 mg, 1.14 mmol)) and decanoic anhydride (31 mg, 0.85 mmol). The mixture was stirred at 25 C for 2 h. LCMS showed the reaction worked well. The mixture was diluted with EtOAc (50 mL) and washed with water (3x30 mL). The organic layer was concentrated in vacuum to afford the titled tert-butyl 4-((S)-1-(3-((((2S,3R)-4-(decanoyloxy)-2-ethyl-3-((1-methyl-1H-imidazol-5-yl)methyl)butanoyl)oxy)methyl)-2-methylphenyl)ethyl)-1H-imidazole-1-carboxylate (100 mg, 78% yield) as a light yellow solid. LCMS (ESI) calcd. $C_{39}H_{58}N_4O_6^+$ $[M+H]^+$ m/z 679.44, found 679.4.

(2R,3S)-3-(((3-((S)-1-(1H-imidazol-4-yl)ethyl)-2-methylbenzyl)oxy)carbonyl)-2-((1-methyl-1H-imidazol-5-yl)methyl)pentyl decanoate

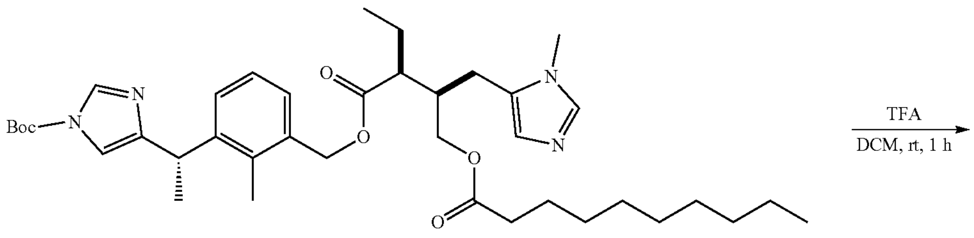

-continued

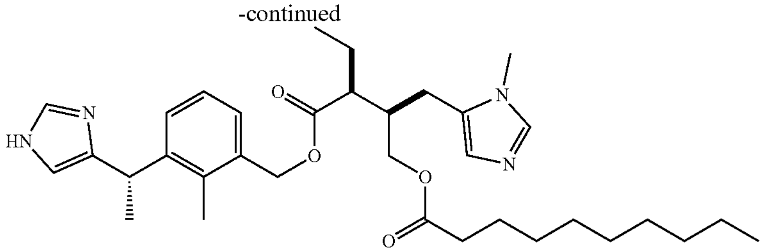

To a solution of tert-butyl 4-((S)-1-(3-((((2S,3R)-4-(decanoyloxy)-2-ethyl-3-((1-methyl-1H-imidazol-5-yl)methyl)butanoyl)oxy)methyl)-2-methylphenyl)ethyl)-1H-imidazole-1-carboxylate 2 (100 mg, 0.15 mmol) in $CH_2Cl_2$ (10 mL) was added TFA (2 mL) at 25 C. The mixture was stirred at 25 C for 1 h. LCMS showed the reaction worked well. The pH value was adjusted with sat. aq. $NaHCO_3$ to 8. The mixture was extracted with $CH_2Cl_2$ (2×50 mL). The organic layers were concentrated and purified by prep-HPLC (FA 0.1%) to afford the titled (2R,3S)-3-(((3-((S)-1-(1H-imidazol-4-yl)ethyl)-2-methyl-benzyl)oxy)carbonyl)-2-((1-methyl-1H-imidazol-5-yl)methyl)pentyl decanoate (78.5 mg, 85% yield) as a white solid. Prep-HPLC conditions: Chromatographic columns: Xtimate 10 um C18 250×30 mm. Mobile Phase: ACN—$H_2O$ (0.1% FA); Gradient: 17-27. $^1$H NMR (400 MHz, $CD_3OD$) δ 8.69 (d, J=23.2 Hz, 2H), 7.33 (dd, J=13.2, 5.6 Hz, 3H), 7.21 (t, J=7.6 Hz, 1H), 7.06 (d, J=6.8 Hz, 1H), 5.31 (d, J=12.4 Hz, 1H), 5.23 (d, J=12.4 Hz, 1H), 4.62 (d, J=7.2 Hz, 1H), 4.15-4.09 (m, 2H), 3.80 (s, 3H), 2.80 (d, J=7.6 Hz, 2H), 2.61 (dd, J=14.1, 7.2 Hz, 2H), 2.44 (s, 3H), 2.33 (t, J=7.6 Hz, 2H), 1.77-1.70 (m, 2H), 1.64 (d, J=7.2 Hz, 5H), 1.31 (s, 12H), 0.90 (d, J=7.2 Hz, 6H). LCMS (ESI) calcd for $C_{34}H_{50}N_4O_4^+$ [M+H]$^+$ m/z 579.38, found 579.4.

Example 8: Synthesis of (2R,3S)-3-(((3-((S)-1-(1H-imidazol-4-yl)ethyl)-2-methylbenzyl)oxy)carbonyl)-2-((1-methyl-1H-imidazol-5-yl)methyl)pentyl hexanoate tert-Butyl tert-butyl 4-((S)-1-(3-((((2S,3R)-2-ethyl-4-(hexanoyloxy)-3-((1-methyl-1H-imidazol-5-yl)methyl)butanoyl)oxy)methyl)-2-methylphenyl)ethyl)-1H-imidazole-1 carboxylate

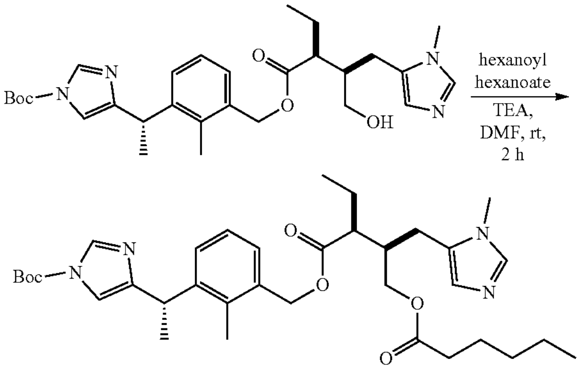

To a solution of tert-butyl 4-((S)-1-(3-((((2S,3R)-2-ethyl-4-hydroxy-3-((1-methyl-1H-imidazol-5-yl)methyl)butanoyl)oxy)methyl)-2-methylphenyl)ethyl)-1H-imidazole-1-carboxylate (prepared above, 100 mg, 0.18 mmol) in DMF (5 mL) was added triethylamine (55 mg, 1.14 mmol) and hexanoyl hexanoate (31 mg, 0.85 mmol). The mixture was stirred at 25 C for 2 h. LCMS showed the reaction worked well. The mixture was diluted with EtOAc (50 mL) and washed with water (3×30 mL). The organic layer was concentrated in vacuum to afford the desired tert-butyl 4-((S)-1-(3-((((2S,3R)-2-ethyl-4-(hexanoyloxy)-3-((1-methyl-1H-imidazol-5-yl)methyl)butanoyl)oxy)methyl)-2-methylphenyl)ethyl)-1H-imidazole-1-carboxylate (50 mg, 39% yield) as a light yellow solid. LCMS (ESI) calcd $C_{39}H_{58}N_4O_6^+$ [M+H]$^+$ m/z 622.37, found 623.3.

(2R,3S)-3-(((3-((S)-1-(1H-imidazol-4-yl)ethyl)-2-methylbenzyl)oxy)carbonyl)-2-((1-methyl-1H-imidazol-5-yl)methyl)pentyl hexanoate

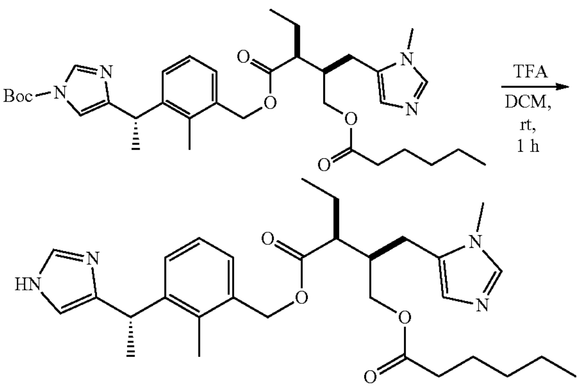

To a solution of tert-butyl 4-((S)-1-(3-((((2S,3R)-2-ethyl-4-(hexanoyloxy)-3-((1-methyl-1H-imidazol-5-yl)methyl)butanoyl)oxy)methyl)-2-methylphenyl)ethyl)-1H-imidazole-1-carboxylate (prepared above, 50 mg, 0.08 mmol) in $CH_2Cl_2$ (10 mL) was added TFA (2 mL) at 25° C. The mixture was stirred at 25 C for 1 h. LCMS showed the reaction worked well. The pH value was adjusted with sat. aq. $NaHCO_3$ to 8. The mixture was extracted with $CH_2Cl_2$ (2×50 mL). The organic layers were concentrated and purified by prep-HPLC (FA 0.1%) to afford the desired (2R,3S)-3-(((3-((S)-1-(1H-imidazol-4-yl)ethyl)-2-methylbenzyl)oxy)carbonyl)-2-((1-methyl-1H-imidazol-5-yl)methyl)pentyl hexanoate (6.7 mg, 13.8% yield) as a white solid. Prep-HPLC conditions: Chromatographic columns: Xtimate 10 um C18 250×30 mm. Mobile Phase: ACN—$H_2O$ (0.1% FA). Gradient: 17-27. $^1$H NMR (400 MHz, $CD_3OD$) δ 7.54 (d, J=15.2 Hz, 2H), 7.24 (s, 1H), 7.15 (d, J=6.4 Hz, 2H), 6.70 (s, 2H), 5.22 (s, 2H), 4.44 (d, J=6.8 Hz, 1H), 4.11-4.01 (m, 2H), 3.55-3.45 (m, 3H), 2.68-2.46 (m, 4H), 2.39 (s, 3H), 2.30 (t, J=7.6 Hz, 2H), 1.77-1.66 (m, 2H), 1.65-1.45 (m, 5H), 1.32 (s, 4H), 0.91 (dt, J=12.0, 7.2 Hz, 6H). LCMS (ESI) calcd for $C_{30}H_{42}N_4O_4^+$ [M+H]$^+$ m/z 523.32, found 523.3.

Example 9: Synthesis of (2R,3S)-3-ethyl-4-({3-[(1S)-1-(1H-imidazol-4-yl)ethyl]-2-methylphenyl}methoxy)-2-[(3-methylimidazol-4-yl)methyl]-4-oxobutyl (9Z)-octadec-9-enoate
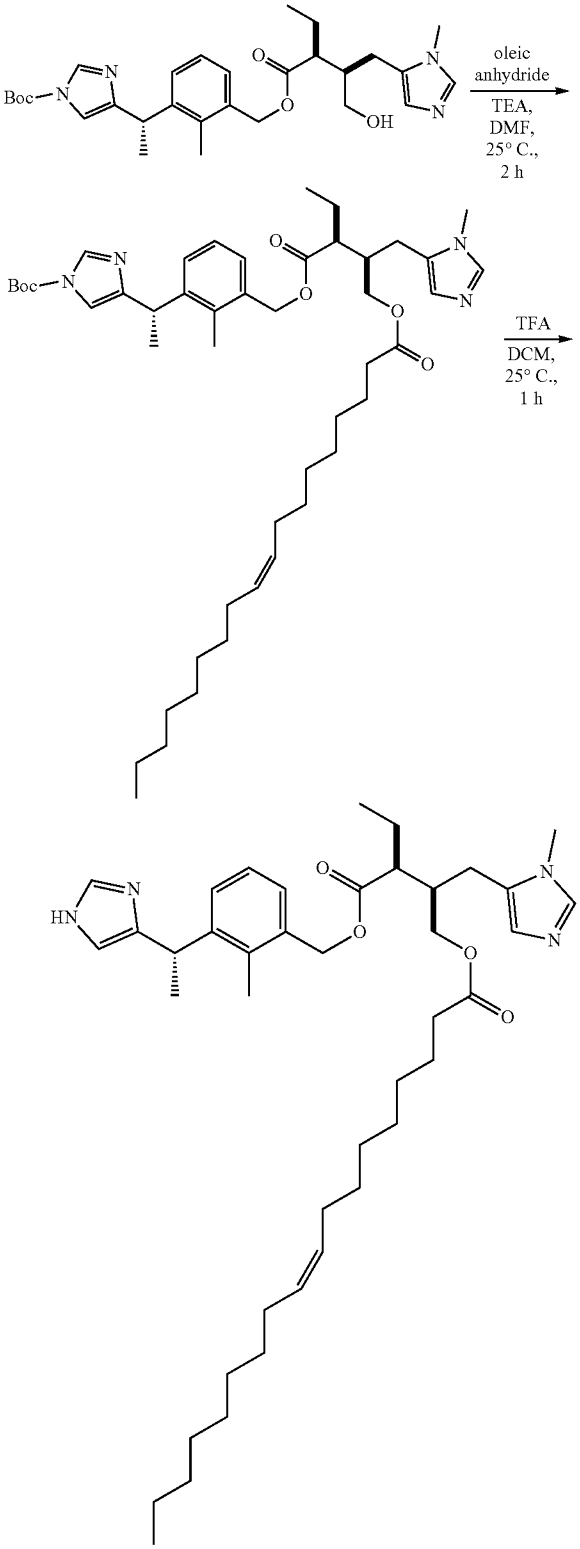
(2R,3S)-4-({3-[(1S)-1-[1-(tert-butyl-3}-oxy)imidazol-4-yl]ethyl]-2-methylphenyl}-methoxy)-3-ethyl-2-[(3-methylimidazol-4-yl)methyl]-4-oxobutyl (9Z)-octadec-9-enoate
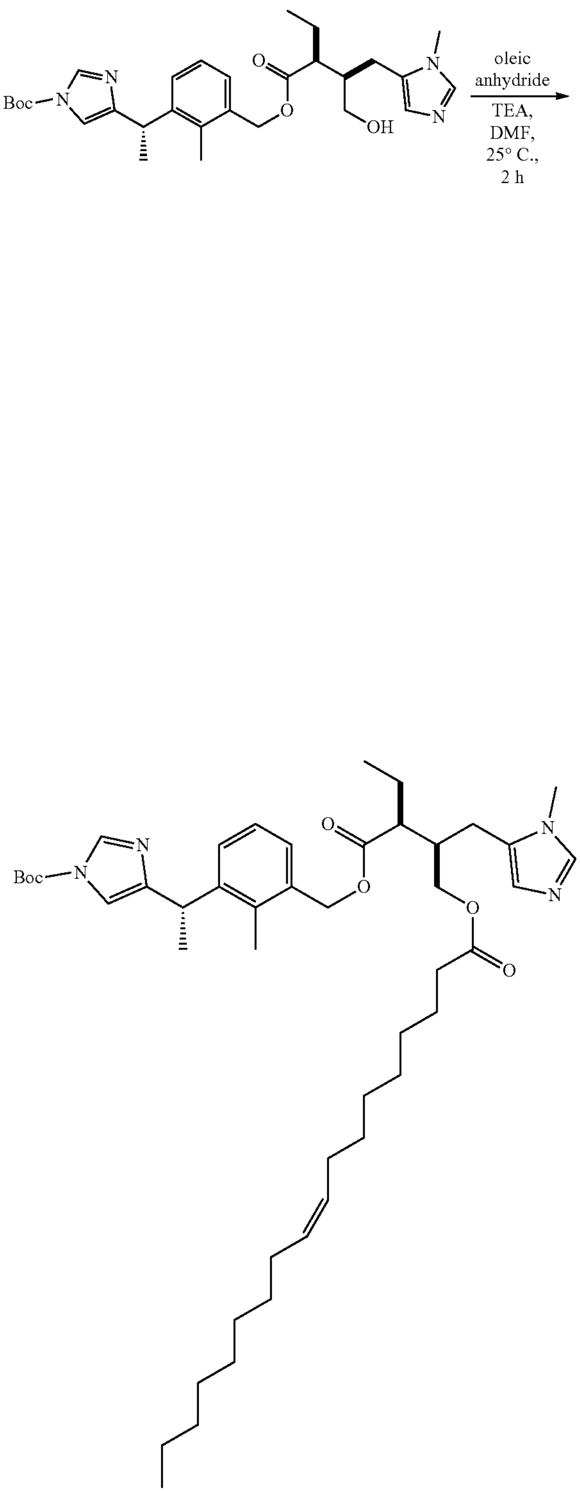

To a solution of tert-butyl 4-((S)-1-(3-((((2S,3R)-2-ethyl-4-hydroxy-3-((1-methyl-1H-imidazol-5-yl)methyl)butanoyl)oxy)methyl)-2-methylphenyl)ethyl)-1H-imidazole-1-carboxylate (prepared above, 100 mg, 0.19 mmol) in DMF (5 ml) was added TEA (12 mg, 0.11 mmol) and oleic anhydride (205 mg, 0.38 mmol) at 25 C. The mixture was stirred at 25 C for 2 h. LCMS showed the reaction was well. The mixture was diluted with EtOAc (50 mL) and washed with water (3×30 mL). The organic layer was concentrated in vacuum to afford the desired (2R,3S)-4-({3-[(1S)-1-[1-(tert-butyl-3}-oxy)imidazol-4-yl]ethyl]-2-methylphenyl}methoxy)-3-ethyl-2-[(3-methylimidazol-4-yl)methyl]-4-oxobutyl (9Z)-octadec-9-enoate (100 mg, 76% yield) as a yellow solid. LCMS (ESI) calcd for $C_{47}H_{72}N_4O_6^+$ $[(M-100)/2+H]^+$ m/z 345.3, found 345.3.

(2R,3S)-3-ethyl-4-({3-[(1S)-1-(1H-imidazol-4-yl)ethyl]-2-methylphenyl}methoxy)-2-[(3-methylimidazol-4-yl)methyl]-4-oxobutyl (9Z)-octadec-9-enoate

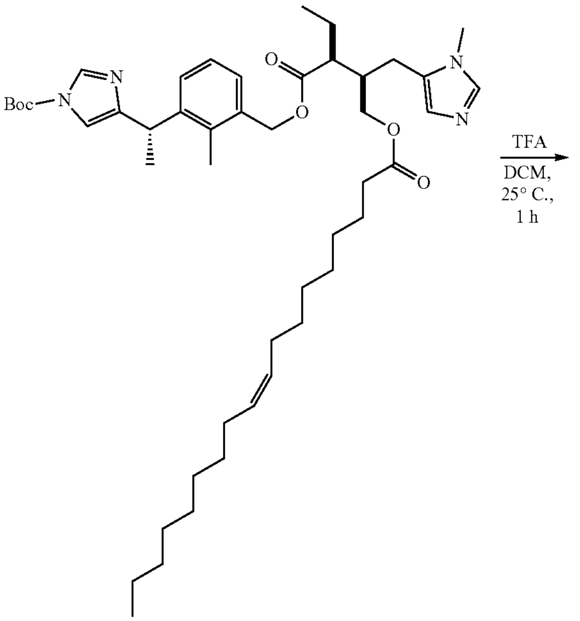

-continued

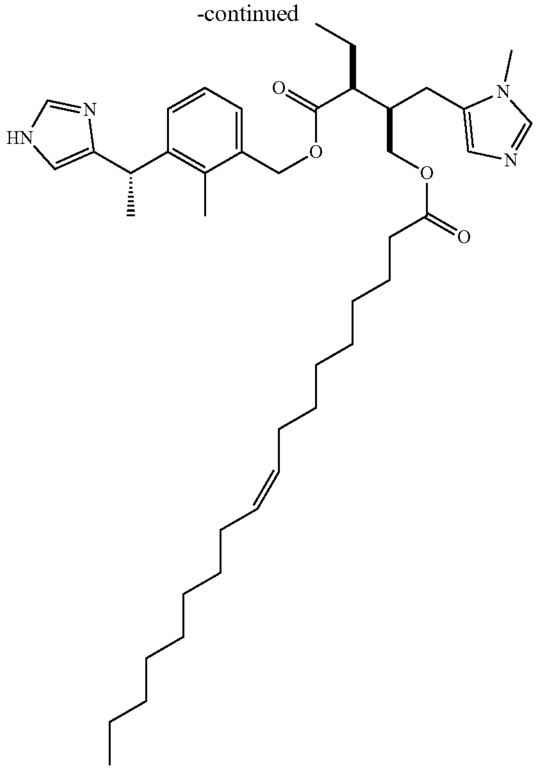

To a solution of tert-butyl 4-[(1S)-1-[3-({[(2S,3R)-2-ethyl-3-[(3-methylimidazol-4-yl)methyl]-4-[(9Z)-octadec-9-enoyloxy]butanoyl]oxy}methyl)-2-methylphenyl]ethyl]imidazole-1-carboxylate (prepared above, 100 mg, 0.12 mmol) in DCM (5 ml) was added TFA (1 mL) at 25 C. The mixture was stirred at 25 C for 16 h. LCMS showed the reaction was well. The pH value was adjusted with aq. $NaHCO_3$ to 8. The mixture was extracted with DCM (2×50 mL). The organic layer was concentrated and purified by prep-HPLC (FA) to afford (2R,3S)-3-ethyl-4-({3-[(1S)-1-(1H-imidazol-4-yl)ethyl]-2-methylphenyl}methoxy)-2-[(3-methylimidazol-4-yl)methyl]-4-oxobutyl (9Z)-octadec-9-enoate (22 mg, 25% yield) as a white solid. Prep-HPLC conditions: Chromatographic columns: Xbridge 5u C18 150×19 mm. Mobile Phase: ACN—$H_2O$ (0.1% FA). Gradient: 40-50. $^1H$ NMR (400 MHz, $CDCl_3$) δ 7.90 (s, 1H), 7.23 (d, J=6.8 Hz, 1H), 7.16-7.09 (m, 2H), 7.01 (d, J=7.2 Hz, 1H), 6.96 (s, 1H), 6.30 (s, 1H), 5.38-5.30 (m, 2H), 5.20 (d, J=12.0 Hz, 1H), 5.07 (d, J=12.0 Hz, 1H), 4.46-4.41 (m, 1H), 4.08-3.97 (m, 2H), 3.40 (s, 3H), 2.57 (dd, J=15.2, 6.8 Hz, 1H), 2.52-2.39 (m, 2H), 2.38-2.27 (m, 6H), 2.03-1.97 (m, 4H), 1.68-1.54 (m, 7H), 1.28 (d, J=16.0 Hz, 20H), 0.93-0.86 (m, 6H). LCMS (ESI) calcd for $C_{42}H_{64}N_4O_4^+$ $[M+H]^+$ m/z 689.49, found 689.3.

Example 10: Synthesis of (2R,3S)-3-ethyl-4-({3-[(1S)-1-(1H-imidazol-4-yl)ethyl]-2-methylphenyl}methoxy)-2-[(3-methylimidazol-4-yl)methyl]-4-oxobutyl (9Z,12Z)-octadeca-9,12-dienoate (2R,3S)-4-({3-[(1S)-1-[1-(tert-butoxycarbonyl)imidazol-4-yl]ethyl]-2-methylphenyl}-methoxy)-3-ethyl-2-[(3-methylimidazol-4-yl)methyl]-4-oxobutyl (9Z,12Z)-octadeca-9,12-dienoate

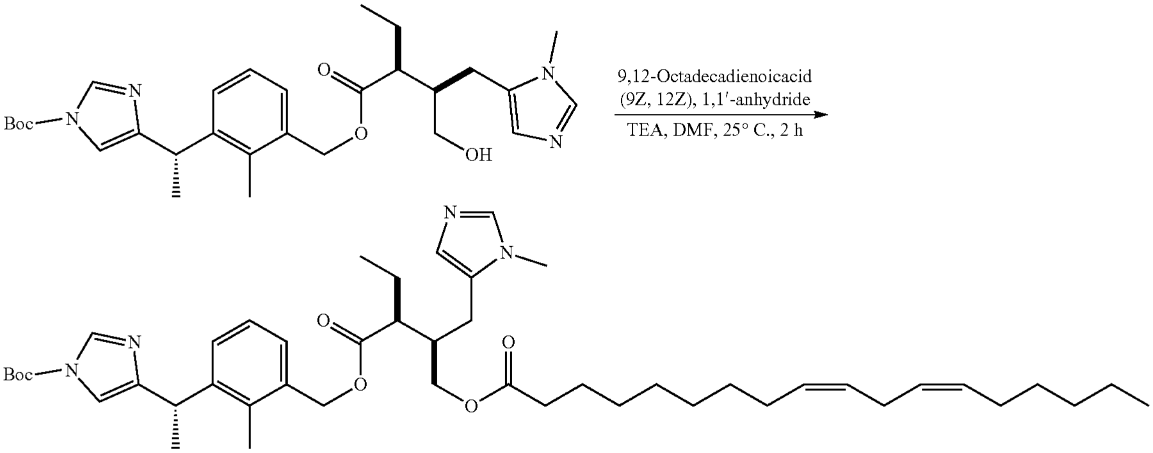

To a solution of {3-[(1S)-1-[1-(tert-butoxycarbonyl)imidazol-4-yl]ethyl]-2-methylphenyl}methyl (2S,3R)-2-ethyl-4-hydroxy-3-[(3-methylimidazol-4-yl)methyl]-butanoate (prepared above, 100 mg, 0.19 mmol) in DMF (5 ml) was added TEA (12 mg, 0.11 mmol) and 9,12-Octadecadienoicacid (9Z,12Z)-,1,1'-anhydride (205 mg, 0.38 mmol) at 25 C. The mixture was stirred at 25 C for 2 h. LCMS showed the reaction was well. The mixture was diluted with EtOAc (50 mL) and washed with water (3×30 mL). The organic layer was concentrated in vacuum to afford the desired tert-butyl 4-((S)-1-(3-((((2S,3R)-2-ethyl-4-(1-methyl-1H-imidazol-5-yl)-3-((((9Z,12Z)-octadeca-9,12-dienoyl)oxy)methyl)butanoyl)oxy)methyl)-2-methylphenyl)ethyl)-1H-imidazole-1-carboxylate (100 mg, 76% yield) as a light yellow solid. LCMS (ESI) calcd for $C_{47}H_{70}N_4O_6^+$ [(M−100)/2+H]$^+$ m/z 344.3, found 344.3.

(2R,3S)-3-Ethyl-4-({3-[(1S)-1-(1H-imidazol-4-yl)ethyl]-2-methylphenyl}methoxy)-2-[(3-methylimidazol-4-yl)methyl]-4-oxobutyl (9Z,12Z)-octadeca-9,12-dienoate

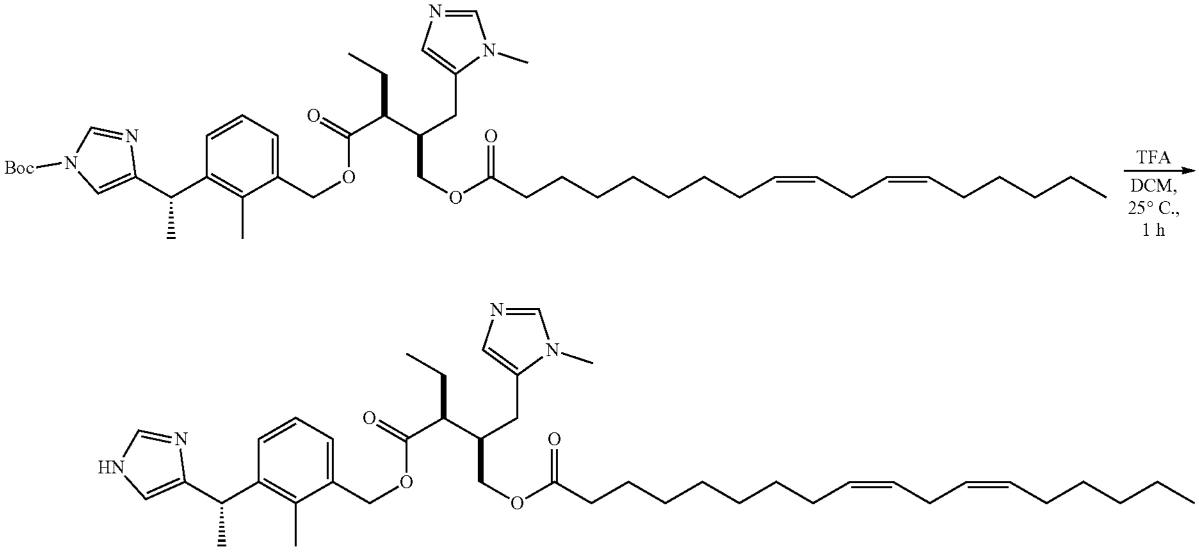

To a solution of tert-butyl 4-((S)-1-(3-((((2S,3R)-2-ethyl-4-(1-methyl-1H-imidazol-5-yl)-3-((((9Z,12Z)-octadeca-9,12-dienoyl)oxy)methyl)butanoyl)oxy)methyl)-2-methylphenyl)ethyl)-1H-imidazole-1-carboxylate (prepared above, 100 mg, 0.13 mmol) in $CH_2Cl_2$ (5 mL) was added TFA (1 mL) at 25 C. The mixture was stirred at 25 C for 1 h. LCMS showed the reaction was well. The pH value was adjusted with aq. $NaHCO_3$ to 8. The mixture was extracted with $CH_2Cl_2$ (2×50 mL). The organic layer was concentrated and purified by prep-HPLC (FA 0.1%) to afford the desired (2R,3S)-3-ethyl-4-({3-[(1S)-1-(1H-imidazol-4-yl)ethyl]-2-methylphenyl}methoxy)-2-[(3-methylimidazol-4-yl)methyl]-4-oxobutyl (9Z,12Z)-octadeca-9,12-dienoate (29 mg, 33% yield) as a white solid. Prep-HPLC conditions: Chromatographic columns: Xbridge 5u C18 150×19 mm. Mobile Phase: ACN—$H_2O$ (0.1% FA). Gradient: 16-26. $^1H$ NMR (400 MHz, MeOD) δ 7.72 (s, 1H), 7.58 (s, 1H), 7.17-7.10 (m, 1H), 7.06-6.99 (m, 2H), 6.73 (s, 1H), 6.66 (s, 1H), 5.30-5.17 (m, 4H), 5.10 (s, 2H), 4.39-4.34 (m, 1H), 3.98-3.90 (m, 2H), 3.41 (s, 3H), 2.68-2.62 (m, 2H), 2.56-2.47 (m, 2H), 2.41-2.36 (m, 1H), 2.27 (s, 3H), 2.18-2.15 (m, 4H), 2.00-1.91 (m, 4H), 1.59-1.56 (m, 1H), 1.48-1.45 (m, 5H), 1.27-1.21 (m, 14H), 0.81-0.76 (m, 6H). LCMS (ESI) calcd for $C_{42}H_{62}N_4O_4^+$ [M+H]$^+$ m/z 687.48, found 687.4.

Example 11: Synthesis of (2R,3S)-4-[({2-[(5-bromoquinoxalin-6-yl)amino]-4,5-dihydroimidazol-1-yl}carbonyloxy)methoxy]-3-ethyl-2-[(3-methylimidazol-4-yl)methyl]-4-oxobutyl (9Z)-octadec-9-enoate (2R,3S)-3-ethyl-2-[(3-methylimidazol-4-yl)methyl]-4-oxo-4-(sodiooxy)butyl (9Z)-octadec-9-enoate

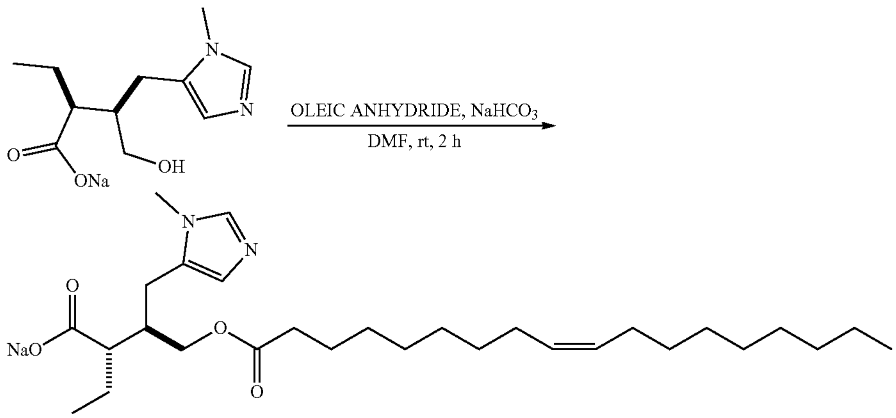

To a solution of (2R,3S)-3-ethyl-2-[(3-methylimidazol-4-yl)methyl]-4-oxo-4-(sodiooxy)butyl (9Z)-octadec-9-enoate (prepared above, 500 mg, 2.01 mmol) in DMF (15 mL) was added $NaHCO_3$ (508 mg, 6.04 mmol) and oleic anhydride (1102 mg, 2.01 mmol). The reaction mixture was stirred at 25 C for 2 h. LCMS showed the reaction worked well. The reaction mixture was washed with water (50 mL) and extracted with EtOAc (3×50 mL). The combined organic layer was washed with brine (50 mL) and dried over anhydrous $Na_2SO_4$. The aqueous phase was freeze-dried to give the desire (2R,3S)-3-ethyl-2-[(3-methylimidazol-4-yl)methyl]-4-oxo-4-(sodiooxy)butyl (9Z)-octadec-9-enoate (600 mg, 52% yield) as a white solid, which was used to the next step without further purification. LCMS (ESI) calcd for $C_{29}H_{49}N_2NaO_4$ [M−15+H]$^+$ m/z 491.4, found 491.4.

((2R,3S)-3-ethyl-2-[(3-methylimidazol-4-yl)methyl]-4-oxo-4-{[(phenoxycarbonyl)oxy]methoxy}butyl (9Z)-octadec-9-enoate

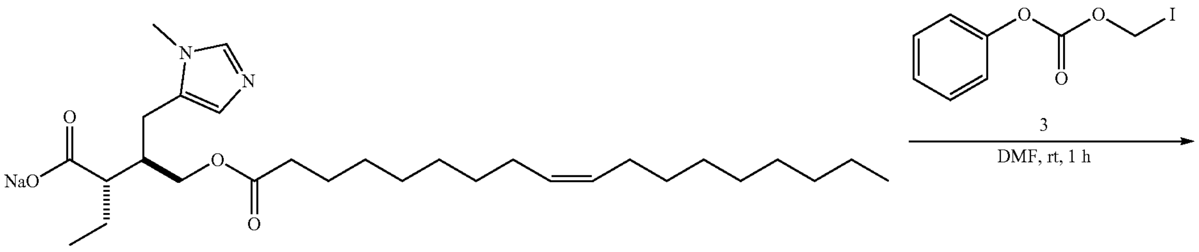

-continued

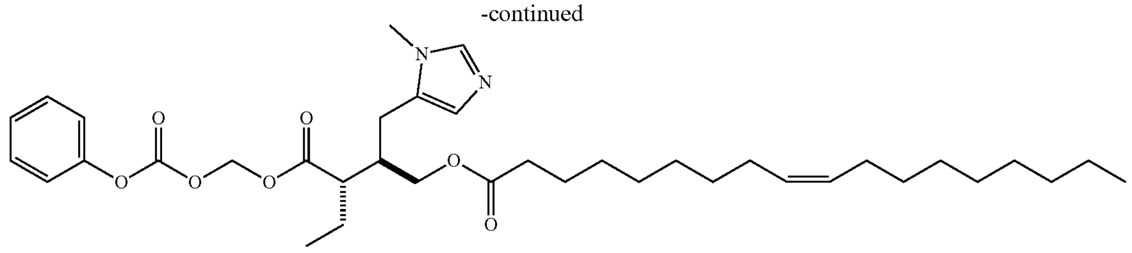

To a solution of (2R,3S)-3-ethyl-2-[(3-methylimidazol-4-yl)methyl]-4-oxo-4-(sodiooxy)butyl (9Z)-octadec-9-enoate (prepared above, 600 mg, 1.1703 mmol) in DMF (15 mL) was added iodomethyl phenyl carbonate (325 mg, 1.1703 mmol). The reaction mixture was stirred at 25 C for 1 h. LCMS showed the reaction worked well. The reaction mixture was poured into water (50 mL) and extracted with EtOAc (3×50 mL). The combined organic layer dried over anhydrous $Na_2SO_4$ and concentrated in vacuum to give the titled ((2R,3S)-3-ethyl-2-[(3-methylimidazol-4-yl)methyl]-4-oxo-4-{[(phenoxycarbonyl)-oxy]methoxy}butyl (9Z)-octadec-9-enoate (600 mg, 40% yield) as a yellow oil, which was used to the next step without further purification. LCMS (ESI) calcd for $C_{37}H_{56}N_2O_7$ $[M+H]^+$ m/z 641.4, found 641.5.

(2R,3S)-4-[({2-[(5-bromoquinoxalin-6-yl)amino]-4,5-dihydroimidazol-1-yl}carbonyl-oxy)methoxy]-3-ethyl-2-[(3-methylimidazol-4-yl)methyl]-4-oxobutyl (9Z)-octadec-9-enoate To a solution of (2R,3S)-3-ethyl-2-[(3-methylimidazol-4-yl)methyl]-4-oxo-4-{[(phenoxycarbonyl)oxy]methoxy}butyl (9Z)-octadec-9-enoate (prepared above, 600 mg, 0.94 mmol) in DMF (15 mL) was added 5-bromo-N-(4,5-dihydro-1H-imidazol-2-yl)quinoxalin-6-amine (274 mg, 0.94 mmol) and TEA (190 mg, 1.87 mmol). The reaction mixture was stirred at 25 C for 2 h. LCMS showed the reaction worked well. The reaction mixture was poured into water (50 mL) and extracted with EtOAc (3×50 mL). The combined organic layer dried over anhydrous $Na_2SO_4$ and concentrated in vacuum. The residue was purified by silica gel column chromatography to give the product as a crude. The crude was then further purified by prep-HPLC (ACN—$H_2O$ (0.1% FA)) to afford the desired (2R,3S)-4-[({2-[(5-bromoquinoxalin-6-yl)amino]-4,5-dihydroimidazol-1-yl}carbonyloxy)methoxy]-3-ethyl-2-[(3-methylimidazol-4-yl)methyl]-4-oxobutyl (9Z)-octadec-9-enoate (100 mg, 11% yield) as a yellow solid. Chromatographic columns: -Xbridge-C18 150×19 mm, 5 um. Mobile Phase: ACN—$H_2O$ (0.1% FA). Gradient: 20-60. $^1H$ NMR (400 MHz, $CDCl_3$) δ 9.24 (d, J=9.2 Hz, 1H), 8.90 (d, J=1.6 Hz, 1H), 8.77 (d, J=1.6 Hz, 1H), 8.08 (d, J=9.2 Hz, 1 H), 7.71 (s, 1H), 6.91 (s, 1H), 5.93 (dd, J=10.4, 5.6 Hz, 2H), 5.36-5.29 (m, 2H), 4.07 (s, 1H), 3.93 (d, J=9.6 Hz, 2H), 3.64 (s, 3H), 2.68 (t, J=7.2 Hz, 2H), 2.58 (td, J=8.4, 5.2 Hz, 1H), 2.31-2.19 (m, 6H), 1.99 (d, J=6.0 Hz, 4H), 1.69 (dd, J=12.4, 7.2 Hz, 2H), 1.62-1.56 (m, 2H), 1.26 (s, 20H), 0.95 (t, J=7.2 Hz, 3H), 0.88 (d, J=6.4 Hz, 3H). LCMS (ESI) calcd for $C_{42}H_{60}BrN_7O_6$ $[M+H]^+$ m/z 838.4, found 838.3.

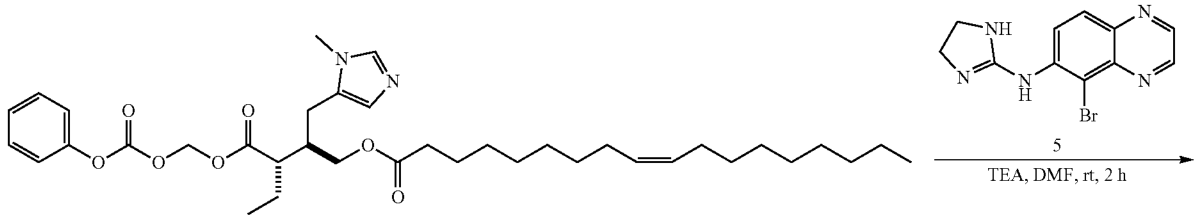

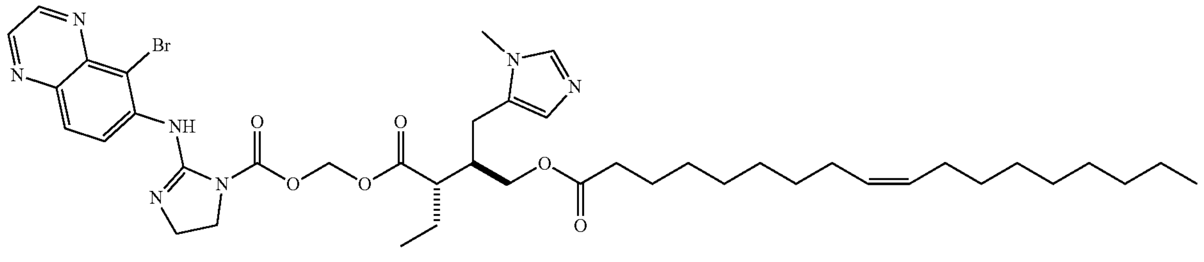

Example 12: Synthesis of (2R,3S)-4-[({2-[(5-bromoquinoxalin-6-yl)amino]-4,5-dihydroimidazol-1-yl}carbonyloxy)methoxy]-3-ethyl-2-[(3-methylimidazol-4-yl)methyl]-4-oxobutyl decanoate

(2R,3S)-3-ethyl-2-[(3-methylimidazol-4-yl)methyl]-5-oxo-5-(oxosodio)pentyl decanoate

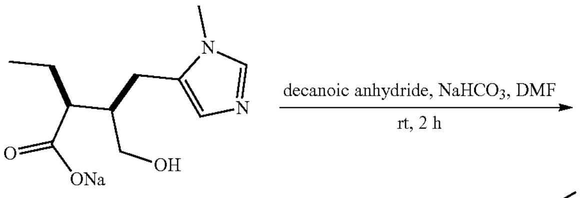

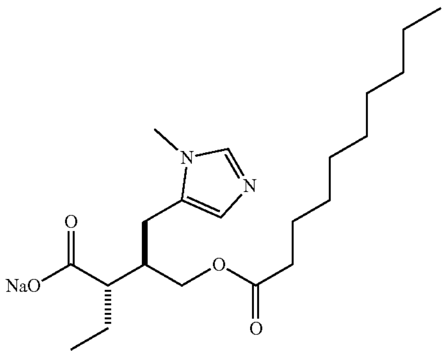

To a solution of sodium (2S,3R)-2-ethyl-4-hydroxy-3-[(3-methylimidazol-4-yl)methyl]butanoate (prepared above, 800 mg, 3.22 mol) in DMF (15 mL) was added $NaHCO_3$ (812 mg, 9.67 mmol) and DECANOIC ANHYDRIDE (1157 mg, 3.54 mmol). The reaction mixture was stirred at 25 C for 20 min. LCMS showed the reaction worked well. The residue was washed with water (50 mL) and extracted with EtOAc (3×100 mL). The combined organic layer was washed with brine (50 mL) and dried over anhydrous $Na_2SO_4$. The aqueous phase was freeze-dried to give the titled (2R,3S)-3-ethyl-2-[(3-methylimidazol-4-yl)methyl]-5-oxo-5-(oxosodio)pentyl decanoate (800 mg, 53% yield) as a white solid, which was used to the next step without further purification. LCMS (ESI) calcd for $C_{21}H_{36}N_2O_4$ $[M+H]^+$ m/z 381.3, found 381.3.

(2R,3S)-3-Ethyl-2-[(3-methylimidazol-4-yl)methyl]-4-oxo-4-{[(phenoxycarbonyl)oxy]-methoxy}butyl decanoate

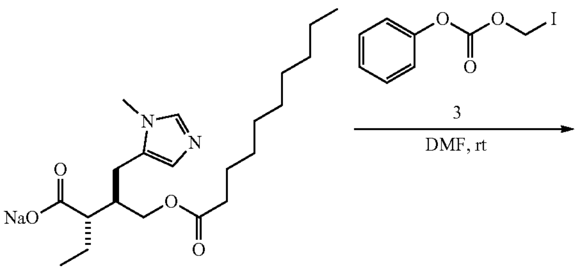

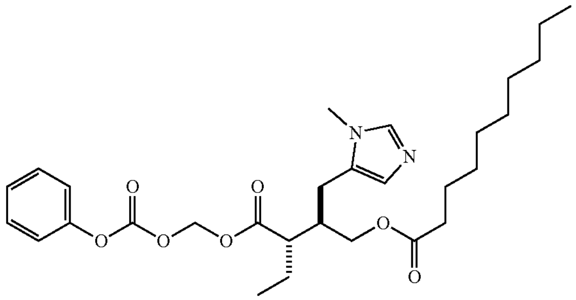

To a solution of (2R,3S)-3-ethyl-2-[(3-methylimidazol-4-yl)methyl]-4-oxo-4-(sodiooxy)butyl decanoate (prepared above, 800 mg, 1.99 mmol) in DMF (15 mL) was added iodomethyl phenyl carbonate (553 mg, 1.99 mmol). The reaction mixture was stirred at 25 C for 30 min. LCMS showed the reaction worked well. The reaction mixture was poured into water (50 mL) and extracted with EtOAc (3×50 mL). The combined organic layer dried over anhydrous $Na_2SO_4$ and concentrated in vacuum to give the desired (2R,3S)-3-ethyl-2-[(3-methylimidazol-4-yl)methyl]-4-oxo-4-{[(phenoxycarbonyl)oxy]methoxy}butyl decanoate (1.5 g, 50% purity, 71% yield) as a yellow solid. LCMS (ESI) calcd for $C_{29}H_{42}N_2O_7$ $[M+H]^+$ m/z 531.3, found 531.3.

(2R,3S)-4-[({2-[(5-Bromoquinoxalin-6-yl)amino]-4,5-dihydroimidazol-1-yl}carbonyloxy)methoxy]-3-ethyl-2-[(3-methylimidazol-4-yl)methyl]-4-oxobutyl decanoate

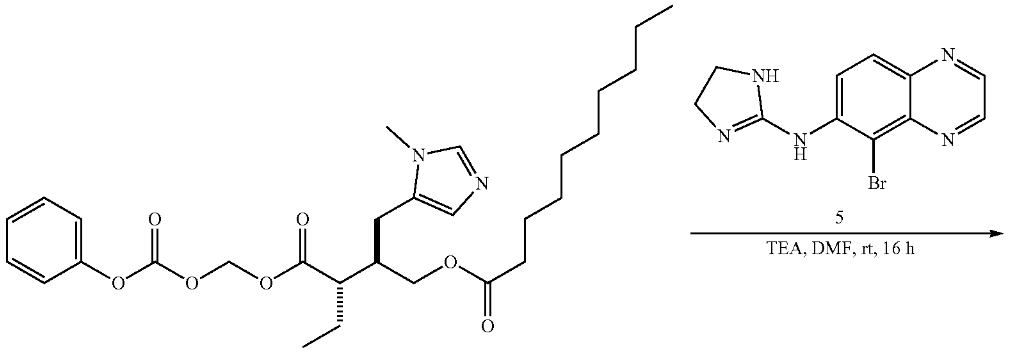

-continued

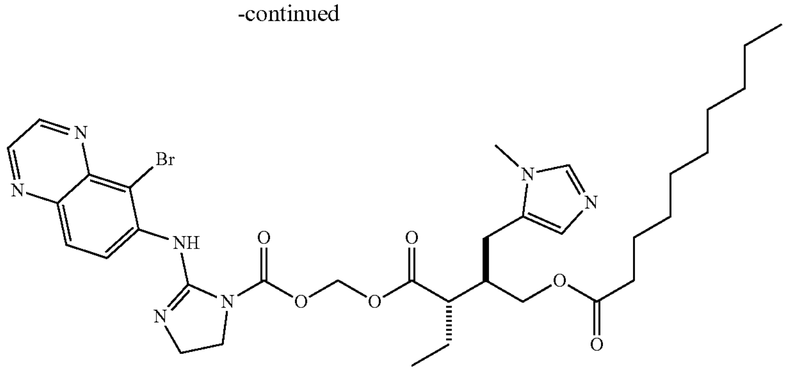

To a solution of (2R,3S)-3-ethyl-2-[(3-methylimidazol-4-yl)methyl]-4-oxo-4-{[(phenoxycarbonyl)oxy]methoxy}butyl decanoate (prepared above, 1.5 g, 2.80 mmol) in DMF (30 mL) was added 5-bromo-N-(4,5-dihydro-1H-imidazol-2-yl)quinoxalin-6-amine (0.82 g, 2.80 mmol) and TEA (0.57 g, 5.60 mmol). The reaction mixture was stirred at 25 C for 1 h. LCMS showed the reaction worked well. The reaction mixture was poured into water (50 mL) and extracted with EtOAc (3×100 mL). The combined organic layer dried over anhydrous $Na_2SO_4$ and concentrated in vacuum. The residue was purified by prep-HPLC (ACN—$H_2O$ (0.1% FA)) to afford the desired (2R,3S)-4-[({2-[(5-bromoquinoxalin-6-yl)amino]-4,5-dihydroimidazol-1-yl}carbonyloxy)methoxy]-3-ethyl-2-[(3-methylimidazol-4-yl)methyl]-4-oxobutyl decanoate (0.143 g, 11.4% yield) as a yellow solid. Chromatographic columns: Gemini-C18 150×21.2 mm, 5 um. Mobile Phase: ACN—$H_2O$ (0.1% FA). Gradient: 25-83. $^1H$ NMR (400 MHz, $CDCl_3$) δ 9.16 (d, J=9.2 Hz, 1H), 8.83 (d, J=1.6 Hz, 1H), 8.70 (d, J=1.6 Hz, 1H), 8.17 (s, 1H), 8.01 (d, J=9.2 Hz, 1H), 6.97 (s, 1H), 5.87 (dd, J=15.6, 5.6 Hz, 2H), 4.06-3.81 (m, 6H), 3.69 (s, 3H), 2.63 (s, 1H), 2.52 (d, J=4.8 Hz, 1H), 2.31-2.15 (m, 4H), 1.65 (dd, J=13.2, 6.0 Hz, 2H), 1.55-1.47 (m, 2H), 1.17 (d, J=10.4 Hz, 12H), 0.87 (dd, J=13.6, 6.4 Hz, 3H), 0.79 (t, J=6.8 Hz, 3H). LCMS (ESI) calcd for $C_{34}H_{46}BrN_7O_6$ $[M+H]^+$ m/z 728.3, found 728.3.

Example 13: Synthesis of ((2R,3S)-4-[({2-[(5-bromoquinoxalin-6-yl)amino]-4,5-dihydroimidazol-1-yl}carbonyloxy)methoxy]-3-ethyl-2-[(3-methylimidazol-4-yl)methyl]-4-oxobutyl (9Z,12Z)-octadeca-9,12-dienoate (2R,3S)-3-Ethyl-2-[(3-methylimidazol-4-yl)methyl]-4-oxo-4-(sodiooxy)butyl (9Z,12Z)-octadeca-9,12-dienoate

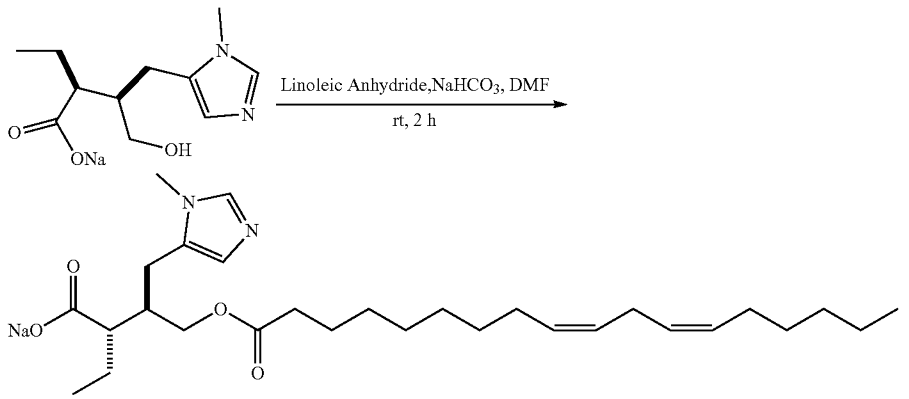

To a solution of (2R,3S)-3-ethyl-2-[(3-methylimidazol-4-yl)methyl]-4-oxo-4-(sodiooxy)butyl (9Z)-octadec-9-enoate (prepared above, 400 mg, 1.61 mmol) in DMF (10 mL) was added $NaHCO_3$ (406 mg, 4.83 mmol) and Linoleic Anhydride (875 mg, 1.61 mmol). The reaction mixture was stirred at 25 C for 2 h. LCMS showed the reaction worked well. The reaction mixture was washed with water (50 mL) and extracted with EtOAc (3×50 mL). The combined organic layer was washed with brine (50 mL) and dried over anhydrous $Na_2SO_4$. The aqueous phase was freeze-dried to give the desired (2R,3S)-3-ethyl-2-[(3-methylimidazol-4-yl)methyl]-4-oxo-4-(sodiooxy)butyl (9Z,12Z)-octadeca-9,12-dienoate (600 mg, 52% yield) as a white solid, which was used to the next step without further purification. LCMS (ESI) calcd for $C_{29}H_{47}N_2NaO_4$ $[M-15+H]^+$ m/z 489.4, found 489.4.

(2R,3S)-3-Ethyl-2-[(3-methylimidazol-4-yl)methyl]-4-oxo-4-{[(phenoxycarbonyl)-oxy]methoxy}butyl (9Z,12Z)-octadeca-9,12-dienoate

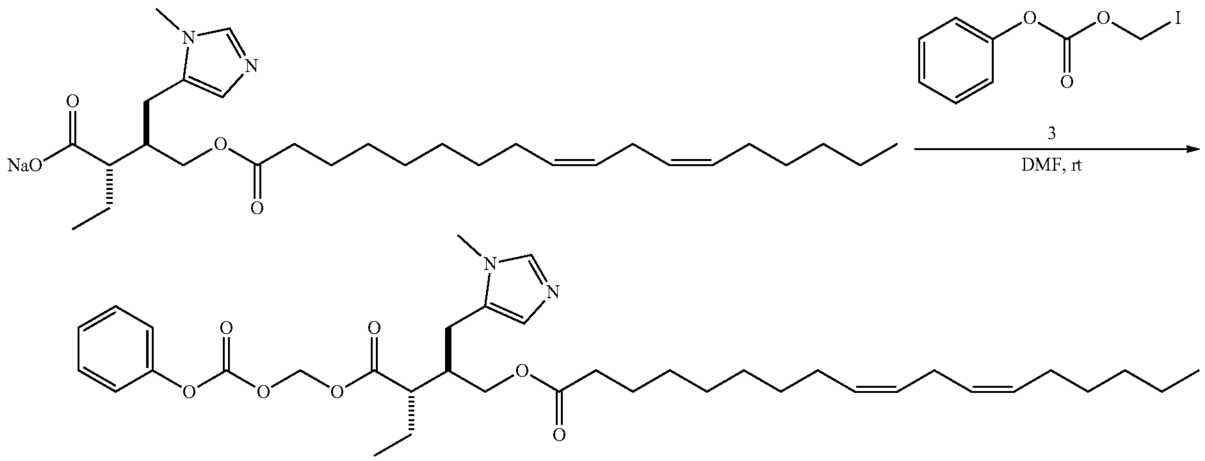

To a solution of (2R,3S)-3-ethyl-2-[(3-methylimidazol-4-yl)methyl]-4-oxo-4-(sodiooxy)butyl (9Z,12Z)-octadeca-9,12-dienoate (prepared above, 600 mg, 1.18 mmol) in DMF (20 ml) was added iodomethyl phenyl carbonate (326 mg, 1.18 mmol). The reaction mixture was stirred at 25 C for 2 h. LCMS showed the reaction worked well. The reaction mixture was poured into water (50 mL) and extracted with EtOAc (3×50 mL). The combined organic layer dried over anhydrous Na2SO4 and concentrated in vacuum to give the desired (2R,3S)-3-ethyl-2-[(3-methylimidazol-4-yl)methyl]-4-oxo-4-{[(phenoxycarbonyl)oxy]methoxy}butyl (9Z,12Z)-octadeca-9,12-dienoate (800 mg, 39% yield) as a yellow oil, which was used to the next step without further purification.

LCMS (ESI) calcd for $C_{37}H_{54}N_2O_7$ $[M+H]^+$ m/z 639.4, found 639.4.

((2R,3S)-4-[({2-[(5-bromoquinoxalin-6-yl)amino]-4,5-dihydroimidazol-1-yl}carbonyloxy)methoxy]-3-ethyl-2-[(3-methylimidazol-4-yl)methyl]-4-oxobutyl (9Z,12Z)-octadeca-9,12-dienoate

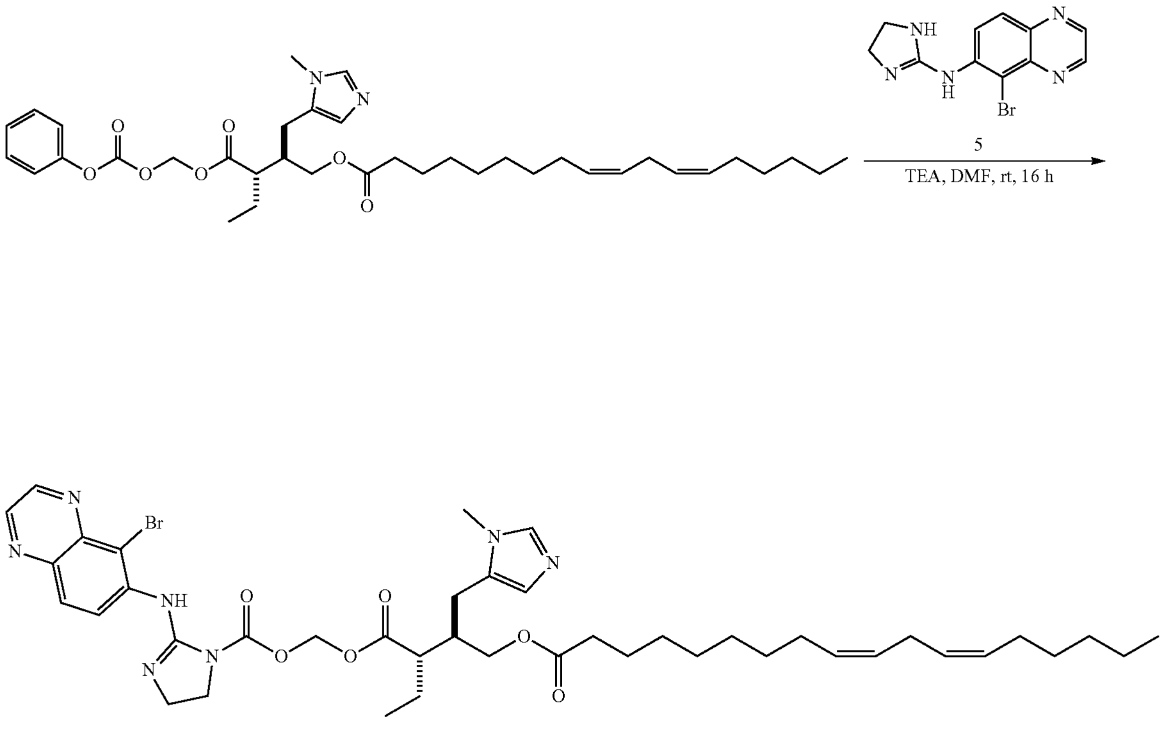

To a solution of (2R,3S)-3-ethyl-2-[(3-methylimidazol-4-yl)methyl]-4-oxo-4-{[(phenoxycarbonyl)oxy] methoxy}butyl (9Z,12Z)-octadeca-9,12-dienoate (prepared above, 800 mg, 1.25 mmol) in DMF (20 mL) was added 5-bromo-N-(4,5-dihydro-1H-imidazol-2-yl)quinoxalin-6-amine (366 mg, 1.25 mmol) and TEA (253 mg, 2.51 mmol). The reaction mixture was stirred at 25 C for 2 h. LCMS showed the reaction worked well. The reaction mixture was poured into water (50 mL) and extracted with EtOAc (3×50 mL). The combined organic layer dried over anhydrous $Na_2SO_4$ and concentrated in vacuum. The residue was purified by silica gel column chromatography to give the product as a crude. The crude was purified by prep-HPLC (ACN—$H_2O$ (0.1% TFA)) to afford the desired ((2R,3S)-4-[({2-[(5-bromoquinoxalin-6-yl)amino]-4,5-dihydroimidazol-1-yl}carbonyloxy)-methoxy]-3-ethyl-2-[(3-methylimidazol-4-yl)methyl]-4-oxobutyl (9Z,12Z)-octadeca-9,12-dienoate (49.7 mg, 4% yield) as a yellow solid. Chromatographic columns: -Xbridge-C18 150×19 mm, 5 um. Mobile Phase: ACN—$H_2O$ (0.1% FA). Gradient: 25-80, LCMS (ESI) calcd for $C_{42}H_{58}BrN_7O_6$ $[M+H]^+$ m/z 836.4, found 836.4. $^1H$ NMR (400 MHz, $CDCl_3$) δ 9.25 (s, 1H), 8.90 (d, J=1.6 Hz, 1H), 8.77 (d, J=1.6 Hz, 1H), 8.08 (d, J=9.2 Hz, 2H), 7.00 (s, 1H), 5.96-5.90 (m, 2H), 5.37-5.30 (m, 4H), 4.07 (d, J=4.4 Hz, 1H), 3.94 (dd, J=14.8, 6.0 Hz, 4H), 3.71 (s, 2H), 2.77-2.68 (m, 4H), 2.41 (d, J=7.6 Hz, 1H), 2.34-2.24 (m, 4H), 2.06-2.01 (m, 4H), 1.42-1.18 (m, 20H), 0.95 (t, J=7.2 Hz, 3H), 0.87 (d, J=6.8 Hz, 3H).

Example 14: Synthesis of 3-((S)-1-(1H-imidazol-4-yl)ethyl)-2-methylbenzyl (2S,3R)-2-ethyl-4-(1-methyl-1H-imidazol-5-yl)-3-((pivaloyloxy) methyl) butanoate tert-Butyl 4-((S)-1-(3-((((2S,3R)-2-ethyl-4-(1-methyl-1H-imidazol-5-yl)-3-((pivaloyloxy)methyl) butanoyl)oxy)methyl)-2-methylphenyl)ethyl)-1H-imidazole-1-carboxylate

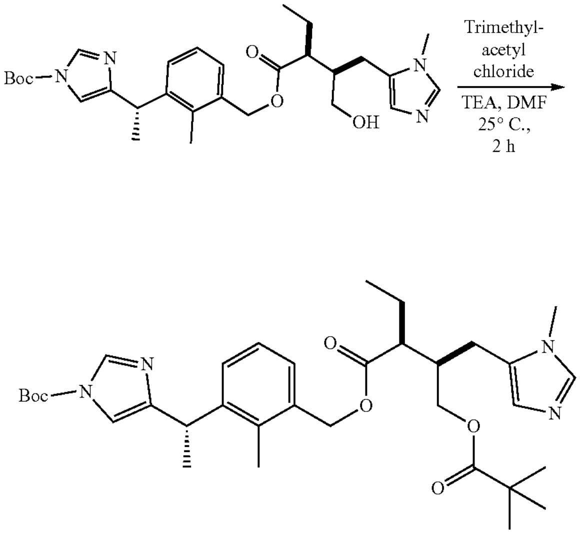

To a solution of {3-[(1S)-1-[1-(tert-butyl-oxy)imidazol-4-yl]ethyl]-2-methylphenyl}methyl (2S,3R)-2-ethyl-4-hydroxy-3-[(3-methylimidazol-4-yl)methyl]butanoate (prepared above, 300 mg, 0.57 mmol) in DMF (5 mL) was added triethylamine (173 mg, 1.71 mmol)) and 2,2-dimethylpropanoyl chloride (68 mg, 0.57 mmol). The mixture was stirred at 25 C for 2 h. LCMS showed the reaction worked well. The mixture was diluted with EtOAc (50 mL) and washed with water (3×30 mL). The organic layer was concentrated in vacuum to afford the desired tert-butyl 4-((S)-1-(3-((((2S,3R)-2-ethyl-4-(1-methyl-1H-imidazol-5-yl)-3-((pivaloyloxy)methyl)butanoyl)-oxy)methyl)-2-methylphenyl)ethyl)-1H-imidazole-1-carboxylate (150 mg, 68% yield) as a light yellow solid. LCMS (ESI) calcd $C_{34}H_{48}N_4O_6^+$ $[M+H]^+$ m/z 609.36, found 609.4.

3-((S)-1-(1H-Imidazol-4-yl)ethyl)-2-methylbenzyl (2S,3R)-2-ethyl-4-(1-methyl-1H-imidazol-5-yl)-3-((pivaloyloxy)methyl)butanoate

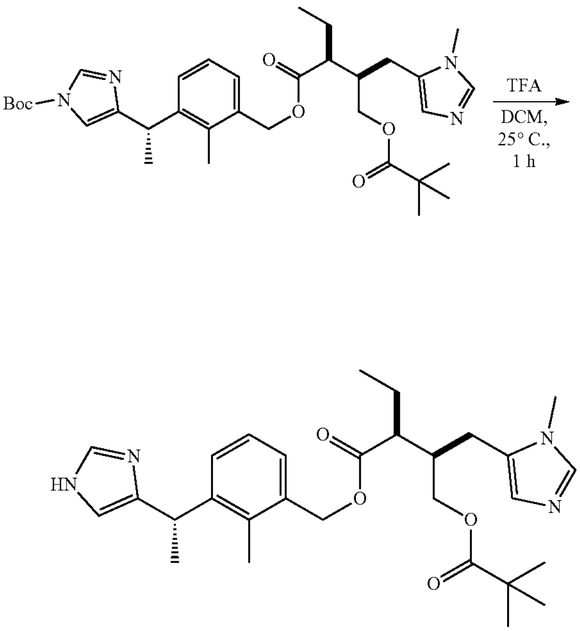

To a solution of tert-butyl 4-((S)-1-(3-((((2S,3R)-2-ethyl-4-(1-methyl-1H-imidazol-5-yl)-3-((pivaloyloxy)methyl)butanoyl)oxy)methyl)-2-methylphenyl)ethyl)-1H-imidazole-1-carboxylate (prepared above, 100 mg, 0.16 mmol) in $CH_2Cl_2$ (10 mL) was added TFA (2 mL) at 25 C. The mixture was stirred at 25 C for 1 h. LCMS showed the reaction worked well. The pH value was adjusted with sat. aq. $NaHCO_3$ to 8. The mixture was extracted with $CH_2Cl_2$ (2×50 mL). The organic layers were concentrated and purified by prep-HPLC ($NH_3 \cdot H_2O$) to afford the desired 3-((S)-1-(1H-imidazol-4-yl)ethyl)-2-methylbenzyl (2S,3R)-2-ethyl-4-(1-methyl-1H-imidazol-5-yl)-3-((pivaloyloxy) methyl)butanoate (40 mg, 48% yield) as a white solid. Prep-HPLC conditions: Chromatographic columns: WELCH Xtimate C18 21.2*250 mm 10 um. Mobile Phase: ACN—$H_2O$ (0.05% $NH_3 \cdot H_2O$) Gradient: 45-75. $^1H$ NMR (400 MHz, $CDCl_3$) δ 7.63 (s, 1H), 7.22 (d, J=7.6 Hz, 1H), 7.18-6.99 (m, 3H), 6.89 (s, 1H), 6.35 (s, 1H), 5.23-5.10 (m, 2H), 4.41 (d, J=6.8 Hz, 1H), 3.99 (d, J=3.6 Hz, 2H), 3.39 (s, 3H), 2.41-2.48 (m, 4H), 2.32 (s, 3H), 1.75-1.62 (m, 2H), 1.58 (d, J=7.2 Hz, 3H), 1.20 (s, 9H), 0.93 (t, J=7.3 Hz, 3H). LCMS (ESI) calcd for $C_{29}H_{40}N_4O_4^+$ $[M+H]^+$ m/z 509.3, found 509.4.

Example 15: Synthesis of (2R,3S)-3-((Z)-2-((4-bromo-1H-benzo[d]imidazol-5-yl)imino)imidazolidine-1-carbonyl)-2-((1-methyl-1H-imidazol-5-yl)methyl)pentyl acetate

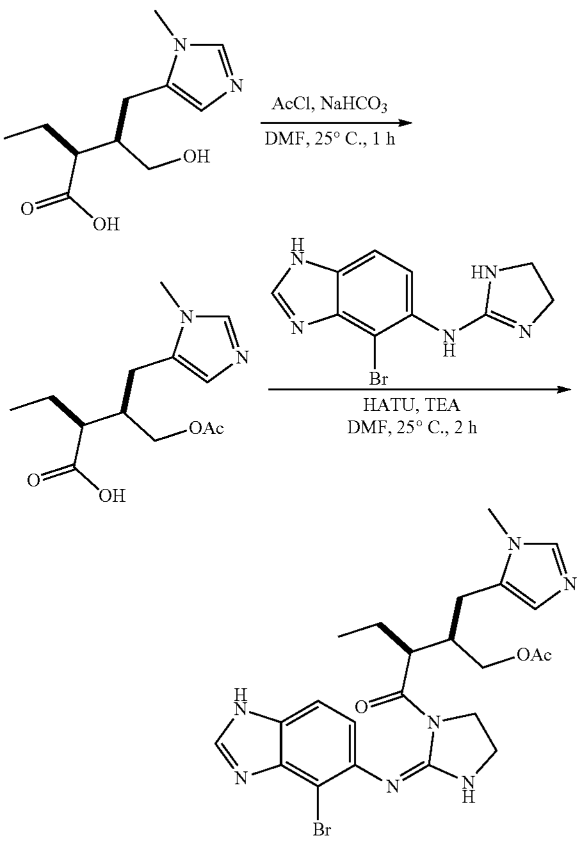

(2S,3R)-4-Acetoxy-2-ethyl-3-((1-methyl-1H-imidazol-5-yl)methyl)butanoic acid: To a solution of (2S,3R)-2-ethyl-4-hydroxy-3-[(3-methylimidazol-4-yl)methyl]-butanoic acid (100 mg, 0.44 mmol) in DMF (5 mL) was added $NaHCO_3$ (74 mg, 0.88 mmol) and acetyl chloride (34 mg, 0.44 mmol) at 25 C. The mixture was stirred at 25 C for 1 h. LCMS showed the reaction was complete. The mixture was diluted with water (20 mL) and washed with EtOAc (3×20 mL). The water layer was then concentrated in vacuum to afford the titled (2S,3R)-4-(acetyloxy)-2-ethyl-3-[(3-methylimidazol-4-yl)methyl]butanoic acid (105 mg, 89% yield) as a white solid. LCMS (ESI) calcd for $C_{13}H_{20}N_2O_4^+$ [M+H]+m/z 269.14, found 269.1.

(2R,3S)-3-((Z)-2-((4-Bromo-1H-benzo[d]imidazol-5-yl)imino)imidazolidine-1-carbonyl)-2-((1-methyl-1H-imidazol-5-yl)methyl)pentyl acetate: To a solution of (2S,3R)-4-(acetyloxy)-2-ethyl-3-[(3-methylimidazol-4-yl)methyl]butanoic acid prepared above (100 mg, 0.37 mmol) in DMF (5 ml) was added 4-bromo-N-(4,5-dihydro-1H-imidazol-2-yl)-1H-1,3-benzodiazol-5-amine 3 (104 mg, 0.37 mmol), N,N,N',N'-tetramethyl-O-(7-azabenzotriazol-1-yl)uranium (212 mg, 0.56 mmol) and TEA (113 mg, 1.11 mmol) at 25 C. The mixture was stirred at 25 C for 2 h. LCMS showed the reaction was complete. The mixture was purified by prep-HPLC (FA) to afford the desired (2R,3S)-3-((Z)-2-((4-bromo-1H-benzo[d]imidazol-5-yl)imino)imidazolidine-1-carbonyl)-2-((1-methyl-1H-imidazol-5-yl)methyl)pentyl acetate (17 mg, 8% yield) as a white solid. Prep-HPLC conditions: Chromatographic columns: Xbridge 5u C18 150×19 mm. Mobile Phase: ACN—H2O (0.1% FA). Gradient: 5-10. $^1H$ NMR (400 MHz, $CD_3OD$) δ 8.36 (s, 1H), 8.17 (s, 1H), 7.94 (s, 1H), 7.57 (d, J=7.2 Hz, 1H), 7.12 (s, 1H), 6.94 (d, J=7.2 Hz, 1H), 4.24-4.15 (m, 2H), 4.05-3.85 (m, 2H), 3.70 (s, 3H), 3.37 (d, J=10.4 Hz, 2H), 2.99 (dd, J=15.2, 8.0 Hz, 1H), 2.90-2.83 (m, 1H), 2.58 (d, J=3.2 Hz, 1H), 2.05 (s, 1H), 1.97 (s, 3H), 1.82 (s, 2H), 1.01 (t, J=7.2 Hz, 3H). LCMS (ESI) calcd for $C_{23}H_{28}BrN_7O_3^+$ [M+H]+ m/z 530.14, found 530.0.

Example 16: Synthesis of (2R,3S)-3-((Z)-2-((5-bromoquinoxalin-6-yl)imino)imidazolidine-1-carbonyl)-2-((1-methyl-1H-imidazol-5-yl)methyl)pentyl acetate

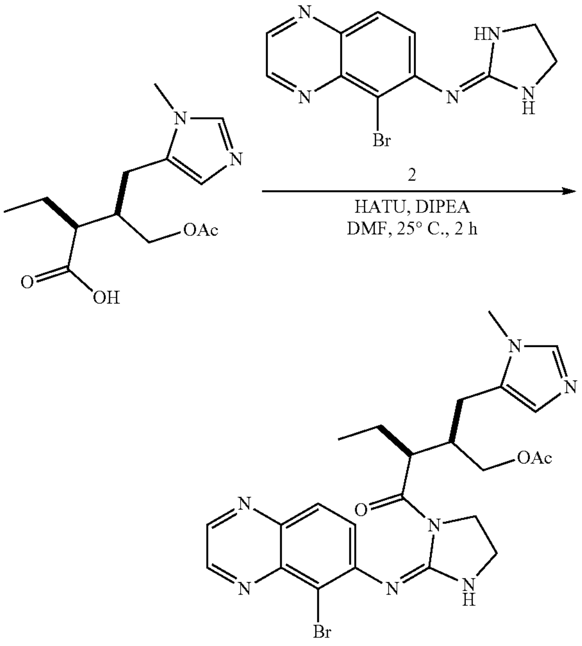

(2R,3S)-3-((Z)-2-((5-Bromoquinoxalin-6-yl)imino)imidazolidine-1-carbonyl)-2-((1-methyl-1H-imidazol-5-yl)methyl)pentyl acetate: To a solution of sodium (2S,3R)-4-(acetyloxy)-2-ethyl-3-[(3-methylimidazol-4-yl)methyl]butanoate prepared above (200 mg, 0.69 mmol) in DMF (5 mL) was added N,N-diisopropylethylamine (267 mg, 2.0 mmol)), N,N,N',N'-tetramethyl-O-(7-azabenzotriazol-1-yl)uranium (314 mg, 0.83 mmol) and 5-bromo-N-(imidazolidin-2-ylidene)quinoxalin-6-amine 2 (201 mg, 0.69 mmol). The mixture stirred at 25 C for 2 h. LCMS showed the reaction was complete. The mixture was purified by prep-HPLC ($NH_3 \cdot H_2O$) to afford the titled (2R,3S)-3-((Z)-2-((5-bromoquinoxalin-6-yl)imino)imidazolidine-1-carbonyl)-2-((1-methyl-1H-imidazol-5-yl)methyl)pentyl acetate (23 mg, 12% yield) as a white solid. Prep-HPLC conditions: Chromatographic columns: Welch 10u C18 250×21.2 mm. Mobile Phase: ACN—H2O (0.1% $NH_3 \cdot H_2O$). Gradient: 35-45. $^1H$ NMR (400 MHz, $CD_3OD$) δ 8.89 (d, J=2.0 Hz, 1H), 8.79 (d, J=2.0 Hz, 1H), 8.03 (d, J=8.8 Hz, 1H), 7.59 (d, J=8.8 Hz, 1H), 7.40 (s, 1H), 6.78 (s, 1H), 4.23-4.14 (m, 2H), 4.05-3.99 (m, 1H), 3.95-3.89 (m, 1H), 3.59 (s, 3H), 3.48-3.40 (m, 2H), 2.96-2.90 (m, 1H), 2.84-2.78 (m, 2H), 2.53 (s, 1H), 1.94 (s, 3H), 1.87-1.78 (m, 2H), 1.02 (t, J=7.2 Hz, 3H). LCMS (ESI) calcd for $C_{24}H_{28}BrN_7O_3^+$ [M+H]+m/z 542.14, found 542.1.

Example 17: Synthesis of (2R,3S)-4-[(2Z)-2-[(4-bromo-1H-1,3-benzodiazol-5-yl)imino]imidazolidin-1-yl]-3-ethyl-2-[(3-methylimidazol-4-yl)methyl]-4-oxobutyl (9Z)-octadec-9-enoate (2R,3S)-3-ethyl-2-[(3-methylimidazol-4-yl)methyl]-4-oxo-4-(sodiooxy)butyl (9Z)-octadec-9-enoate

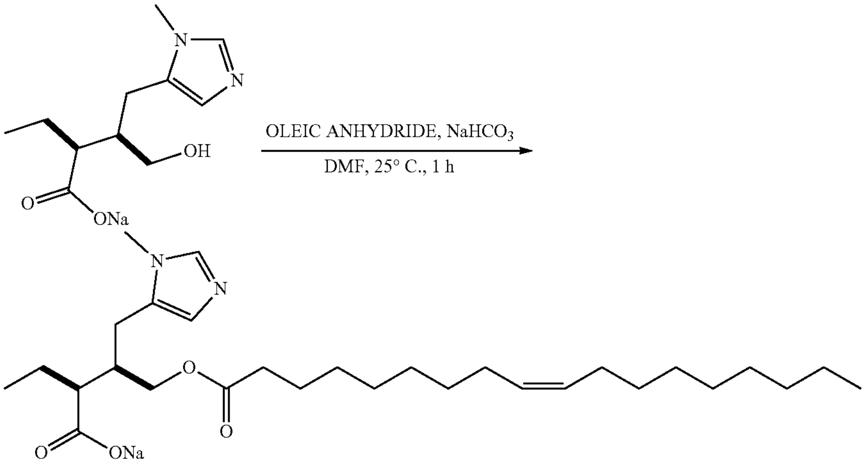

To a solution of (2R,3S)-3-ethyl-2-[(3-methylimidazol-4-yl)methyl]-4-oxo-4-(sodiooxy)butyl (9Z)-octadec-9-enoate (prepared above, 500 mg, 2.01 mmol) in DMF (15 mL) was added $NaHCO_3$ (508 mg, 6.04 mmol) and oleic anhydride (1102 mg, 2.01 mmol). The reaction mixture was stirred at 25 C for 1 h. LCMS showed the reaction worked well. The reaction mixture was washed with water (50 mL) and extracted with EtOAc (3×50 mL). The combined organic layer was washed with brine (50 mL) and dried over anhydrous $Na_2SO_4$. The aqueous phase was freeze-dried to afford the titled (2R,3S)-3-ethyl-2-[(3-methylimidazol-4-yl)methyl]-4-oxo-4-(sodiooxy)butyl (9Z)-octadec-9-enoate (600 mg, 52% yield) as a white solid. LCMS (ESI) calcd for $C_{29}H_{50}N_2O_4^+$ $[M+H]^+$ m/z 491.38, found 491.4.

(2R,3S)-4-[(2Z)-2-[(4-Bromo-1H-1,3-benzodiazol-5-yl)imino]imidazolidin-1-yl]-3-ethyl-2-[(3-methylimidazol-4-yl)methyl]-4-oxobutyl (9Z)-octadec-9-enoate

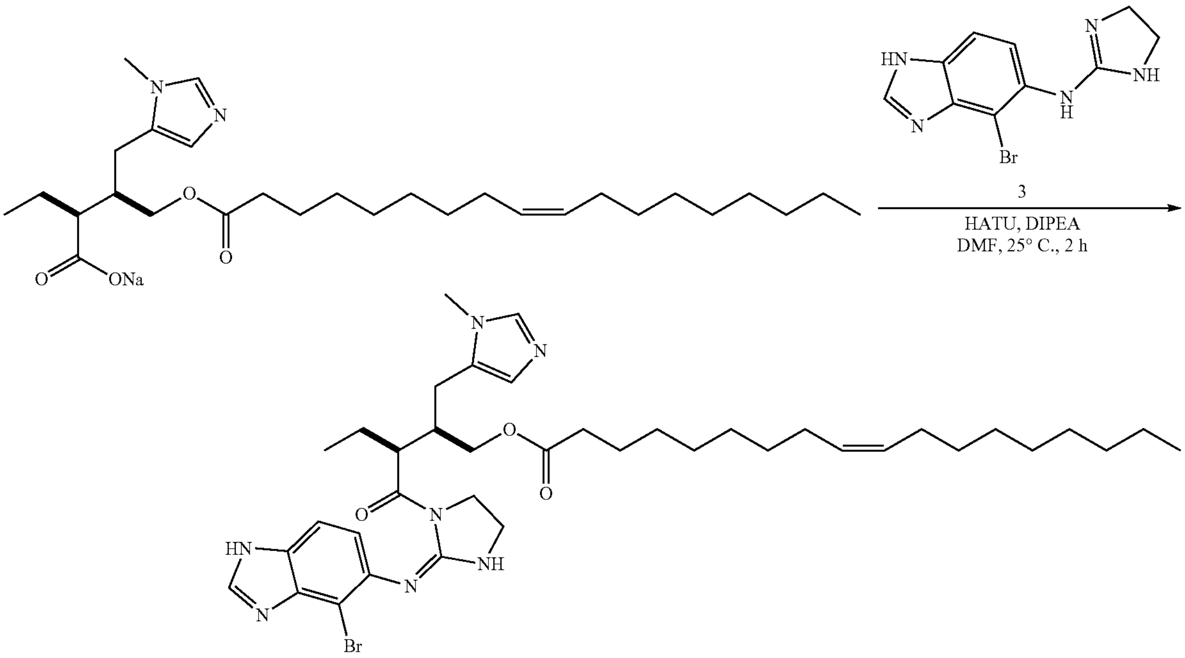

To a solution of (2R,3S)-3-ethyl-2-[(3-methylimidazol-4-yl)methyl]-4-oxo-4-(sodiooxy)butyl (9Z)-octadec-9-enoate (prepared above, 485 mg, 0.95 mmol) in DMF (15 ml) was added 4-bromo-N-(4,5-dihydro-1H-imidazol-2-yl)-1H-1,3-benzodiazol-5-amine 3 (398 mg, 1.42 mmol), N,N,N',N'-Tetramethyl-O-(7-azabenzotriazol-1-yl)uranium (540 mg, 1.42 mmol) and DIPEA (367 mg, 2.84 mmol) at 25 C. The mixture was stirred at 25 C for 2 h. LCMS showed the reaction was well. The mixture was purified by prep-HPLC (FA) to afford the desired (2R,3S)-4-[(2Z)-2-[(4-bromo-1H-1,3-benzodiazol-5-yl)imino]-imidazolidin-1-yl]-3-ethyl-2-[(3-methylimidazol-4-yl)methyl]-4-oxobutyl (9Z)-octadec-9-enoate (210 mg, 30% yield) as a white solid. Prep-HPLC conditions: Chromatographic columns: Xbridge 5u C18 150×19 mm. Mobile Phase: CAN—$H_2O$ (0.1% FA). Gradient: 5-10. $^1$H NMR (400 MHz, DMSO-$d_6$) δ 8.17 (s, 2H), 8.08 (d, J=8.4 Hz, 1H), 7.49 (d, J=7.3 Hz, 1H), 7.42 (s, 1H), 6.81 (d, J=8.2 Hz, 1H), 6.60 (s, 1H), 5.35-5.25 (m, 2H), 4.97 (s, 1H), 4.07 (d, J=11.0 Hz, 1H), 3.97-3.72 (m, 4H), 3.46 (s, 3H), 3.25 (t, J=7.7 Hz, 2H), 2.76 (dd, J=15.2, 10.3 Hz, 1H), 2.63-2.55 (m, 1H), 2.28 (s, 1H), 2.11 (t, J=7.5 Hz, 2H), 2.05-1.84 (m, 5H), 1.74-1.59 (m, 2H), 1.35 (s, 3H), 1.25 (d, J=19.4 Hz, 12H), 1.17 (s, 3H), 0.99 (s, 6H), 0.89 (t, J=7.3 Hz, 3H), 0.84 (t, J=6.8 Hz, 3H). LCMS (ESI) calcd for $C_{39}H_{58}BrN_7O_3^+$ [M+H]$^+$ m/z 752.38, found 752.3.

Example 18: Synthesis of (2R,3S)-4-[(2Z)-2-[(5-bromoquinoxalin-6-yl)imino]imidazolidin-1-yl]-3-ethyl-2-[(3-methylimidazol-4-yl)methyl]-4-oxobutyl (9Z)-octadec-9-enoate To a solution of (2R,3S)-3-ethyl-2-[(3-methylimidazol-4-yl)methyl]-4-oxo-4-(sodiooxy)butyl (9Z)-octadec-9-enoate (prepared above, 200 mg, 0.3901 mmol) in DMF (15 mL) was added 5-bromo-N-(4,5-dihydro-1H-imidazol-2-yl)quinoxalin-6-amine (114 mg, 0.3901 mmol) and TEA (79 mg, 0.7802 mmol). The reaction mixture was stirred at 25° C. for 2 h. LCMS showed the reaction worked well. The reaction mixture was poured into water (50 mL) and extracted with EtOAc (3×50 mL). The combined organic layer was dried over anhydrous $Na_2SO_4$ and concentrated in vacuum. The residue was purified by silica gel column chromatography to give the product as a crude. The crude was purified by prep-HPLC (0.1% FA) to afford the desired (2R,3S)-4-[({2-[(5-bromoquinoxalin-6-yl)amino]-4,5-dihydroimidazol-1-yl}carbonyloxy)methoxy]-3-ethyl-2-[(3-methylimidazol-4-yl)methyl]-4-oxobutyl (9Z)-octadec-9-enoate (185.6 mg, 62.21% yield) as a yellow solid. Prep-HPLC conditions: Chromatographic columns: Xbridge 5u C18 150×19 mm. Mobile Phase: ACN—$H_2O$ (0.1% FA). Gradient: 70-80. $^1$H NMR (400 MHz, $CDCl_3$) δ 8.79 (d, J=26.4 Hz, 1H), 8.64 (d, J=32.8 Hz, 2H), 8.33 (d, J=32.4 Hz, 1H), 8.13-7.95 (m, 1H), 7.83 (d, J=8.8 Hz, 1H), 7.41 (d, J=8.4 Hz, 1H), 7.28 (s, 1H), 5.62 (s, 1H), 5.42-5.24 (m, 3H), 4.89 (s, 1H), 4.16 (d, J=4.5 Hz, 4H), 4.01 (s, 3H), 3.83 (d, J=20.4 Hz, 5H), 3.53 (d, J=7.6 Hz, 2H), 2.83 (s, 4H), 2.56 (s, 2H), 2.35 (s, 1H), 2.21 (s, 2H), 1.95 (dd, J=22.8, 6.4 Hz, 7H), 1.80 (d, J=7.8 Hz, 2H), 1.46 (s, 3H), 1.26 (s, 26H), 1.06 (s, 8H), 0.99 (d, J=6.8 Hz, 3H), 0.87 (s, 3H). LCMS (ESI) calcd for $C_{40}H_{58}BrN_7O_3^+$ [M+H]$^+$ m/z 764.0, found 764.0.

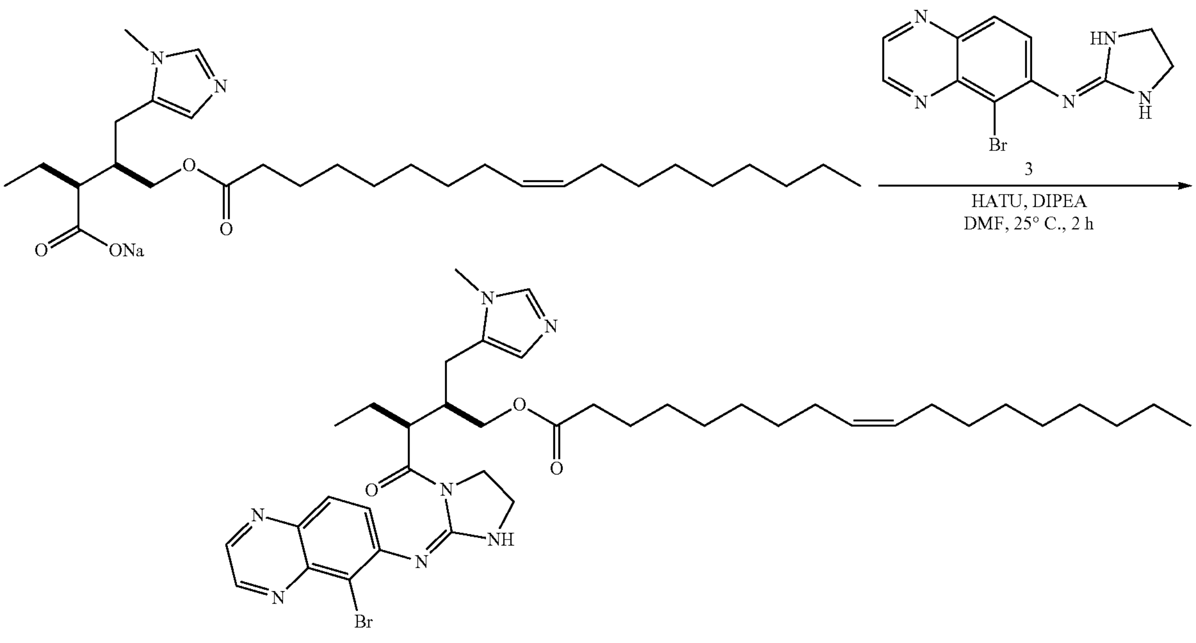

Example 19: Synthesis of (2R,3S)-4-[(2Z)-2-[(4-bromo-1H-1,3-benzodiazol-5-yl)imino]imidazolidin-1-yl]-3-ethyl-2-[(3-methylimidazol-4-yl)methyl]-4-oxobutyl 2,2-dimethylpropanoate

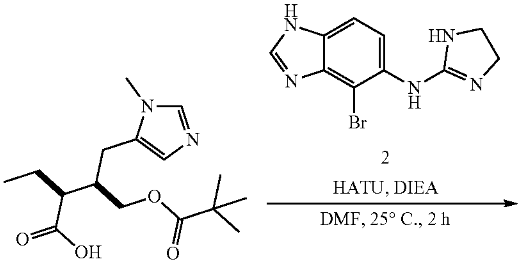

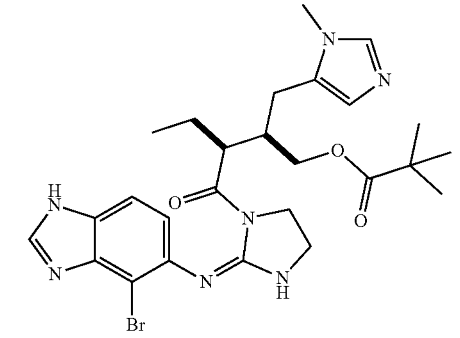

To a solution of sodium (2S,3R)-4-[(2,2-dimethylpropanoyl)oxy]-2-ethyl-3-[(3-methylimidazol-4-yl)methyl]butanoate (prepared above, 200 mg, 0.60 mmol) in DMF (5 mL) was added N,N-diisopropylethylamine (232 mg, 1.80 mmol), N,N,N',N'-tetramethyl-O-(7-azabenzotriazol-1-yl) uranium (342 mg, 0.90 mmol) and 4-bromo-N-(4,5-dihydro-1H-imidazol-2-yl)-1H-1,3-benzodiazol-5-amine 2 (253 mg, 0.90 mmol). The mixture stirred at 25 C for 2 h. LCMS showed the reaction was well. The mixture was purified by prep-HPLC (FA) to afford the desired (2R,3S)-4-[(2Z)-2-[(4-bromo-1H-1,3-benzodiazol-5-yl)imino]imidazolidin-1-yl]-3-ethyl-2-[(3-methylimidazol-4-yl)methyl]-4-oxobutyl 2,2-dimethylpropanoate (75 mg, 21% yield) as a white solid. Prep-HPLC conditions: Chromatographic columns: Welch 10u C18 250×21.2 mm. Mobile Phase: ACN—$H_2O$ (0.1% FA). Gradient: 45-50. LCMS (ESI) calcd for $C_{26}H_{34}BrN_7O_3^+$ $[M+H]^+$ m/z 572.19, found 572.2. $^1H$ NMR (400 MHz, $CDCl_3$) δ 8.39 (s, 1H), 7.78 (s, 1H), 7.64 (s, 1H), 7.43 (s, 1H), 7.05 (s, 1H), 6.74 (d, J=7.2 Hz, 1H), 5.43 (s, 1H), 4.65 (s, 1H), 4.29 (d, J=9.6 Hz, 1H), 4.10 (s, 1H), 3.95-3.85 (m, 1H), 3.62 (s, 3H), 3.50-3.41 (m, 2H), 2.85 (dd, J=15.2, 6.0 Hz, 1H), 2.77 (d, J=9.2 Hz, 1H), 2.63 (s, 1H), 1.84 (d, J=7.6 Hz, 1H), 1.66 (s, 1H), 1.27 (s, 2H), 1.16 (s, 9H), 0.95 (t, J=7.2 Hz, 3H).

Example 20: Synthesis of (2R,3S)-4-[(2Z)-2-[(5-bromoquinoxalin-6-yl)imino]imidazolidin-1-yl]-3-ethyl-2-[(3-methylimidazol-4-yl)methyl]-4-oxobutyl 2,2-dimethylpropanoate Sodium (2S,3R)-4-[(2,2-dimethylpropanoyl)oxy]-2-ethyl-3-[(3-methylimidazol-4-yl)methyl]butanoate

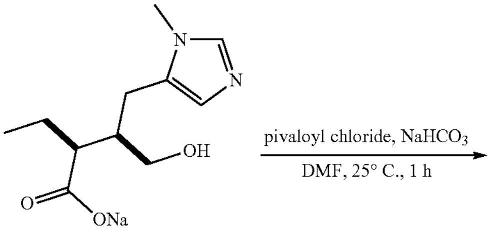

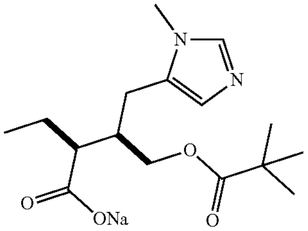

To a solution of sodium (2S,3R)-2-ethyl-4-hydroxy-3-[(3-methylimidazol-4-yl)methyl]butanoate (prepared above, 500 mg, 2.02 mmol) in DMF (5 mL) was added $NaHCO_3$ (340 mg, 4.04 mmol) and pivaloyl chloride (242 mg, 2.02 mmol) at 25 C. The mixture was stirred at 25 C for 1 h. LCMS showed the reaction was well. The mixture was diluted with water (20 mL) and washed with EtOAc (3×20 mL). The water layer was concentrated in vacuum to afford the desired sodium (2S,3R)-4-[(2,2-dimethylpropanoyl)-oxy]-2-ethyl-3-[(3-methylimidazol-4-yl)methyl]butanoate (240 mg, 37% yield) as a white solid. LCMS (ESI) calcd for $C_{16}H_{26}N_2O_4^+$ $[M+H]^+$ m/z 311.19, found 311.0.

(2R,3S)-4-[(2Z)-2-[(5-Bromoquinoxalin-6-yl)imino]imidazolidin-1-yl]-3-ethyl-2-[(3-methylimidazol-4-yl)methyl]-4-oxobutyl 2,2-dimethylpropanoate

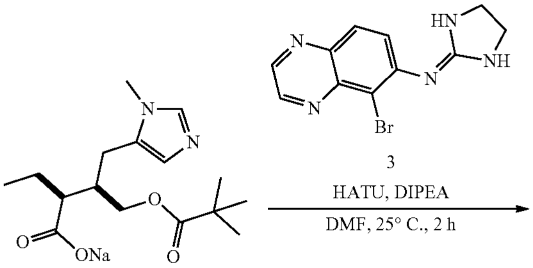

-continued

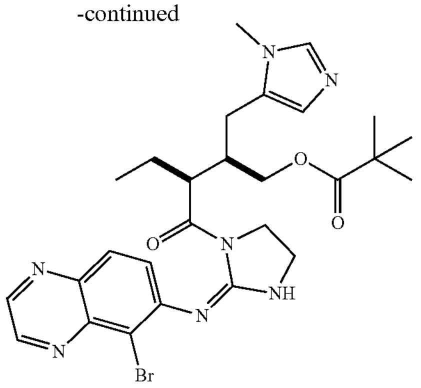

To a solution of sodium (2S,3R)-4-[(2,2-dimethylpropanoyl)oxy]-2-ethyl-3-[(3-methylimidazol-4-yl)methyl]butanoate (prepared above, 200 mg, 0.60 mmol) in DMF (5 mL) was added N,N-diisopropylethylamine (232 mg, 1.80 mmol), N,N,N',N'-tetramethyl-O-(7-azabenzotriazol-1-yl) uranium (342 mg, 0.90 mmol) and 5-bromo-N-(imidazolidin-2-ylidene)quinoxalin-6-amine (174 mg, 0.60 mmol). The mixture was stirred at 25 C for 2 h. LCMS showed the reaction was well. The mixture was purified by prep-HPLC (FA) to afford the desired (2R,3S)-4-[(2Z)-2-[(5-bromoquinoxalin-6-yl)imino]imidazolidin-1-yl]-3-ethyl-2-[(3-methylimidazol-4-yl)methyl]-4-oxobutyl 2,2-dimethylpropanoate (105 mg, 30% yield) as a white solid. Prep-HPLC conditions: Chromatographic columns: Welch 10u C18 250×21.2 mm. Mobile Phase: ACN—$H_2O$ (0.1% FA). Gradient: 35-45. LCMS (ESI) calcd for $C_{27}H_{34}BrN_7O_3^+$ $[M+H]^+$ m/z 584.19, found 584.2. $^1H$ NMR (400 MHz, DMSO-$d_6$) δ 8.95 (d, J=1.8 Hz, 1H), 8.83 (d, J=1.8 Hz, 1H), 7.99 (d, J=8.8 Hz, 1H), 7.57-7.46 (m, 2H), 7.10 (s, 1H), 6.65 (s, 1H), 5.01-4.93 (m, 1H), 4.08-4.02 (m, 1H), 3.95-3.82 (m, 3H), 3.50 (s, 3H), 2.80 (dd, J=15.2, 10.0 Hz, 1H), 2.69-2.59 (m, 1H), 2.33 (s, 1H), 1.73-1.58 (m, 2H), 1.29-1.13 (m, 2H), 1.01-0.82 (m, 12H).

Example 21: Synthesis of (2R,3S)-3-((E)-2-((4-amino-2,6-dichlorophenyl)imino)imidazolidine-1-carbonyl)-2-((1-methyl-1H-imidazol-5-yl)methyl) pentyl acetate

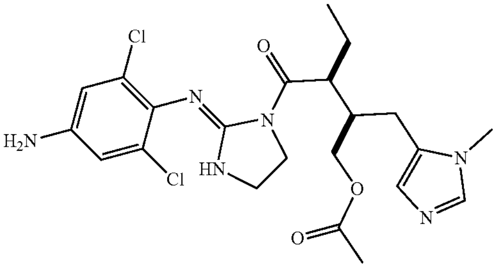 [SMILES: CC[C@H](C(=O)N1CCN/C1=N\c1c(Cl)cc(N)cc1Cl)[C@H](COC(C)=O)Cc1cncn1C]

The titled compound was synthesized using chemistry similar to example 16. Spectroscopic data: $^1H$ NMR (400 MHz, MeOD) δ 7.42 (s, 1H), 6.76 (d, J=5.5 Hz, 3H), 5.06-4.96 (m, 1H), 4.20 (dd, J=11.4, 4.6 Hz, 1H), 4.11 (dd, J=11.4, 3.4 Hz, 1H), 3.98 (ddd, J=11.2, 8.8, 5.6 Hz, 1H), 3.85 (ddd, J=11.4, 9.0, 7.4 Hz, 1H), 3.58 (s, 3H), 3.40 (tt, J=13.0, 6.5 Hz, 2H), 2.94 (dd, J=15.2, 9.1 Hz, 1H), 2.72 (dd, J=15.2, 6.1 Hz, 1H), 2.43 (d, J=3.6 Hz, 1H), 1.92 (d, J=9.7 Hz, 3H), 1.83-1.70 (m, 2H), 0.95 (t, J=7.4 Hz, 3H).

Example 22: Synthesis of (2R,3S)-3-((E)-2-((4-amino-2,6-dichlorophenyl)-imino)imidazolidine-1-carbonyl)-2-((1-methyl-1H-imidazol-5-yl)methyl) pentyl pivalate

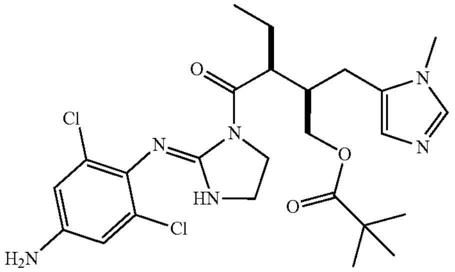 [SMILES: CC[C@H](C(=O)N1CCN/C1=N\c1c(Cl)cc(N)cc1Cl)[C@H](COC(=O)C(C)(C)C)Cc1cncn1C]

The titled compound was synthesized using chemistry similar to example 16. Spectroscopic data: $^1H$ NMR (400 MHz, MeOD) δ 7.47 (s, 1H), 6.75 (d, J=9.1 Hz, 3H), 5.29-5.22 (m, 1H), 4.21 (dd, J=11.5, 3.6 Hz, 1H), 4.05-3.90 (m, 3H), 3.60 (s, 3H), 3.40 (dd, J=8.9, 5.6 Hz, 2H), 3.03-2.97 (m, 1H), 2.75-2.69 (m, 1H), 2.38 (s, 1H), 1.78 (dd, J=8.6, 4.6 Hz, 1H), 1.68-1.61 (m, 1H), 1.08 (d, J=8.5 Hz, 9H), 0.97 (t, J=7.4 Hz, 3H).

Example 23: Synthesis of (2R,3S)-3-((E)-2-((4-amino-2,6-dichlorophenyl)-imino)imidazolidine-1-carbonyl)-2-((1-methyl-1H-imidazol-5-yl)methyl) pentyl oleate

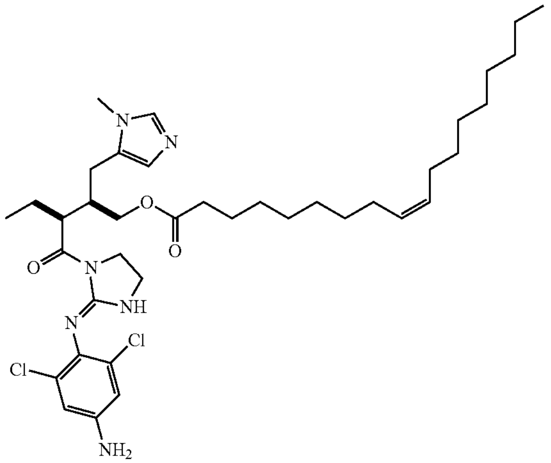

The titled compound was synthesized using chemistry similar to example 16. Spectroscopic data: $^1H$ NMR (400 MHz, cd3od) δ 8.29 (s, 1H), 7.21 (s, 1H), 6.74 (s, 2H), 5.34 (t, J=4.7 Hz, 2H), 4.18 (s, 2H), 4.02 (s, 1H), 3.87 (s, 1H), 3.73 (s, 3H), 3.36 (s, 2H), 2.97 (s, 1H), 2.81 (dd, J=15.3, 6.9 Hz, 1H), 2.50 (s, 1H), 2.25 (s, 1H), 2.05-1.99 (m, 4H), 1.77 (s, 2H), 1.52 (s, 2H), 1.26 (d, J=24.7 Hz, 22H), 0.90 (dd, J=15.9, 9.2 Hz, 6H).

Example 24: Synthesis of (2R,3S)-3-((E)-2-((4-amino-2,6-dichlorophenyl)imino)imidazolidine-1-carbonyl)-2-((1-methyl-1H-imidazol-5-yl)methyl)pentyl propionate

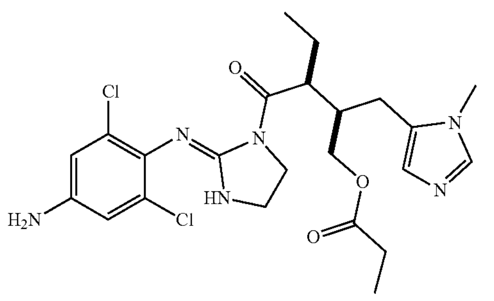 [SMILES: CCC(=O)OC[C@H](Cc1cncn1C)[C@H](CC)C(=O)N1CCN/C1=N\c1c(Cl)cc(N)cc1Cl]

The titled compound was synthesized using chemistry similar to example 16. Spectroscopic data: $^1$H NMR (400 MHz, DMSO) δ 7.41 (s, 1H), 6.68 (s, 1H), 6.62 (d, J=4.8 Hz, 2H), 6.58 (s, 1H), 5.13 (s, 2H), 4.94-4.88 (m, 1H), 4.05 (dd, J=11.4, 3.7 Hz, 1H), 3.93 (dd, J=11.4, 3.3 Hz, 1H), 3.91-3.69 (m, 3H), 3.46 (s, 3H), 3.25 (t, J=7.8 Hz, 2H), 2.77-2.70 (m, 1H), 2.24 (s, 1H), 2.16 (qd, J=7.5, 3.3 Hz, 2H), 1.68-1.57 (m, 2H), 0.87 (dt, J=20.9, 7.5 Hz, 6H).

The structures, IUPAC names and $^1$H NMR data of compounds of Examples 1-6 are shown in Table 1.

TABLE 1

| Comp No. | Structure IUPAC name | $^1$H NMR δ (ppm) |
|---|---|---|
| 1 | 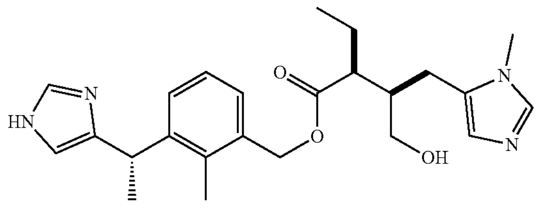 [SMILES: CC[C@H](C(=O)OCc1cccc([C@H](C)c2c[nH]cn2)c1C)[C@H](CO)Cc1cncn1C] 3-((S)-1-(1H-imidazol-4-yl)ethyl)-2-methylbenzyl (2S,3R)-2-ethyl-4-hydroxy-3-((1-methyl-1H-imidazol-5-yl)methyl)butanoate | $^1$H NMR (400 MHZ, $CD_3OD$) δ 8.18 (d, J = 1.0 Hz, 1H), 8.08 (s, 1H), 7.29 (t, J = 5.6 Hz, 1H), 7.17 (t, J = 7.6 Hz, 1H), 7.11-7.04 (m, 2H), 6.94 (s, 1H), 5.22 (s, 2H), 4.53 (q, J = 7.2 Hz, 1H), 3.62 (s, 3H), 3.60-3.56 (m, 1H), 3.34-3.32 (m, 1H), 2.81-2.75 (m, 1H), 2.60-2.49 (m, 2H), 2.41 (s, 3H), 2.07-2.00 (m, 1H), 1.76-1.63 (m, 2H), 1.57 (d, J = 6.0 Hz, 3H), 0.89 (t, J = 7.2 Hz, 3H). |
| 2 | 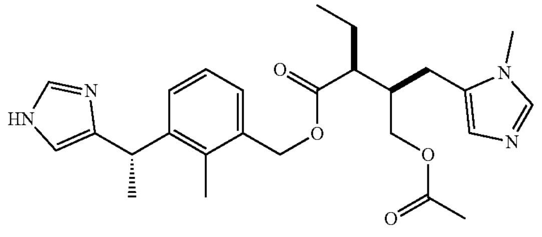 [SMILES: CC[C@H](C(=O)OCc1cccc([C@H](C)c2c[nH]cn2)c1C)[C@H](COC(C)=O)Cc1cncn1C] 3-((S)-1-(1H-imidazol-4-yl)ethyl)-2-methylbenzyl (2S,3R)-4-acetoxy-2-ethyl-3-((1-methyl-1H-imidazol-5-yl)methyl)butanoate | $^1$H NMR (400 MHZ, $CD_3OD$) δ 8.15 (d, J = 9.6 Hz, 1H), 7.96 (d, J = 2.8 Hz, 1H), 7.32-7.27 (m, 1H), 7.18 (t, J = 7.6 Hz, 1H), 7.10 (d, J = 7.6 Hz, 1H), 7.04 (s, 1H), 6.90 (d, J = 8.0 Hz, 1H), 5.23 (d, J = 2.0 Hz, 2H), 4.57-4.46 (m, 1H), 4.07 (t, J = 4.1 Hz, 2H), 3.68-3.48 (m, 3H), 2.80-2.62 (m, 2H), 2.548-2.49 (m, 1H), 2.47-2.35 (m, 3H), 2.38-2.29 (m, 1H), 2.01 (d, J = 9.6 Hz, 3H), 1.76-1.66 (m, 2H), 1.64-1.56 (m, 3H), 0.90 (t, J = 7.6 Hz, 3H). |

TABLE 1-continued

| Comp No. | Structure IUPAC name | $^1$H NMR δ (ppm) |
| --- | --- | --- |
| 3 | 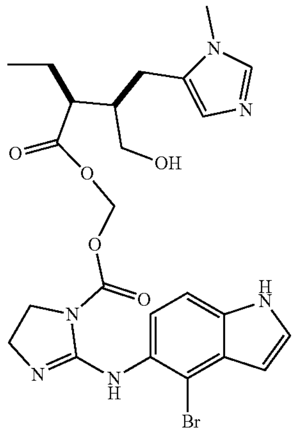 [SMILES: CC[C@H](C(=O)OCOC(=O)N1CCN=C1Nc1ccc2[nH]ccc2c1Br)[C@H](CO)Cc1cncn1C] (((2S,3R)-2-ethyl-4-hydroxy-3-((1-methyl-1H-imidazol-5-yl)methyl)butanoyl)oxy)methyl 2-((4-bromo-1H-benzo[d]imidazol-5-yl)amino)-4,5-dihydro-1H-imidazole-1-carboxylate | $^1$H NMR (400 MHZ, DMSO-$d_6$) δ 9.65 (s, 1H), 8.54 (d, J = 8.8 Hz, 1H), 8.22 (d, J = 26.4 Hz, 1H), 7.49 (s, 2H), 6.65 (s, 2H), 5.92-5.84 (m, 2H), 3.96 (s, 1H), 3.80-3.72 (m, 3H), 3.51 (s, 3H), 3.33-3.19 (m, 2H), 2.61 (d, J = 5.3 Hz, 2H), 2.27 (s, 1H), 1.99-1.97 (m, 1H), 1.65-1.60 (m, 2H), 0.87 (t, J = 2.0 Hz 3H). |
| 4 | 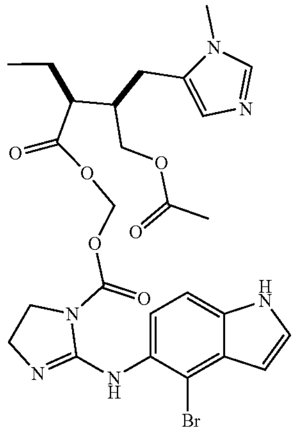 [SMILES: CC[C@H](C(=O)OCOC(=O)N1CCN=C1Nc1ccc2[nH]ccc2c1Br)[C@H](COC(C)=O)Cc1cncn1C] (((2S,3R)-4-acetoxy-2-ethyl-3-((1-methyl-1H-imidazol-5-yl)methyl)butanoyl)oxy)methyl 2-((4-bromo-1H-benzo[d]imidazol-5-yl)amino)-4,5-dihydro-1H-imidazole-1-carboxylate | $^1$H NMR (400 MHZ, DMSO-$d_6$) δ 9.65 (s, 1H), 8.54 (d, J = 8.8 Hz, 1H), 8.22 (d, J = 26.4 Hz, 1H), 7.49 (s, 2H), 6.65 (s, 2H), 5.92-5.84 (m, 2H), 3.96 (s, 1H), 3.80-3.72 (m, 5H), 3.51 (s, 3H), 2.61 (d, J = 5.3 Hz, 2H), 2.27 (s, 1H), 1.99-1.97 (m, 4H), 1.65-1.60 (m, 2H), 0.87 (t, J = 2.0 Hz 3H). |

TABLE 1-continued

| Comp No. | Structure IUPAC name | $^1$H NMR δ (ppm) |
|---|---|---|
| 5 | 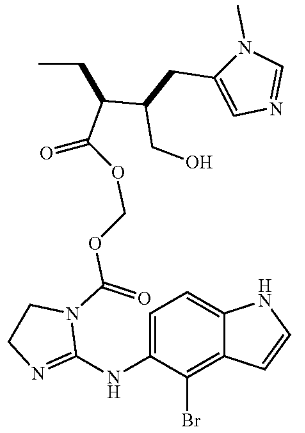 [SMILES: CC[C@H](C(=O)OCOC(=O)N1CCN=C1Nc1ccc2[nH]ccc2c1Br)[C@H](CO)Cc1cncn1C] (((2S,3R)-2-ethyl-4-hydroxy-3-((1-methyl-1H-imidazol-5-yl)methyl)butanoyl)oxy)methyl 2-((5-bromoquinoxalin-6-yl)amino)-4,5-dihydro-1H-imidazole-1-carboxylate | $^1$H NMR (400 MHZ, $CD_3OD$) δ 8.85 (dd, J = 38.4, 1.6 Hz, 3H), 8.04 (d, J = 9.2 Hz, 1H), 7.53 (s, 1H), 6.76 (s, 1H), 6.01 (d, J = 6.0 Hz, 1H), 5.92 (d, J = 6.0 Hz, 1H), 3.97 (s, 2H), 3.77 (s, 1H), 3.64 (d, J = 3.2 Hz, 3H), 3.33-3.22 (m, 2H), 2.75 (d, J = 7.2 Hz, 2H), 2.65-2.54 (m, 1H), 2.47-2.35 (m, 1H), 1.82-1.68 (m, 2H), 0.98 (t, J = 7.2 Hz, 3H). |
| 6 | 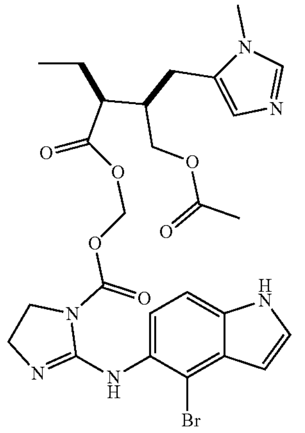 [SMILES: CC[C@H](C(=O)OCOC(=O)N1CCN=C1Nc1ccc2[nH]ccc2c1Br)[C@H](COC(C)=O)Cc1cncn1C] (((2S,3R)-4-acetoxy-2-ethyl-3-((1-methyl-1H-imidazol-5-yl)methyl)butanoyl)oxy)methyl 2-((5-bromoquinoxalin-6-yl)amino)-4,5-dihydro-1H-imidazole-1-carboxylate | $^1$H NMR (400 MHZ, $CD_3OD$) δ 8.85 (dd, J = 38.4, 1.6 Hz, 3H), 8.04 (d, J = 9.2 Hz, 1H), 7.53 (s, 1H), 6.76 (s, 1H), 6.01 (d, J = 6.0 Hz, 1H), 5.92 (d, J = 6.0 Hz, 1H), 4.18-4.04 (m, 2H), 3.97 (s, 2H), 3.77 (s, 1H), 3.64 (d, J = 3.2 Hz, 3H), 2.75 (d, J = 7.2 Hz, 2H), 2.65-2.54 (m, 1H), 2.47-2.35 (m, 1H), 2.03 (s, 3H), 1.82-1.68 (m, 2H), 0.98 (t, J = 7.2 Hz, 3H). |
| 7 | 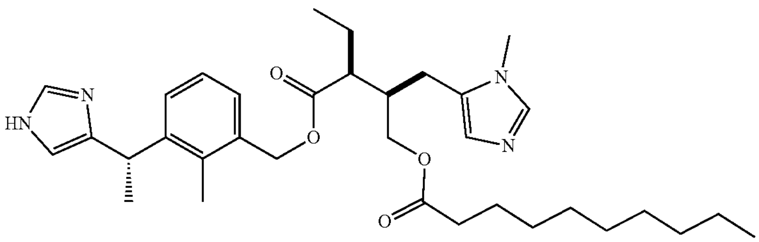 [SMILES: CCCCCCCCCC(=O)OC[C@H](Cc1cncn1C)[C@H](CC)C(=O)OCc1cccc([C@H](C)c2c[nH]cn2)c1C] (2R,3S)-3-(((3-((S)-1-(1H-imidazol-4-yl)ethyl)-2-methylbenzyl)oxy)carbonyl)-2-((1-methyl-1H-imidazol-5-yl)methyl)pentyl decanoate | $^1$H NMR (400 MHZ, $CD_3OD$) δ 8.69 (d, J = 23.2 Hz, 2H), 7.33 (dd, J = 13.2, 5.6 Hz, 3H), 7.21 (t, J = 7.6 Hz, 1H), 7.06 (d, J = 6.8 Hz, 1H), 5.31 (d, J = 12.4 Hz, 1H), 5.23 (d, J = 12.4 Hz, 1H), 4.62 (d, J = 7.2 Hz, 1H), 4.15-4.09 (m, 2H), 3.80 (s, 3H), 2.80 (d, J = 7.6 Hz, 2H), 2.61 (dd, J = 14.1, 7.2 Hz, 2H), 2.44 (s, 3H), 2.33 (t, J = 7.6 Hz, 2H), 1.77-1.70 (m, 2H), 1.64 (d, J = 7.2 Hz, 5H), 1.31 (s, 12H), 0.90 (d, J = 7.2 Hz, 6H). |

TABLE 1-continued

| Comp No. | Structure IUPAC name | $^1$H NMR δ (ppm) |
|---|---|---|
| 8 | 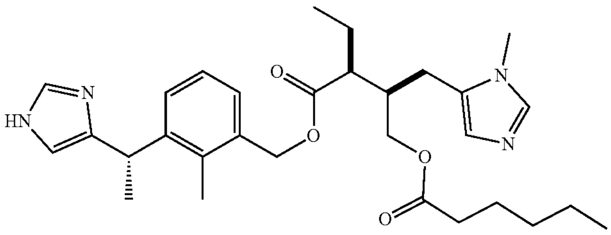 [SMILES: CCCCCC(=O)OC[C@H](Cc1cncn1C)[C@H](CC)C(=O)OCc1cccc([C@H](C)c2c[nH]cn2)c1C] (2R,3S)-3-(((3-((S)-1-(1H-imidazol-4-yl)ethyl)-2-methylbenzyl)oxy)carbonyl)-2-((1-methyl-1H-imidazol-5-yl)methyl)pentyl hexanoate | $^1$H NMR (400 MHZ, $CD_3OD$) δ 7.54 (d, J = 15.2 Hz, 2H), 7.24 (s, 1H), 7.15 (d, J = 6.4 Hz, 2H), 6.70 (s, 2H), 5.22 (s, 2H), 4.44 (d, J = 6.8 Hz, 1H), 4.11-4.01 (m, 2H), 3.55-3.45 (m, 3H), 2.68-2.46 (m, 4H), 2.39 (s, 3H), 2.30 (t, J = 7.6 Hz, 2H), 1.77-1.66 (m, 2H), 1.65-1.45 (m, 5H), 1.32 (s, 4H), 0.91 (dt, J = 12.0, 7.2 Hz, 6H). |
| 9 | 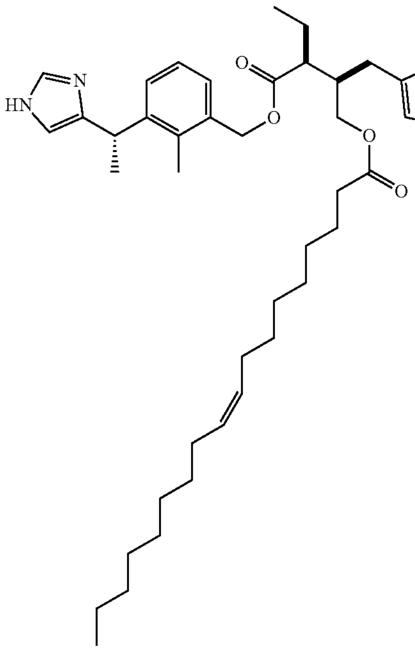 (2R,3S)-3-(((3-((S)-1-(1H-imidazol-4-yl)ethyl)-2-methylbenzyl)oxy)carbonyl)-2-((1-methyl-1H-imidazol-5-yl)methyl)pentyl oleate | $^1$H NMR (400 MHZ, $CDCl_3$) δ 7.90 (s, 1H), 7.23 (d, J = 6.8 Hz, 1H), 7.16-7.09 (m, 2H), 7.01 (d, J = 7.2 Hz, 1H), 6.96 (s, 1H), 6.30 (s, 1H), 5.38-5.30 (m, 2H), 5.20 (d, J = 12.0 Hz, 1H), 5.07 (d, J = 12.0 Hz, 1H), 4.46-4.41 (m, 1H), 4.08-3.97 (m, 2H), 3.40 (s, 3H), 2.57 (dd, J = 15.2, 6.8 Hz, 1H), 2.52-2.39 (m, 2H), 2.38-2.27 (m, 6H), 2.03-1.97 (m, 4H), 1.68-1.54 (m, 7H), 1.28 (d, J = 16.0 Hz, 20 H), 0.93-0.86 (m, 6H). |
| 10 | 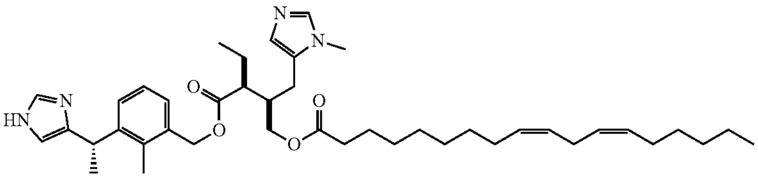 [SMILES: CCCCC/C=C\C/C=C\CCCCCCCC(=O)OC[C@H](Cc1cncn1C)[C@H](CC)C(=O)OCc1cccc([C@H](C)c2c[nH]cn2)c1C] (2R,3S)-3-(((3-((S)-1-(1H-imidazol-4-yl)ethyl)-2-methylbenzyl)oxy)carbonyl)-2-((1-methyl-1H-imidazol-5-yl)methyl)pentyl(9Z,12Z)-octadeca-9,12-dienoate | $^1$H NMR (400 MHz, MeOD) δ 7.72 (s, 1H), 7.58 (s, 1H), 7.17-7.10 (m, 1H), 7.06-6.99 (m, 2H), 6.73 (s, 1H), 6.66 (s, 1H), 5.30-5.17 (m, 4H), 5.10 (s, 2H), 4.39-4.34 (m, 1H), 3.98-3.90 (m, 2H), 3.41 (s, 3H), 2.68-2.62 (m, 2H), 2.56-2.47 (m, 2H), 2.41-2.36 (m, 1H), 2.27 (s, 3H), 2.18-2.15 (m, 4H), 2.00-1.91 (m, 4H), 1.59-1.56 (m, 1H), 1.48-1.45 (m, 5H), 1.27-1.21 (m, 14H), 0.81-0.76 (m, 6H). |

TABLE 1-continued

| Comp No. | Structure IUPAC name | $^1$H NMR δ (ppm) |
| --- | --- | --- |
| 11 | 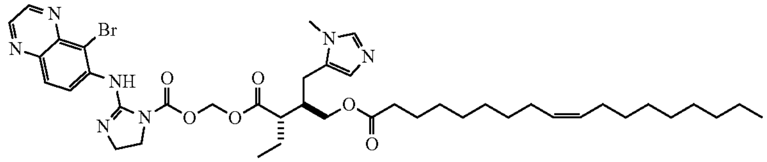 [SMILES: CCCCCCCC/C=C\CCCCCCCC(=O)OC[C@H](Cc1cncn1C)[C@H](CC)C(=O)OCOC(=O)N1CCN=C1Nc1ccc2nccnc2c1Br] (((2S,3R)-2-ethyl-4-(1-methyl-1H-imidazol-5-yl)-3-((oleoyloxy)methyl)butanoyl)oxy)methyl 2-((5-bromoquinoxalin-6-yl)amino)-4,5-dihydro-1H-imidazole-1-carboxylate | $^1$H NMR (400 MHZ, $CDCl_3$) δ 9.24 (d, J = 9.2 Hz, 1 H), 8.90 (d, J = 1.6 Hz, 1 H), 8.77 (d, J = 1.6 Hz, 1 H), 8.08 (d, J = 9.2 Hz, 1 H), 7.71 (s, 1 H), 6.91 (s, 1 H), 5.93 (dd, J = 10.4, 5.6 Hz, 2 H), 5.36-5.29 (m, 2 H), 4.07 (s, 1 H), 3.93 (d, J = 9.6 Hz, 2 H), 3.64 (s, 3 H), 2.68 (t, J = 7.2 Hz, 2 H), 2.58 (td, J = 8.4, 5.2 Hz, 1 H), 2.31-2.19 (m, 6 H), 1.99 (d, J = 6.0 Hz, 4 H), 1.69 (dd, J = 12.4, 7.2 Hz, 2 H), 1.62-1.56 (m, 2 H), 1.26 (s, 20 H), 0.95 (t, J = 7.2 Hz, 3 H), 0.88 (d, J = 6.4 Hz, 3 H). |
| 12 | 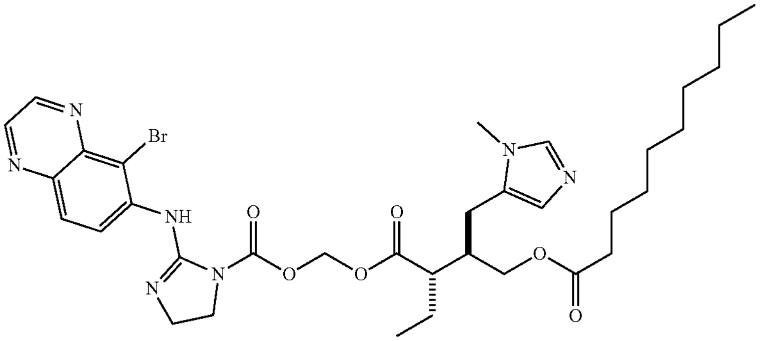 [SMILES: CCCCCCCCCC(=O)OC[C@H](Cc1cncn1C)[C@H](CC)C(=O)OCOC(=O)N1CCN=C1Nc1ccc2nccnc2c1Br] (((2S,3R)-4-(decanoyloxy)-2-ethyl-3-((1-methyl-1H-imidazol-5-yl)methyl)butanoyl)oxy)methyl 2-((5-bromoquinoxalin-6-yl)amino)-4,5-dihydro-1H-imidazole-1-carboxylate | $^1$H NMR (400 MHZ, $CDCl_3$) δ 9.16 (d, J = 9.2 Hz, 1 H), 8.83 (d, J = 1.6 Hz, 1 H), 8.70 (d, J = 1.6 Hz, 1 H), 8.17 (s, 1 H), 8.01 (d, J = 9.2 Hz, 1 H), 6.97 (s, 1 H), 5.87 (dd, J = 15.6, 5.6 Hz, 2 H), 4.06-3.81 (m, 6 H), 3.69 (s, 3 H), 2.63 (s, 1 H), 2.52 (d, J = 4.8 Hz, 1 H), 2.31-2.15 (m, 4 H), 1.65 (dd, J = 13.2, 6.0 Hz, 2 H), 1.55-1.47 (m, 2 H), 1.17 (d, J = 10.4 Hz, 12 H), 0.87 (dd, J = 13.6, 6.4 Hz, 3 H), 0.79 (t, J = 6.8 Hz, 3 H). |
| 13 | 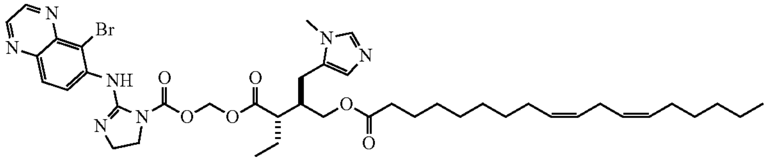 [SMILES: CCCCC/C=C\C/C=C\CCCCCCCC(=O)OC[C@H](Cc1cncn1C)[C@H](CC)C(=O)OCOC(=O)N1CCN=C1Nc1ccc2nccnc2c1Br] (((2S,3R)-2-ethyl-4-(1-methyl-1H-imidazol-5-yl)-3-((((9Z,12Z)-octadeca-9,12-dienoyl)oxy)methyl)butanoyl)oxy)methyl 2-((5-bromoquinoxalin-6-yl)amino)-4,5-dihydro-1H-imidazole-1-carboxylate | $^1$H NMR (400 MHZ, $CDCl_3$) δ 9.25 (s, 1 H), 8.90 (d, J = 1.6 Hz,1 H), 8.77 (d, J = 1.6 Hz, 1 H), 8.08 (d, J = 9.2 Hz, 2 H), 7.00 (s, 1 H), 5.96-5.90 (m, 2 H), 5.37-5.30 (m, 4 H), 4.07 (d, J = 4.4 Hz, 1 H), 3.94 (dd, J = 14.8, 6.0 Hz, 4 H), 3.71 (s, 2 H), 2.77-2.68 (m, 4 H), 2.41 (d, J = 7.6 Hz, 1 H), 2.34-2.24 (m, 4 H), 2.06-2.01 (m, 4 H), 1.42-1.18 (m, 20 H), 0.95 (t, J = 7.2 Hz, 3 H), 0.87 (d, J = 6.8 Hz, 3H). |
| 14 | 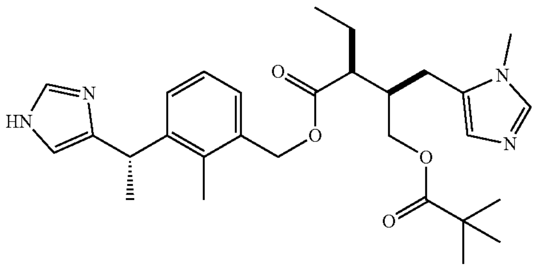 [SMILES: CC[C@H](C(=O)OCc1cccc([C@H](C)c2c[nH]cn2)c1C)[C@H](COC(=O)C(C)(C)C)Cc1cncn1C] 3-((S)-1-(1H-imidazol-4-yl)ethyl)-2-methylbenzyl (2S,3R)-2-ethyl-4-(1-methyl-1H-imidazol-5-yl)-3-((pivaloyloxy)methyl)butanoate | $^1$H NMR (400 MHZ, $CDCl_3$) δ 7.63 (s, 1H), 7.22 (d, J = 7.6 Hz, 1H), 7.18-6.99 (m, 3H), 6.89 (s, 1H), 6.35 (s, 1H), 5.23-5.10 (m, 2H), 4.41 (d, J = 6.8 Hz, 1H), 3.99 (d, J = 3.6 Hz, 2H), 3.39 (s, 3H), 2.41-2.48 (m, 4H), 2.32 (s, 3H), 1.75-1.62 (m, 2H), 1.58 (d, J = 7.2 Hz, 3H), 1.20 (s, 9H), 0.93 (t, J = 7.3 Hz, 3H). |

TABLE 1-continued

| Comp No. | Structure IUPAC name | $^1$H NMR δ (ppm) |
|---|---|---|
| 15 | 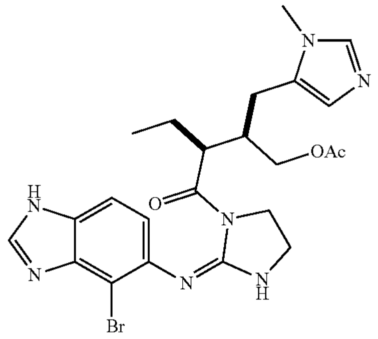 [SMILES: CC[C@H](C(=O)N1CCN/C1=N/c1ccc2[nH]cnc2c1Br)[C@H](COC(C)=O)Cc1cncn1C] (2R,3S)-3-((Z)-2-((4-bromo-1H-benzo[d]imidazol-5-yl)imino)imidazolidine-1-carbonyl)-2-((1-methyl-1H-imidazol-5-yl)methyl)pentyl acetate | $^1$H NMR (400 MHZ, $CD_3OD$) δ 8.36 (s, 1H), 8.17 (s, 1H), 7.94 (s, 1H), 7.57 (d, J = 7.2 Hz, 1H), 7.12 (s, 1H), 6.94 (d, J = 7.2 Hz, 1H), 4.24-4.15 (m, 2H), 4.05-3.85 (m, 2H), 3.70 (s, 3H), 3.37 (d, J = 10.4 Hz, 2H), 2.99 (dd, J = 15.2, 8.0 Hz, 1H), 2.90-2.83 (m, 1H), 2.58 (d, J = 3.2 Hz, 1H), 2.05 (s, 1H), 1.97 (s, 3H), 1.82 (s, 2H), 1.01 (t, J = 7.2 Hz, 3H). |
| 16 | 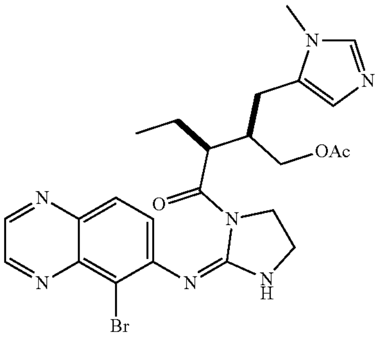 [SMILES: CC[C@H](C(=O)N1CCN/C1=N/c1ccc2nccnc2c1Br)[C@H](COC(C)=O)Cc1cncn1C] (2R,3S)-3-((Z)-2-((5-bromoquinoxalin-6-yl)imino)imidazolidine-1-carbonyl)-2-((1-methyl-1H-imidazol-5-yl)methyl)pentyl acetate | $^1$H NMR (400 MHZ, $CD_3OD$) δ 8.89 (d, J = 2.0 Hz, 1H), 8.79 (d, J = 2.0 Hz, 1H), 8.03 (d, J = 8.8 Hz, 1H), 7.59 (d, J = 8.8 Hz, 1H), 7.40 (s, 1H), 6.78 (s, 1H), 4.23-4.14 (m, 2H), 4.05-3.99 (m, 1H), 3.95-3.89 (m, 1H), 3.59 (s, 3H), 3.48-3.40 (m, 2H), 2.96-2.90 (m, 1H), 2.84-2.78 (m, 2H), 2.53 (s, 1H), 1.94 (s, 3H), 1.87-1.78 (m, 2H), 1.02 (t, J = 7.2 Hz, 3H). |
| 17 | 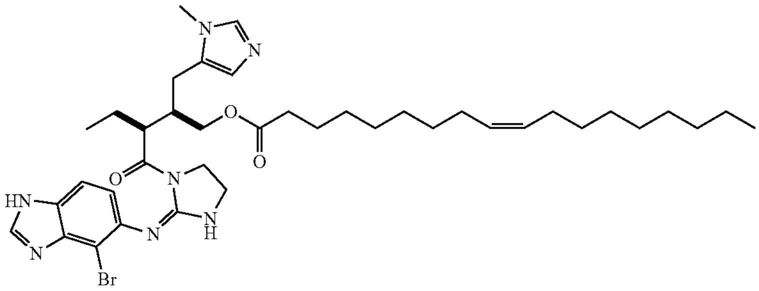 [SMILES: CCCCCCCC/C=C\CCCCCCCC(=O)OC[C@H](Cc1cncn1C)[C@H](CC)C(=O)N1CCN/C1=N/c1ccc2[nH]cnc2c1Br] (2R,3S)-3-((Z)-2-((4-bromo-1H-benzo[d]imidazol-5-yl)imino)imidazolidine-1-carbonyl)-2-((1-methyl-1H-imidazol-5-yl)methyl)pentyl oleate | $^1$H NMR (400 MHZ, DMSO-$d_6$) δ 8.17 (s, 2H), 8.08 (d, J = 8.4 Hz, 1H), 7.49 (d, J = 7.3 Hz, 1H), 7.42 (s, 1H), 6.81 (d, J = 8.2 Hz, 1H), 6.60 (s, 1H), 5.35-5.25 (m, 2H), 4.97 (s, 1H), 4.07 (d, J = 11.0 Hz, 1H), 3.97-3.72 (m, 4H), 3.46 (s, 3H), 3.25 (t, J = 7.7 Hz, 2H), 2.76 (dd, J = 15.2, 10.3 Hz, 1H), 2.63-2.55 (m, 1H), 2.28 (s, 1H), 2.11 (t, J = 7.5 Hz, 2H), 2.05-1.84 (m, 5H), 1.74-1.59 (m, 2H), 1.35 (s, 3H), 1.25 (d, J = 19.4 Hz, 12H), 1.17 (s, 3H), 0.99 (s, 6H), 0.89 (t, J = 7.3 Hz, 3H), 0.84 (t, J = 6.8 Hz, 3H). |

TABLE 1-continued

| Comp No. | Structure IUPAC name | $^1$H NMR δ (ppm) |
|---|---|---|
| 18 | 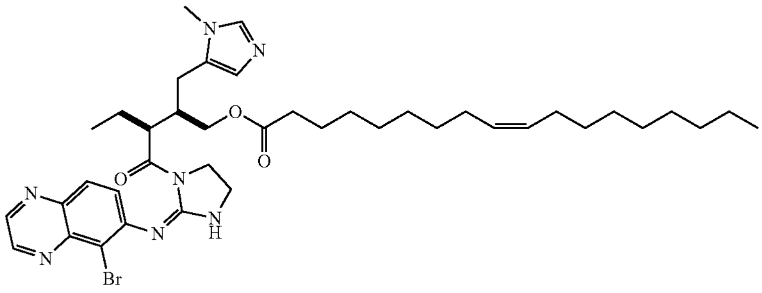 [SMILES: CCCCCCCC/C=C\CCCCCCCC(=O)OC[C@H](Cc1cncn1C)[C@H](CC)C(=O)N1CCN/C1=N/c1ccc2nccnc2c1Br] (2R,3S)-3-((Z)-2-((5-bromoquinoxalin-6-yl)imino)imidazolidine-1-carbonyl)-2-((1-methyl-1H-imidazol-5-yl)methyl)pentyl oleate | $^1$H NMR (400 MHZ, $CDCl_3$) δ 8.79 (d, J = 26.4 Hz, 1H), 8.64 (d, J = 32.8 Hz, 2H), 8.33 (d, J = 32.4 Hz, 1H), 8.13-7.95 (m, 1H), 7.83 (d, J = 8.8 Hz, 1H), 7.41(d, J = 8.4 Hz, 1H), 7.28 (s, 1H), 5.62 (s, 1H), 5.42-5.24 (m, 3H), 4.89 (s, 1H), 4.16 (d, J = 4.5 Hz, 4H), 4.01 (s, 3H), 3.83 (d, J = 20.4 Hz, 5H), 3.53 (d, J = 7.6 Hz, 2H), 2.83 (s, 4H), 2.56 (s, 2H), 2.35 (s, 1H), 2.21 (s, 2H), 1.95 (dd, J = 22.8, 6.4 Hz, 7H), 1.80 (d, J = 7.8 Hz, 2H), 1.46 (s, 3H), 1.26 (s, 26H), 1.06 (s, 8H), 0.99 (d, J = 6.8 Hz, 3H), 0.87 (s, 3H). |
| 19 | 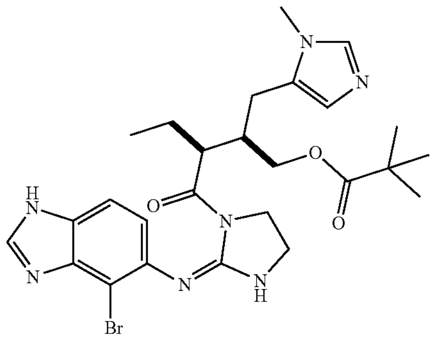 [SMILES: CC[C@H](C(=O)N1CCN/C1=N/c1ccc2[nH]cnc2c1Br)[C@H](COC(=O)C(C)(C)C)Cc1cncn1C] (2R,3S)-3-((Z)-2-((4-bromo-1H-benzo[d]imidazol-5-yl)imino)imidazolidine-1-carbonyl)-2-((1-methyl-1H-imidazol-5-yl)methyl)pentyl pivalate | $^1$H NMR (400 MHZ, $CDCl_3$) δ 8.39 (s, 1H), 7.78 (s, 1H), 7.64 (s, 1H), 7.43 (s, 1H), 7.05 (s, 1H), 6.74 (d, J = 7.2 Hz, 1H), 5.43 (s, 1H), 4.65 (s, 1H), 4.29 (d, J = 9.6 Hz, 1H), 4.10 (s, 1H), 3.95-3.85 (m, 1H), 3.62 (s, 3H), 3.50-3.41 (m, 2H), 2.85 (dd, J = 15.2, 6.0 Hz, 1H), 2.77 (d, J = 9.2 Hz, 1H), 2.63 (s, 1H), 1.84 (d, J = 7.6 Hz, 1H), 1.66 (s, 1H), 1.27 (s, 2H), 1.16 (s, 9H), 0.95 (t, J = 7.2 Hz, 3H). |
| 20 | 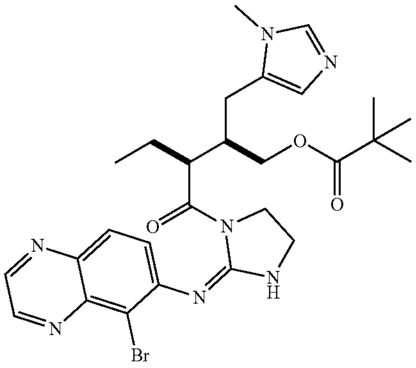 [SMILES: CC[C@H](C(=O)N1CCN/C1=N/c1ccc2nccnc2c1Br)[C@H](COC(=O)C(C)(C)C)Cc1cncn1C] (2R,3S)-3-((Z)-2-((5-bromoquinoxalin-6-yl)imino)imidazolidine-1-carbonyl)-2-((1-methyl-1H-imidazol-5-yl)methyl)pentyl pivalate | $^1$H NMR (400 MHZ, DMSO-$d_6$) δ 8.95 (d, J = 1.8 Hz, 1H), 8.83 (d, J = 1.8 Hz, 1H), 7.99 (d, J = 8.8 Hz, 1H), 7.57-7.46 (m, 2H), 7.10 (s, 1H), 6.65 (s, 1H), 5.01-4.93 (m, 1H), 4.08-4.02 (m, 1H), 3.95-3.82 (m, 3H), 3.50 (s, 3H), 2.80 (dd, J = 15.2, 10.0 Hz, 1H), 2.69-2.59 (m, 1H), 2.33 (s, 1H), 1.73-1.58 (m, 2H), 1.29-1.13 (m, 2H), 1.01-0.82 (m, 12H). |

TABLE 1-continued

| Comp No. | Structure IUPAC name | $^1H$ NMR δ (ppm) |
|---|---|---|
| 21 | 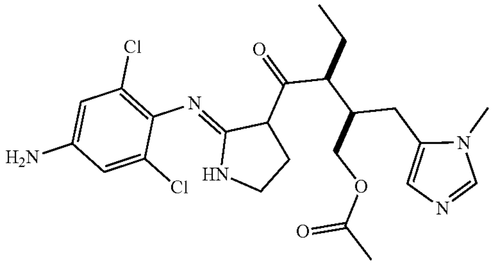 [SMILES: CC[C@H](C(=O)C1CCN/C1=N\c1c(Cl)cc(N)cc1Cl)[C@H](COC(C)=O)Cc1cncn1C] (2R,3S)-3-((E)-2-((4-amino-2,6-dichlorophenyl)imino)imidazolidine-1-carbonyl)-2-((1-methyl-1H-imidazol-5-yl)methyl)pentyl acetate | $^1H$ NMR (400 MHZ, MeOD) δ 7.42 (s, 1H), 6.76 (d, J = 5.5 Hz, 3H), 5.06-4.96 (m, 1H), 4.20 (dd, J = 11.4, 4.6 Hz, 1H), 4.11 (dd, J = 11.4, 3.4 Hz, 1H), 3.98 (ddd, J = 11.2, 8.8, 5.6 Hz, 1H), 3.85 (ddd, J = 11.4, 9.0, 7.4 Hz, 1H), 3.58 (s, 3H), 3.40 (tt, J = 13.0, 6.5 Hz, 2H), 2.94 (dd, J = 15.2, 9.1 Hz, 1H), 2.72 (dd, J = 15.2, 6.1 Hz, 1H), 2.43 (d, J = 3.6 Hz, 1H), 1.92 (d, J = 9.7 Hz, 3H), 1.83-1.70 (m, 2H), 0.95 (t, J = 7.4 Hz, 3H). |
| 22 | 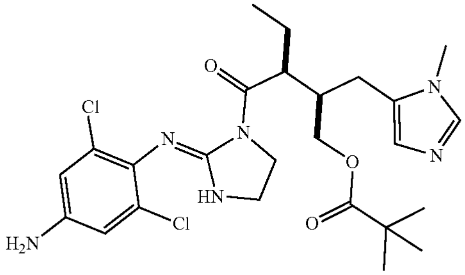 [SMILES: CC[C@H](C(=O)N1CCN/C1=N\c1c(Cl)cc(N)cc1Cl)[C@H](COC(=O)C(C)(C)C)Cc1cncn1C] (2R,3S)-3-((E)-2-((4-amino-2,6-dichlorophenyl)imino)imidazolidine-1-carbonyl)-2-((1-methyl-1H-imidazol-5-yl)methyl)pentyl pivalate | $^1H$ NMR (400 MHZ, MeOD) δ 7.47 (s, 1H), 6.75 (d, J = 9.1 Hz, 3H), 5.29-5.22 (m, 1H), 4.21 (dd, J = 11.5, 3.6 Hz, 1H), 4.05-3.90 (m, 3H), 3.60 (s, 3H), 3.40 (dd, J = 8.9, 5.6 Hz, 2H), 3.03-2.97 (m, 1H), 2.75-2.69 (m, 1H), 2.38 (s, 1H), 1.78 (dd, J = 8.6, 4.6 Hz, 1H), 1.68-1.61 (m, 1H), 1.08 (d, J = 8.5 Hz, 9H), 0.97 (t, J = 7.4 Hz, 3H). |
| 23 | 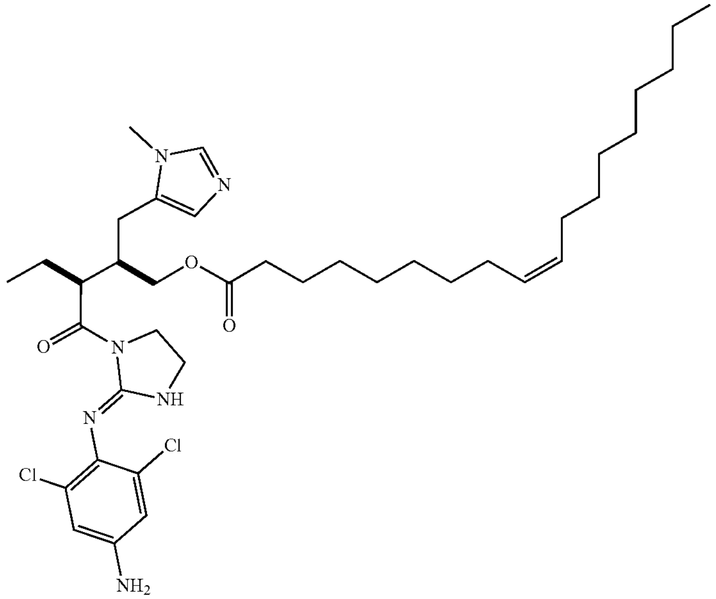 [SMILES: CCCCCCCC/C=C\CCCCCCCC(=O)OC[C@H](Cc1cncn1C)[C@H](CC)C(=O)N1CCN/C1=N\c1c(Cl)cc(N)cc1Cl] (2R,3S)-3-((E)-2-((4-amino-2,6-dichlorophenyl)imino)imidazolidine-1-carbonyl)-2-((1-methyl-1H-imidazol-5-yl)methyl)pentyl oleate | $^1H$ NMR (400 MHZ, cd3od) δ 8.29 (s, 1H), 7.21 (s, 1H), 6.74 (s, 2H), 5.34 (t, J = 4.7 Hz, 2H), 4.18 (s, 2H), 4.02 (s, 1H), 3.87 (s, 1H), 3.73 (s, 3H), 3.36 (s, 2H), 2.97 (s, 1H), 2.81 (dd, J = 15.3, 6.9 Hz, 1H), 2.50 (s, 1H), 2.25 (s, 1H), 2.05-1.99 (m, 4H), 1.77 (s, 2H), 1.52 (s, 2H), 1.26 (d, J = 24.7 Hz, 22H), 0.90 (dd, J = 15.9, 9.2 Hz, 6H). |

TABLE 1-continued

| Comp No. | Structure IUPAC name | $^1$H NMR δ (ppm) |
|---|---|---|
| 24 | 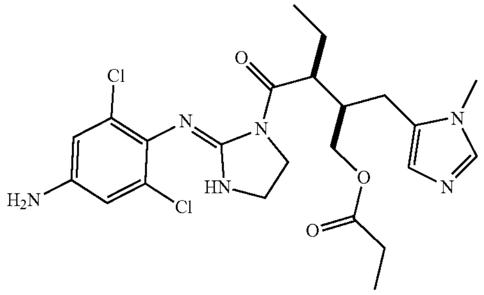 [SMILES: CCC(=O)OC[C@H](Cc1cncn1C)[C@H](CC)C(=O)N1CCN/C1=N\c1c(Cl)cc(N)cc1Cl] (2R,3S)-3-((E)-2-((4-amino-2,6-dichlorophenyl)imino)imidazolidine-1-carbonyl)-2-((1-methyl-1H-imidazol-5-yl)methyl)pentyl propionate | $^1$H NMR (400 MHz, DMSO) δ 7.41 (s, 1H), 6.68 (s, 1H), 6.62 (d, J = 4.8 Hz, 2H), 6.58 (s, 1H), 5.13 (s, 2H), 4.94-4.88 (m, 1H), 4.05 (dd, J = 11.4, 3.7 Hz, 1H), 3.93 (dd, J = 11.4, 3.3 Hz, 1H), 3.91-3.69 (m, 3H), 3.46 (s, 3H), 3.25 (t, J = 7.8 Hz, 2H), 2.77-2.70 (m, 1H), 2.24 (s, 1H), 2.16 (qd, J = 7.5, 3.3 Hz, 2H), 1.68-1.57 (m, 2H), 0.87 (dt, J = 20.9, 7.5 Hz, 6H). |

Compounds 1-(((2S,3R)-2-ethyl-4-hydroxy-3-((1-methyl-1H-imidazol-5-yl)-methyl)butanoyl)oxy)ethyl 2-((4-bromo-1H-benzo[d]imidazol-5-yl)amino)-4,5-dihydro-1H-imidazole-1-carboxylate; 1-(((2S,3R)-4-acetoxy-2-ethyl-3-((1-methyl-1H-imidazol-5-yl)methyl)-butanoyl)oxy)ethyl 2-((4-bromo-1H-benzo[d]imidazol-5-yl)amino)-4,5-dihydro-1H-imidazole-1-carboxylate; 1-(((2S,3R)-2-ethyl-4-hydroxy-3-((1-methyl-1H-imidazol-5-yl)methyl)butanoyl)-oxy)ethyl 2-((5-bromoquinoxalin-6-yl)amino)-4,5-dihydro-1H-imidazole-1-carboxylate; and 1-(((2S,3R)-4-acetoxy-2-ethyl-3-((1-methyl-1H-imidazol-5-yl)methyl)butanoyl)oxy)ethyl 2-((5-bromoquinoxalin-6-yl)amino)-4,5-dihydro-1H-imidazole-1-carboxylate can be prepared in similar ways as Examples 1-14.

Compounds (2R,3S)-3-(2-((4-bromo-1H-benzo[d]imidazol-5-yl)amino)-4,5-dihydro-1H-imidazole-1-carbonyl)-2-((1-methyl-1H-imidazol-5-yl)methyl)pentyl propionate; (2R,3S)-3-(2-((4-bromo-1H-benzo[d]imidazol-5-yl)amino)-4,5-dihydro-1H-imidazole-1-carbonyl)-2-((1-methyl-1H-imidazol-5-yl)methyl)pentyl butyrate; (2R,3S)-3-(2-((4-bromo-1H-benzo[d]imidazol-5-yl)amino)-4,5-dihydro-1H-imidazole-1-carbonyl)-2-((1-methyl-1H-imidazol-5-yl)methyl)pentyl cyclopropanecarboxylate; (2R,3S)-3-(2-((4-bromo-1H-benzo[d]imidazol-5-yl)amino)-4,5-dihydro-1H-imidazole-1-carbonyl)-2-((1-methyl-1H-imidazol-5-yl)methyl)pentyl oleate; (2R,3S)-3-(2-((4-bromo-1H-benzo[d]imidazol-5-yl)amino)-4,5-dihydro-1H-imidazole-1-carbonyl)-2-((1-methyl-1H-imidazol-5-yl)methyl)pentyl (9Z,12Z)-octadeca-9,12-dienoate; (2R,3S)-3-(2-((5-bromoquinoxalin-6-yl)amino)-4,5-dihydro-1H-imidazole-1-carbonyl)-2-((1-methyl-1H-imidazol-5-yl)methyl)pentyl propionate; (2R,3S)-3-(2-((5-bromoquinoxalin-6-yl)amino)-4,5-dihydro-1H-imidazole-1-carbonyl)-2-((1-methyl-1H-imidazol-5-yl)methyl)pentyl butyrate; (2R,3S)-3-(2-((5-bromoquinoxalin-6-yl)amino)-4,5-dihydro-1H-imidazole-1-carbonyl)-2-((1-methyl-1H-imidazol-5-yl)methyl)pentyl cyclopropanecarboxylate; (2R,3S)-3-(2-((5-bromoquinoxalin-6-yl)amino)-4,5-dihydro-1H-imidazole-1-carbonyl)-2-((1-methyl-1H-imidazol-5-yl)methyl)pentyl oleate; (2R,3S)-3-(2-((5-bromoquinoxalin-6-yl)amino)-4,5-dihydro-1H-imidazole-1-carbonyl)-2-((1-methyl-1H-imidazol-5-yl)methyl)pentyl (9Z,12Z)-octadeca-9,12-dienoate; (2R,3S)-3-(2-((4-amino-2,6-dichlorophenyl)amino)-4,5-dihydro-1H-imidazole-1-carbonyl)-2-((1-methyl-1H-imidazol-5-yl)methyl)pentyl acetate; (2R,3S)-3-(2-((4-amino-2,6-dichlorophenyl)amino)-4,5-dihydro-1H-imidazole-1-carbonyl)-2-((1-methyl-1H-imidazol-5-yl)methyl)pentyl propionate; (2R,3S)-3-(2-((4-amino-2,6-dichlorophenyl)amino)-4,5-dihydro-1H-imidazole-1-carbonyl)-2-((1-methyl-1H-imidazol-5-yl)methyl)pentyl butyrate; (2R,3S)-3-(2-((4-amino-2,6-dichlorophenyl)amino)-4,5-dihydro-1H-imidazole-1-carbonyl)-2-((1-methyl-1H-imidazol-5-yl)methyl)pentyl cyclopropanecarboxylate; (2R,3S)-3-(2-((4-amino-2,6-dichlorophenyl)amino)-4,5-dihydro-1H-imidazole-1-carbonyl)-2-((1-methyl-1H-imidazol-5-yl)methyl)pentyl oleate; (2R,3S)-3-(2-((4-amino-2,6-dichlorophenyl)amino)-4,5-dihydro-1H-imidazole-1-carbonyl)-2-((1-methyl-1H-imidazol-5-yl)methyl)pentyl (9Z,12Z)-octadeca-9,12-dienoate; (2R,3S)-3-(2-((2,6-dichlorophenyl)amino)-4,5-dihydro-1H-imidazole-1-carbonyl)-2-((1-methyl-1H-imidazol-5-yl)methyl)pentyl acetate; (2R,3S)-3-(2-((2,6-dichlorophenyl)amino)-4,5-dihydro-1H-imidazole-1-carbonyl)-2-((1-methyl-1H-imidazol-5-yl)methyl)pentyl propionate; (2R,3S)-3-(2-((2,6-dichlorophenyl)amino)-4,5-dihydro-1H-imidazole-1-carbonyl)-2-((1-methyl-1H-imidazol-5-yl)methyl)pentyl butyrate; (2R,3S)-3-(2-((2,6-dichlorophenyl)amino)-4,5-dihydro-1H-imidazole-1-carbonyl)-2-((1-methyl-1H-imidazol-5-yl)methyl)pentyl cyclopropanecarboxylate; (2R,3S)-3-(2-((2,6-dichlorophenyl)amino)-4,5-dihydro-1H-imidazole-1-carbonyl)-2-((1-methyl-1H-imidazol-5-yl)methyl)pentyl oleate; (2R,3S)-3-(2-((2,6-dichlorophenyl)amino)-4,5-dihydro-1H-imidazole-1-carbonyl)-2-((1-methyl-1H-imidazol-5-yl)methyl)pentyl (9Z,12Z)-octadeca-9,12-dienoate can be prepared in similar ways as Examples 15-24.

Example 25: In Vitro Metabolic Stability in Rabbit Cornea Homogenates

Dutch Belted rabbits will be euthanized with an overdose of sodium pentobarbital. The corneas will be collected and homogenized in ice-cold potassium chloride solution (pH=7.4). The homogenate will be centrifuged at 755×g for 30 min at 4° C. and aliquots of the supernatant will be stored at or below −70° C. until metabolism experiments will be conducted. Prior to storing the homogenates, an aliquot will be removed for the determination of protein concentrations by calculating the 260 nm absorbance using a spectrophotometer. All metabolic stability experiments will be performed in triplicate in 96-well plate format. The final incubation mixture will contain 1 μM test compound, 0.3 mg/mL corneal protein homogenate in a final volume of 0.5 mL 0.1 M potassium phosphate buffer (pH=6.0). The final percentage of solvent in the incubation will be less than 1.0% to prevent inhibition of enzymatic activity. Following a pre-incubation at 37° C., test article will be added to initiate the reaction. At designated time points (typically less than 60 minutes to capture the linear range of metabolite formation), 0.05 mL aliquots will be removed from the incubation mixtures using a clean pipet tip and immediately placed in organic solvent to stop any esterase activity. The hydrolysis to the metabolites will be confirmed to be due to esterase activity and not chemical stability. The samples will be analyzed by liquid chromatography with mass spectrometry (LC-MS/MS) detection to determine the metabolite concentrations resulting from the metabolism of the hybrid compounds. Internal standards were used to compensate for variability from sample processing, chromatographic elution, mass spectrometer response and ion suppression by matrix components. Table 2 will list the rate of metabolite formation in rabbit cornea homogenates.

TABLE 2

The rate of metabolite formation in rabbit cornea homogenates

| IUPAC Name | Rate of formation Metabolite 1 (nM/min/mg) | Rate of formation Metabolite 2 (nM/min/mg) |
|---|---|---|
| 3-((S)-1-(1H-imidazol-4-yl)ethyl)-2-methylbenzyl (2S,3R)-2-ethyl-4-hydroxy-3-((1-methyl-1H-imidazol-5-yl)methyl)butanoate | 5.56 ± 0.43 pilocarpine | 3.52 ± 0.23 Dexmedetomidine metabolite |
| 3-((S)-1-(1H-imidazol-4-yl)ethyl)-2-methylbenzyl (2S,3R)-4-acetoxy-2-ethyl-3-((1-methyl-1H-imidazol-5-yl)methyl)butanoate | 4.34 ± 0.11 pilocarpine | 2.87 ± 0.78 Dexmedetomidine metabolite |
| (((2S,3R)-2-ethyl-4-hydroxy-3-((1-methyl-1H-imidazol-5-yl)methyl)butanoyl)oxy)methyl 2-((4-bromo-1H-benzo[d]imidazol-5-yl)amino)-4,5-dihydro-1H-imidazole-1-carboxylate | 8.86 ± 0.13 pilocarpine | 1.23 ± 0.03 brimonidine metabolite |
| (((2S,3R)-4-acetoxy-2-ethyl-3-((1-methyl-1H-imidazol-5-yl)methyl)butanoyl)oxy)methyl 2-((4-bromo-1H-benzo[d]imidazol-5-yl)amino)-4,5-dihydro-1H-imidazole-1-carboxylate | 5.87 ± 0.97 pilocarpine | 6.34 ± 0.07 brimonidine metabolite |
| (((2S,3R)-2-ethyl-4-hydroxy-3-((1-methyl-1H-imidazol-5-yl)methyl)butanoyl)oxy)methyl 2-((5-bromoquinoxalin-6-yl)amino)-4,5-dihydro-1H-imidazole-1-carboxylate | 2.13 ± 0.24 pilocarpine | 4.98 ± 0.34 brimonidine |
| (((2S,3R)-4-acetoxy-2-ethyl-3-((1-methyl-1H-imidazol-5-yl)methyl)butanoyl)oxy)methyl 2-((5-bromoquinoxalin-6-yl)amino)-4,5-dihydro-1H-imidazole-1-carboxylate | 7.43 ± 0.27 pilocarpine | 1.98 ± 0.09 brimonidine |

Example 26: In Vivo Ocular Pharmacokinetics Following a Single Topical Ophthalmic Administration of (((2S,3R)-4-acetoxy-2-ethyl-3-((1-methyl-1H-imidazol-5-yl)methyl)butanoyl)oxy)methyl 2-((5-bromoquinoxalin-6-yl)amino)-4,5-dihydro-1H-imidazole-1-carboxylate in New Zealand White Rabbits Rabbits will be dosed once by ocular instillation to both eyes with each compound formulated in a 0.5% (w/v) solution. At 0.25, 0.5, 1, 2, 6 and 10 hours post dose, cornea, aqueous humor, conjunctiva and eyelid margin will be collected and stored at approximately −70° C. until bioanalysis. Ocular tissue samples will be analyzed by liquid chromatography with mass spectrometry detection to determine the parent and metabolite (pilocarpine and brimonidine) concentrations resulting from the metabolism of ester linked co-drugs. Internal standards will be used to compensate for variability from sample processing, chromatographic elution, mass spectrometer response and ion suppression by matrix components. Following a single topical ocular dose of 0.5% of the co-drug compound 10 hours in rabbits. The data listed in Table 3 will demonstrate that co-drug will penetrate into rabbit ocular tissues and enzymatically hydrolyze to the individual pilocarpine and brimonidine compound in cornea. This pharmacokinetic study will show that these co-drug compounds will have the capability to penetrate ocular tissues and get cleaved to the active metabolites to be clinically effective in treating ocular diseases.

TABLE 3

Concentrations of Co-drug and Metabolites in Cornea Tissue

| Conc. (ng/ml) | 0.25 hr | 0.5 hr | 1 hr | 2 hr | 6 hr | 10 hr |
|---|---|---|---|---|---|---|
| Co-drug | 7238 ± 345 | 987 ± 245 | 234 ± 33 | 95 ± 19 | 39 ± 37 | 12 ± 3 |
| Pilocarpine (Metabolite 1) | 39 ± 37 | 139 ± 78 | 379 ± 120 | 539 ± 30 | 754 ± 127 | 867 ± 37 |
| Brimonidine (Metabolite 2) | 24 ± 12 | 78 ± 54 | 98 ± 23 | 139 ± 37 | 339 ± 134 | 539 ± 97 |

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

Example 27: In Vivo Pharmacology Study of Measuring Pupil Size for Compounds 2, 4 and 9 in Dutch-Belted Rabbits Study Design Three (3) female Dutch belted rabbits were randomly assigned to each group by Provantis or Excel based on body weight. Each animal was dosed 40 μL of testing article (see Table 4 below) to both eyes. The pupil sizes of both eyes were measured at baseline (30 minutes before dosing), 0.5 h, 1 h, 2 h, 3 h, 4 h, 6 h, 8 h after dosing. The pupil size measurement data were analyzed for efficacy of pupil constriction. CBT compounds tested are co-drugs of pilocarpine-alpha adrenergic agonists as described above. The vehicle used to dissolve CBT compounds is the same as the vehicle used in the negative control in group 1. Positive control 1 is 1.25% Pilocarpine HCl in an aqueous buffer. Positive control 2 is 3.0% Carbachol and 0.2% Brimonidine in an aqueous buffer. This control can result in a large pupil constrictive effect.

TABLE 4

Study design

| Group | Testing article |
|---|---|
| 1 | Vehicle negative control |
| 2 | 0.5% Compound-2 |
| 3 | 2% Compound-2 |
| 4 | 0.5% Compound-4 |
| 5 | 2% Compound-4 |
| 6 | 2% Compound-9 |
| 7 | Positive control 1 |
| 8 | Positive control 2 |

Results

Figure 2:
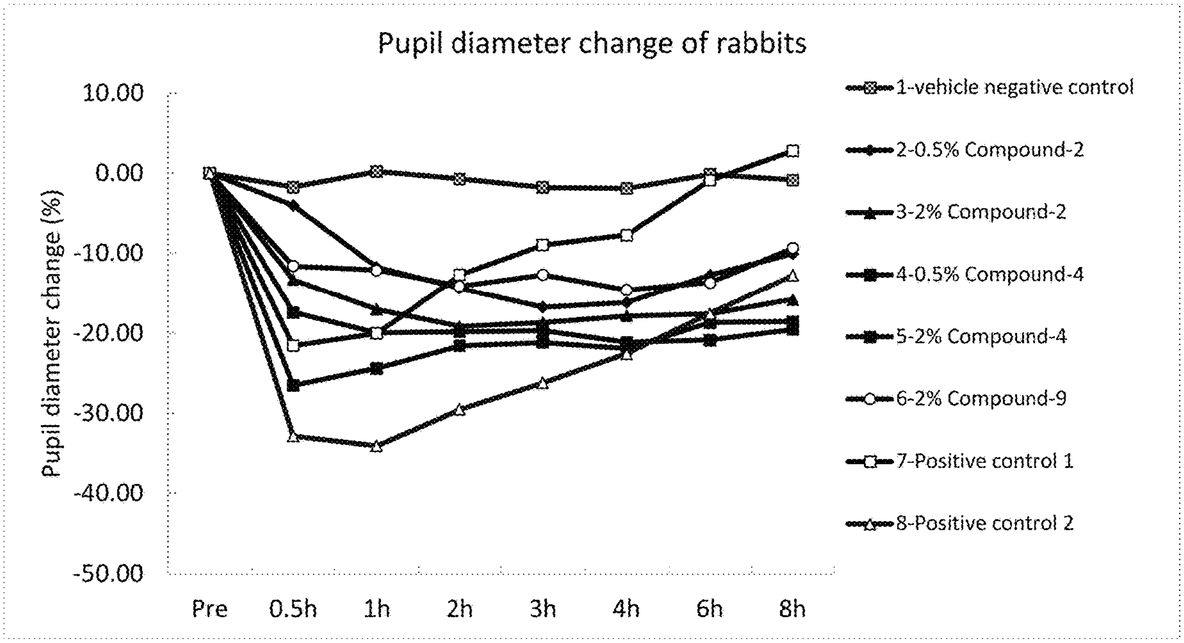
FIG. 2 shows rabbit pupil constriction effects by co-drugs compounds-2, 4 and 9.

FIG. 2 shows the pupil constrictive effects of the co-drug compounds and two positive controls. As expected, Positive control 1 caused a moderate constrict of pupil and Positive control 2 showed a very strong pupil-constriction. The co-drugs all showed pupil-constricting activities. Compound-4 showed better potency than Compound-2 and Compound-9. Compound-2 and Compound-4 also showed dose-related effects in this range. The tested co-drugs showed efficacies similar to that of positive control 1. In addition, the effects of these co-drugs lasted much longer, having a much flatter curve than the two positive controls. The results indicated that the co-drugs dissociated over time to release each of the components and as a result, led to sustained pupil constriction.

Example 28: In Vivo Pharmacology Study of Measuring Pupil Size for Compounds 15, 16, 19 and 20 in Dutch-Belted Rabbits Study Design Three (3) female Dutch belted rabbits were randomly assigned to each group by Provantis or Excel based on body weight. Each animal was dosed 40 μL of testing article (see Table 5 below) to both eyes. The pupil sizes of both eyes were measured at baseline (30 minutes before dosing), 0.5 h, 1 h, 2 h, 3 h, 4 h, 6 h, 8 h, 24 h after dosing. The pupil size measurement data were analyzed for efficacy of pupil constriction. Co-drug compounds are co-drugs of pilocarpine-alpha adrenergic agonists as described above. The vehicle used to dissolve Co-drug compounds is the same as the vehicle used in the negative control in group 1. Positive control 1 is 1.25% Pilocarpine HCl in an aqueous buffer. Positive control 2 is 3.0% Carbachol and 0.2% Brimonidine in an aqueous buffer. This control can result in a large pupil constrictive effect.

TABLE 5

Study design

| Group | Testing article |
|---|---|
| 1 | Vehicle negative control |
| 2 | 1% Compound-15 |
| 3 | 1% Compound-16 |
| 4 | 1% Compound-19 |
| 5 | 1% Compound-20 |
| 7 | Positive control 1 |
| 8 | Positive control 2 |

Results

Figure 3:
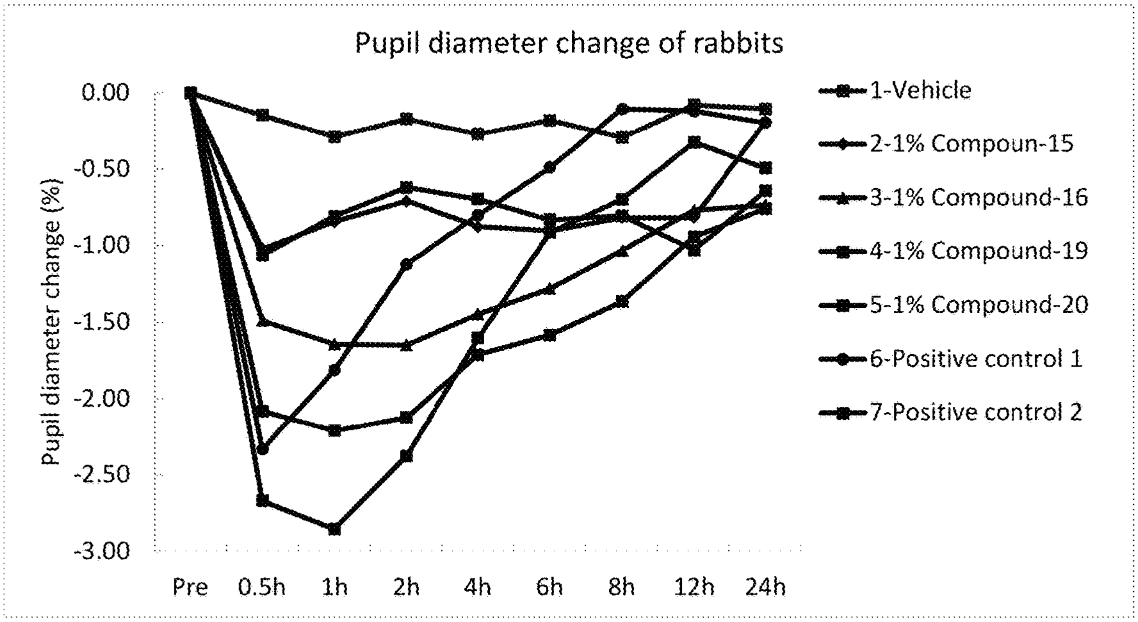
FIG. 3 shows rabbit pupil constriction effects by co-drugs compounds-15, 16, 19 and 20.

FIG. 3 shows the pupil constrictive effects of the co-drug compounds and two positive controls. As in the previous example above, Positive control 1 caused a moderate constrict of pupil and Positive control 2 showed a very strong pupil-constriction. Again, the co-drugs all showed pupil-constricting activities. Compound-16 and Compound-20, the brimonidine-containing co-drugs, showed better potency than Compound-15 and Compound-19, the brimonidine analog-containing co-drugs. The results indicates that brimonidine has significantly better potency. Compound-16 and Compound-20 also showed efficacies similar to that of positive control 1. Like in the last example, the effects of co-drugs lasted much longer, having a much flatter curve than the two positive controls.

What is claimed is:

1. A co-drug comprising a muscarinic agonist moiety and an alpha2 adrenergic agonist moiety, or a pharmaceutical salt thereof, wherein the muscarinic agonist moiety and the alpha2 adrenergic agonist moiety are connected covalently via a linker, and the link comprises an ester bond, an amide bond, a carbamate bond, or a combination thereof.

2. The co-drug of claim 1, wherein the co-drug is a compound of Formula I, an enantiomer, a diastereoisomer, a hydrate, a solvate, a crystal form, or a tautomer thereof, Formula I

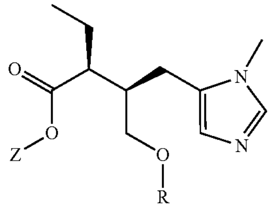

wherein:

R is H, —CO—$C_{1-8}$ alkyl, —CO—$C_{1-8}$ alkyloxy; —CO-aryl, —CO-aryloxy, —CO—$C_{1-8}$ alkylaryl, or —CO—$C_{1-8}$ alkylaryloxy;

Z is

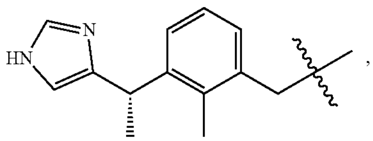,

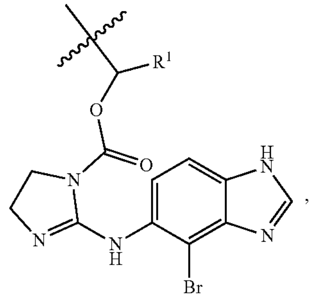,

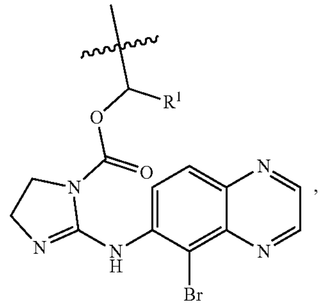,

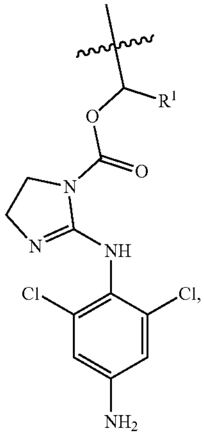 or 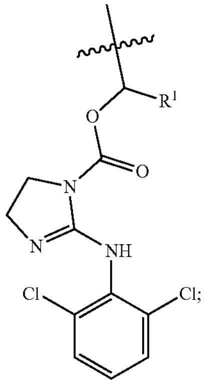

and $R^1$ is H or $C_{1-3}$ alkyl.

3. The co-drug of claim 1, wherein the co-drug is a compound of Formula II, an enantiomer, a diastereoisomer, a hydrate, a solvate, a crystal form, or a tautomer thereof, Formula II

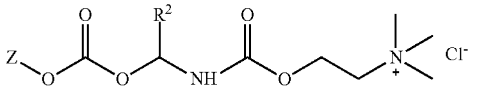

wherein:

$R^2$ is H, $C_{1-3}$ alkyl; $C_{1-8}$ alkyloxy; aryl, aryloxy, $C_{1-8}$ alkylaryl, or $C_{1-8}$ alkylaryloxy;

Z is

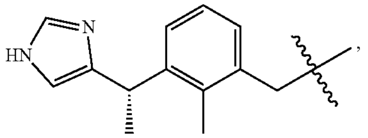,

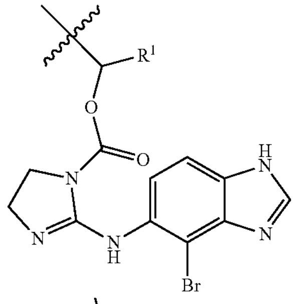,

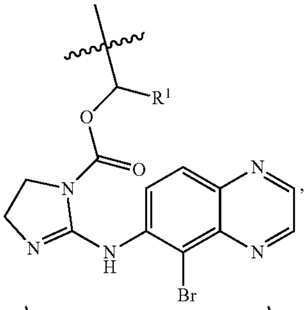,

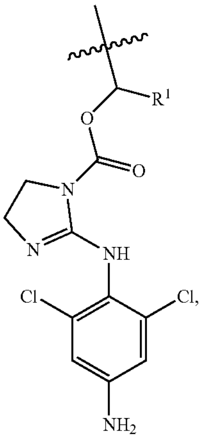 or 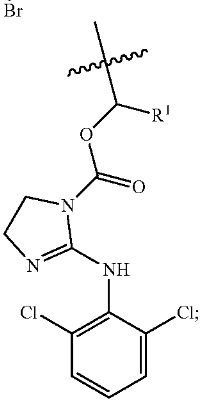

and $R^1$ is H or $C_{1-3}$ alkyl.

4. The co-drug of claim 1, wherein the co-drug is a compound of Formula III, an enantiomer, a diastereoisomer, a hydrate, a solvate, a crystal form, or a tautomer thereof, Formula III

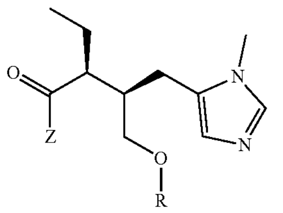

wherein:

R is H, —CO—$C_{1-18}$ alkyl, —CO—$C_{1-18}$ alkyloxy; —CO-aryl, —CO-aryloxy, —CO—$C_{1-18}$ alkylaryl, or —CO—$C_{1-18}$ alkylaryloxy; and Z is:

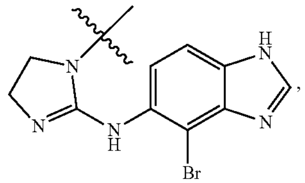

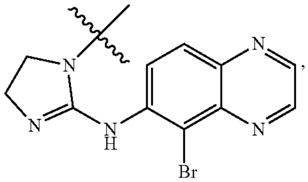

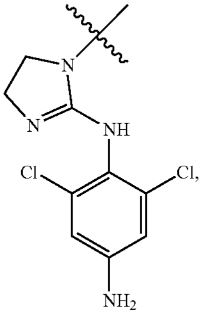

or

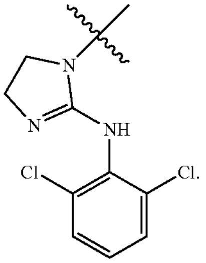

5. The co-drug of claim 1, wherein the co-drug is selected from the group consisting of 3-((S)-1-(1H-imidazol-4-yl)ethyl)-2-methylbenzyl (2S,3R)-2-ethyl-4-hydroxy-3-((1-methyl-1H-imidazol-5-yl)methyl) butanoate; 3-((S)-1-(1H-imidazol-4-yl)ethyl)-2-methylbenzyl (2S,3R)-4-acetoxy-2-ethyl-3-((1-methyl-1H-imidazol-5-yl)methyl) butanoate; (((2S,3R)-2-ethyl-4-hydroxy-3-((1-methyl-1H-imidazol-5-yl)methyl)butanoyl)oxy)methyl 2-((4-bromo-1H-benzo[d]imidazol-5-yl)amino)-4,5-dihydro-1H-imidazole-1-carboxylate; (((2S,3R)-4-acetoxy-2-ethyl-3-((1-methyl-1H-imidazol-5-yl)methyl)butanoyl)oxy)methyl 2-((4-bromo-1H-benzo[d]imidazol-5-yl)amino)-4,5-dihydro-1H-imidazole-1-carboxylate; (((2S,3R)-2-ethyl-4-hydroxy-3-((1-methyl-1H-imidazol-5-yl)methyl)butanoyl)oxy)methyl 2-((5-bromoquinoxalin-6-yl)amino)-4,5-dihydro-1H-imidazole-1-carboxylate; (((2S,3R)-4-acetoxy-2-ethyl-3-((1-methyl-1H-imidazol-5-yl)methyl)butanoyl)oxy)methyl 2-((5-bromoquinoxalin-6-yl)amino)-4,5-dihydro-1H-imidazole-1-carboxylate; 1-(((2S,3R)-2-ethyl-4-hydroxy-3-((1-methyl-1H-imidazol-5-yl)methyl)butanoyl)oxy)ethyl 2-((4-bromo-1H-benzo[d]imidazol-5-yl)amino)-4,5-dihydro-1H-imidazole-1-carboxylate; 1-(((2S,3R)-4-acetoxy-2-ethyl-3-((1-methyl-1H-imidazol-5-yl)methyl)butanoyl)oxy)ethyl 2-((4-bromo-1H-benzo[d]imidazol-5-yl)amino)-4,5-dihydro-1H-imidazole-1-carboxylate; 1-(((2S,3R)-2-ethyl-4-hydroxy-3-((1-methyl-1H-imidazol-5-yl)methyl)butanoyl)oxy)ethyl 2-((5-bromoquinoxalin-6-yl)amino)-4,5-dihydro-1H-imidazole-1-carboxylate; 1-(((2S,3R)-4-acetoxy-2-ethyl-3-((1-methyl-1H-imidazol-5-yl)methyl)-butanoyl)oxy)ethyl 2-((5-bromoquinoxalin-6-yl)amino)-4,5-dihydro-1H-imidazole-1-carboxylate; (2R,3S)-3-(2-((4-bromo-1H-benzo[d]imidazol-5-yl)amino)-4,5-dihydro-1H-imidazole-1-carbonyl)-2-((1-methyl-1H-imidazol-5-yl)methyl)pentyl acetate; (2R,3S)-3-(2-((4-bromo-1H-benzo[d]imidazol-5-yl)amino)-4,5-dihydro-1H-imidazole-1-carbonyl)-2-((1-methyl-1H-imidazol-5-yl)methyl)pentyl propionate; (2R,3S)-3-(2-((4-bromo-1H-benzo[d]imidazol-5-yl)amino)-4,5-dihydro-1H-imidazole-1-carbonyl)-2-((1-methyl-1H-imidazol-5-yl)methyl)pentyl butyrate; (2R,3S)-3-(2-((4-bromo-1H-benzo[d]imidazol-5-yl)amino)-4,5-dihydro-1H-imidazole-1-carbonyl)-2-((1-methyl-1H-imidazol-5-yl)methyl)pentyl cyclopropanecarboxylate; (2R,3S)-3-(2-((4-bromo-1H-benzo[d]imidazol-5-yl)amino)-4,5-dihydro-1H-imidazole-1-carbonyl)-2-((1-methyl-1H-imidazol-5-yl)methyl)pentyl oleate; (2R,3S)-3-(2-((4-bromo-1H-benzo[d]imidazol-5-yl)amino)-4,5-dihydro-1H-imidazole-1-carbonyl)-2-((1-methyl-1H-imidazol-5-yl)methyl)pentyl (9Z,12Z)-octadeca-9,12-dienoate; (2R,3S)-3-(2-((5-bromoquinoxalin-6-yl)amino)-4,5-dihydro-1H-imidazole-1-carbonyl)-2-((1-methyl-1H-imidazol-5-yl)methyl)pentyl acetate; (2R,3S)-3-(2-((5-bromoquinoxalin-6-yl)amino)-4,5-dihydro-1H-imidazole-1-carbonyl)-2-((1-methyl-1H-imidazol-5-yl)methyl)pentyl propionate; (2R,3S)-3-(2-((5-bromoquinoxalin-6-yl)amino)-4,5-dihydro-1H-imidazole-1-carbonyl)-2-((1-methyl-1H-imidazol-5-yl)methyl)pentyl butyrate; (2R,3S)-3-(2-((5-bromoquinoxalin-6-yl)amino)-4,5-dihydro-1H-imidazole-1-carbonyl)-2-((1-methyl-1H-imidazol-5-yl)methyl)pentyl cyclopropanecarboxylate; (2R,3S)-3-(2-((5-bromoquinoxalin-6-yl)amino)-4,5-dihydro-1H-imidazole-1-carbonyl)-2-((1-methyl-1H-imidazol-5-yl)methyl)pentyl oleate; (2R,3S)-3-(2-((5-bromoquinoxalin-6-yl)amino)-4,5-dihydro-1H-imidazole-1-carbonyl)-2-((1-methyl-1H-imidazol-5-yl)methyl)pentyl (9Z,12Z)-octadeca-9,12-dienoate; (2R,3S)-3-(2-((4-amino-2,6-dichlorophenyl)amino)-4,5-dihydro-1H-imidazole-1-carbonyl)-2-((1-methyl-1H-imidazol-5-yl)methyl)pentyl acetate; (2R,3S)-3-(2-((4-amino-2,6-dichlorophenyl)amino)-4,5-dihydro-1H-imidazole-1-carbonyl)-2-((1-methyl-1H-imidazol-5-yl)methyl)pentyl propionate; (2R,3S)-3-(2-((4-amino-2,6-dichlorophenyl)amino)-4,5-dihydro-1H-imidazole-1-carbonyl)-2-((1-methyl-1H-imidazol-5-yl)methyl)pentyl butyrate; (2R,3S)-3-(2-((4-amino-2,6-dichlorophenyl)amino)-4,5-dihydro-1H-imidazole-1-carbonyl)-2-((1-methyl-1H-imidazol-5-yl)methyl)pentyl cyclopropanecarboxylate; (2R,3S)-3-(2-((4-amino-2,6-dichlorophenyl)amino)-4,5-dihydro-1H-imidazole-1-carbonyl)-2-((1-methyl-1H-imidazol-5-yl)methyl)pentyl oleate; (2R,3S)-3-(2-((4-amino-2,6-dichlorophenyl)amino)-4,5-dihydro-1H-imidazole-1-carbonyl)-2-((1-methyl-1H-imidazol-5-yl)methyl)pentyl (9Z,12Z)-octadeca-9,12-dienoate; (2R,3S)-3-(2-((2,6-dichlorophenyl)amino)-4,5-dihydro-1H-imidazole-1-carbonyl)-2-((1-methyl-1H-imidazol-5-yl)methyl)pentyl acetate; (2R,3S)-3-(2-((2,6-dichlorophenyl)amino)-4,5-dihydro-1H-imidazole-1-carbonyl)-2-((1-methyl-1H-imidazol-5-yl)methyl)pentyl propionate; (2R,3S)-3-(2-((2,6-dichlorophenyl)amino)-4,5-dihydro-1H-imidazole-1-carbonyl)-2-((1-methyl-1H-imidazol-5-yl)methyl)pentyl butyrate; (2R,3S)-3-(2-((2,6-dichlorophenyl)amino)-4,5-dihydro-1H-imidazole-1-carbonyl)-2-((1-methyl-1H-imidazol-5-yl)methyl)pentyl cyclopropanecarboxylate; (2R,3S)-3-(2-((2,6-dichlorophenyl)amino)-4,5-dihydro-1H-imidazole-1-carbonyl)-2-((1-methyl-1H-imidazol-5-yl)methyl)pentyl oleate; and (2R,3S)-3-(2-((2,6-dichlorophenyl)amino)-4,5-dihydro-1H-imidazole-1-carbonyl)-2-((1-methyl-1H-imidazol-5-yl)methyl)pentyl (9Z,12Z)-octadeca-9,12-dienoate.

6. A pharmaceutical composition comprising as active ingredient a therapeutically effective amount of the co-drug according to claim 1 and a pharmaceutically acceptable adjuvant, diluent or carrier.

7. The pharmaceutical composition of claim 6, wherein the pharmaceutical composition is formulated for ocular administration, systemic administration, oral administration, intravenous administration, intradermal administration, or intracavernous administration.

8. The pharmaceutical composition of claim 7, wherein the pharmaceutical composition is an eyedrop, a gel, or an implant.

9. The pharmaceutical formulation of claim 8, wherein the eyedrop is a solution, a suspension, or an emulsion.

* * * * *